(12) United States Patent
Tachibana et al.

(10) Patent No.: US 10,007,183 B2
(45) Date of Patent: Jun. 26, 2018

(54) COMPOUND FOR FORMING ORGANIC FILM, AND ORGANIC FILM COMPOSITION USING THE SAME, PROCESS FOR FORMING ORGANIC FILM, AND PATTERNING PROCESS

(71) Applicant: SHIN-ETSU CHEMICAL CO., LTD., Tokyo (JP)

(72) Inventors: Seiichiro Tachibana, Jyoetsu (JP); Daisuke Kori, Jyoetsu (JP); Tsutomu Ogihara, Jyoetsu (JP); Takeru Watanabe, Jyoetsu (JP); Kazumi Noda, Jyoetsu (JP); Toshiharu Yano, Jyoetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days. days.

(21) Appl. No.: 14/856,014

(22) Filed: Sep. 16, 2015

(65) Prior Publication Data

US 2016/0027653 A1    Jan. 28, 2016

Related U.S. Application Data

(62) Division of application No. 13/916,071, filed on Jun. 12, 2013, now Pat. No. 9,261,788.

(30) Foreign Application Priority Data

Jun. 18, 2012    (JP) .................................. 2012-137073

(51) Int. Cl.
*G03F 7/11*    (2006.01)
*G03F 7/40*    (2006.01)
(Continued)

(52) U.S. Cl.
CPC .............. *G03F 7/094* (2013.01); *C07C 39/17* (2013.01); *C07C 43/23* (2013.01); *C08F 216/10* (2013.01);
(Continued)

(58) Field of Classification Search
CPC ......... H01L 2224/2919; H01L 27/1203; H01L 21/31144; H01L 21/32139; G03F 9/7034;
(Continued)

(56) References Cited

U.S. PATENT DOCUMENTS 5,376,498 A    12/1994 Kajita et al.
5,432,256 A    7/1995 Abe et al.
(Continued)

FOREIGN PATENT DOCUMENTS

JP    08-176289 A    7/1996
JP    2002-334869 A    11/2002
(Continued)

OTHER PUBLICATIONS

Dec. 22, 2015 Office Action issued in Japanese Application No. 2013-079182.
(Continued)

*Primary Examiner* — Cynthia Hamilton
(74) *Attorney, Agent, or Firm* — Oliff PLC

(57) ABSTRACT

The invention provides a compound for forming an organic film having a partial structure represented by the following formula (ii), (ii)

$$\left[ \left( \begin{matrix} Ar1 \\ Ar2 \end{matrix} \right) \left( \begin{matrix} Ar3 \\ R^0 \end{matrix} \right)_e - L_0 - \left( \begin{matrix} Ar3 \\ R^0 \end{matrix} \right)_e \left( \begin{matrix} Ar1 \\ Ar2 \end{matrix} \right) \right]$$

(Continued)

wherein the ring structures Ar1, Ar2 and Ar3 each represent a substituted or unsubstituted benzene ring or naphthalene ring; e is 0 or 1; $R^O$ represents a hydrogen atom or a linear, branched or cyclic monovalent organic group having 1 to 30 carbon atoms; $L_O$ represents a linear, branched or cyclic divalent organic group having 1 to 32 carbon atoms; and the methylene group constituting $L_O$ may be substituted by an oxygen atom or a carbonyl group. There can be provided an organic film composition for forming an organic film having high dry etching resistance as well as advanced filling/planarizing characteristics.

28 Claims, 3 Drawing Sheets

(51) Int. Cl.
| | |
|---|---|
| G03F 7/09 | (2006.01) |
| H01L 21/308 | (2006.01) |
| C07C 43/23 | (2006.01) |
| G03F 7/075 | (2006.01) |
| C08F 216/10 | (2006.01) |
| C08G 61/12 | (2006.01) |
| C09D 129/02 | (2006.01) |
| C09D 165/00 | (2006.01) |
| G03F 7/20 | (2006.01) |
| G03F 7/32 | (2006.01) |
| C07C 39/17 | (2006.01) |
| C08K 5/13 | (2006.01) |
| H01L 21/02 | (2006.01) |
| H01L 27/12 | (2006.01) |
| H01L 21/311 | (2006.01) |
| H01L 21/027 | (2006.01) |

(52) U.S. Cl.
CPC ............ *C08G 61/12* (2013.01); *C08K 5/13* (2013.01); *C09D 7/63* (2018.01); *C09D 129/02* (2013.01); *C09D 165/00* (2013.01); *G03F 7/0752* (2013.01); *G03F 7/091* (2013.01); *G03F 7/11* (2013.01); *G03F 7/20* (2013.01); *G03F 7/32* (2013.01); *G03F 7/40* (2013.01); *H01L 21/0214* (2013.01); *H01L 21/0217* (2013.01); *H01L 21/0228* (2013.01); *H01L 21/0271* (2013.01); *H01L 21/0276* (2013.01); *H01L 21/02118* (2013.01); *H01L 21/02164* (2013.01); *H01L 21/02271* (2013.01); *H01L 21/02318* (2013.01); *H01L 21/308* (2013.01); *H01L 21/3081* (2013.01); *H01L 21/3086* (2013.01); *H01L 21/31138* (2013.01); *C07C 2603/18* (2017.05); *H01L 21/0274* (2013.01); *H01L 21/31144* (2013.01); *H01L 27/1203* (2013.01)

(58) Field of Classification Search
CPC . G03F 7/091; G03F 7/094; G03F 7/11; G03F 7/0752; C07C 43/2055; C07C 43/21; C07C 43/23
See application file for complete search history.

(56) References Cited

U.S. PATENT DOCUMENTS

| | | | |
|---|---|---|---|
| 8,835,697 B2 | 9/2014 | Kori et al. | |
| 2002/0106909 A1 | 8/2002 | Kato et al. | |
| 2007/0148586 A1 | 6/2007 | Uh et al. | |
| 2008/0305441 A1 | 12/2008 | Yoon et al. | |
| 2009/0242822 A1 | 10/2009 | Gerster et al. | |
| 2009/0274978 A1 | 11/2009 | Ohashi et al. | |
| 2009/0311624 A1 | 12/2009 | Horiguchi et al. | |
| 2011/0027722 A1* | 2/2011 | Cho | C08G 77/04 430/323 |
| 2011/0236595 A1 | 9/2011 | Kodama et al. | |
| 2013/0337649 A1 | 12/2013 | Tachibana et al. | |
| 2014/0349222 A1 | 11/2014 | Shibui et al. | |

FOREIGN PATENT DOCUMENTS

| | | |
|---|---|---|
| JP | 2003-183378 A | 7/2003 |
| JP | 2004-205685 A | 7/2004 |
| JP | 2006-219378 A | 8/2006 |
| JP | 2006-227391 A | 8/2006 |
| JP | 2007-178974 A | 7/2007 |
| JP | 2007-199653 A | 8/2007 |
| JP | 2009-269953 A | 11/2009 |
| JP | 2010-529499 A | 8/2010 |
| JP | 4784784 B2 | 10/2011 |
| JP | 2013-209571 A | 10/2013 |
| JP | 2014-024831 A | 2/2014 |
| JP | 5598489 B2 | 10/2014 |
| WO | 2013/085004 A1 | 6/2013 |

OTHER PUBLICATIONS

Zhurnal Organicheskoj Khimii, 1986, 22 (10), pp. 2175-2178.
Hasegawa et al., "Macromolecules," American Chemical Society, 2010, 43 (1), pp. 131-136.
Oct. 27, 2015 Office Action issued in Japanese Application No. 2013-079182.
Jul. 12, 2016 Notification of Reasons for Refusal issued in Japanese Application No. 2015-232690.
Feb. 10, 2017 Office Action Issued in U.S. Appl. No. 14/856,094.
Apr. 11, 2017 Office Action issued in Korean Patent Application No. 2013-0068812.
Aug. 23, 2017 Office Action issued in U.S. Appl. No. 14/856,094.

* cited by examiner

COMPOUND FOR FORMING ORGANIC FILM, AND ORGANIC FILM COMPOSITION USING THE SAME, PROCESS FOR FORMING ORGANIC FILM, AND PATTERNING PROCESS

BACKGROUND OF THE INVENTION

Field of the Invention

The present invention relates to a resist underlayer film composition to be used in a multilayer resist step which is used for a fine patterning in a manufacturing step of a semiconductor apparatus, etc., or an organic film composition effective for a planarizing composition for manufacturing a semiconductor apparatus, a process for forming a film using the same, a patterning process using the underlayer composition suitable for exposure by far ultraviolet rays, KrF excimer laser (248 nm), ArF excimer laser (193 nm), $F_2$ laser (157 nm), $Kr_2$ laser (146 nm), $Ar_2$ laser (126 nm), soft X-rays (EUV), electron beam (EB), an ion beam, X-rays, or the like, and a compound for forming an organic film useful as a component of the film composition.

Description of the Related Art

With a tendency of high integration and high-speed of LSI, a finer pattern size is required. Along with the requirement of finer pattern size, the lithography technologies have accomplished fine patterning by using light sources with shorter wavelength and properly selecting resist compositions corresponding to the light source. As for such compositions, positive photoresist compositions used as a monolayer are mainly selected. Each of these monolayer positive photoresist compositions has a skeleton providing an etching resistance against dry etching with chlorine-based gas plasma or fluorine-based gas plasma in the resist resin, and has resist mechanism that an exposed area turns soluble, thereby forming a pattern by dissolving the exposed area and dry etching a substrate to be processed to which the resist composition is applied by using the remained resist pattern as an etching mask.

However, when a pattern become finer, that is, a pattern width is changed narrower, without changing the thickness of a photoresist film to be used, resolution performance of the photoresist film is lowered. In addition, developing the pattern of the photoresist film with a developer causes a pattern fall because a so-called aspect ratio of the pattern becomes too high. Therefore, the thickness of a photoresist film has been made thinner along with advancing a finer pattern.

On the other hand, for processing a substrate to be processed, a method to process the substrate by dry etching by using a pattern-formed photoresist film as an etching mask is usually used. Actually however, there is no dry etching method capable of providing an absolute etching selectivity between the photoresist film and the substrate to be processed. Therefore, the resist film is also damaged and fallen during processing the substrate, so that the resist pattern cannot be transferred to the substrate to be processed correctly. Accordingly, as a pattern becomes finer, it has been required that a resist composition has a higher dry etching resistance. In addition, the use of shorter wavelength exposure radiations has required resins used for photoresist compositions to have low absorbance at the wavelength to be used for the exposure. Accordingly, as the radiation shifts from i-beam to KrF and to ArF, the resin shifts to novolac resins, polyhydroxystyrene, and resins having an aliphatic polycyclic skeleton. Along with this shift, an etching rate of the resin actually becomes higher under the dry etching conditions mentioned above, and recent photoresist compositions having a high resolution tend to have a low etching resistance.

As a result, a substrate to be processed has to be dry etched with a thinner photoresist film having lower etching resistance. The need to provide a composition for this process and the process itself has become urgent.

A multilayer resist process is one of solutions for these problems. This method is as follows: a middle layer film having a different etching selectivity from a photoresist film, that is, a resist upper layer film, is set between the resist upper layer film and a substrate to be processed, and then, to obtain a pattern on the resist upper layer film; the resist upper layer pattern is transferred to the middle layer film by dry etching by using the upper layer resist pattern as a dry etching mask; and then the middle layer pattern is transferred to the substrate to be processed by dry etching by using the middle layer film as a dry etching mask.

The multi-layer resist process further include a three-layer resist process which can be performed by using a typical resist composition used in a monolayer resist process. For example, this method is configured to form: an organic film based on novolac or the like as a resist underlayer film on a substrate to be processed; a silicon-containing film as a resist middle layer film thereon; and a usual organic photoresist film as a resist upper layer film thereon. Since the organic resist upper layer film exhibits an excellent etching selectivity ratio relative to the silicon-containing resist middle layer film for dry etching by fluorine-based gas plasma, the resist pattern is transferred to the silicon-containing resist middle layer film by means of dry etching based on fluorine-based gas plasma. Further, since the silicon-containing resist middle layer film exhibits an excellent etching selectivity ratio relative to an organic underlayer in the etching using an oxygen gas or a hydrogen gas, film pattern of the silicon-containing middle layer film is transferred to the underlayer by means of etching based on an oxygen gas or a hydrogen gas. According to this process, even when a resist composition which is difficult to form a pattern having a sufficient film thickness for directly processing the substrate to be processed or a resist composition which has insufficient dry etching resistance for processing the substrate is used, a novolac resin film pattern having a sufficient dry etching resistance for the processing can be obtained when the pattern can be transferred to the silicon-containing film.

While numerous process have been known (for example, Patent Document 1) for the organic underlayer film as described above, in recent years, it has now been growing necessity to have excellent filling property and planarizing characteristics in addition to dry etching characteristics. For example, when a basis substrate to be processed has a fine pattern structural composition such as a hole or a trench, it is necessary to have filling property which fills in the pattern with a film without any voids. In addition, when the substrate to be processed as a basis has a step(s), or when a pattern dense portion and no pattern region exist on the same substrate, it is necessary to planarizing the film surface by the underlayer. By planarizing the surface of the underlayer, fluctuation in the film thickness of a middle layer or a photoresist formed thereon is controlled, whereby a focus margin in lithography or a margin in the processing step of the substrate to be processed thereafter can be enlarged.

As a means to improve filling/planarizing characteristics of an underlayer composition, addition of a liquid state additive such as a polyether polyol has been proposed (Patent Document 2). However, the organic film formed by the method contains a large amount of the polyether polyol units, etching resistance of which are inferior, so that the etching resistance of the resulting film is markedly lowered whereby it is not suitable for an underlayer for the three-layer resist. Thus, it has been desired to develop a resist underlayer film composition having both of excellent filling/planarizing characteristics and sufficient etching resistance, and a patterning process using the same.

Also, uses of an organic film composition excellent in filling/planarizing characteristics are not limited only to an underlayer for the three-layer resist, and it can be widely applied as a planarizing composition for manufacturing a semiconductor apparatus, for example, substrate planarizing prior to patterning by nano imprinting, etc. Moreover, for global planarizing during the preparation process of the semiconductor apparatus, a CMP process has now generally been used, but the CMP is a high cost process, so that such a composition can be expected to be a composition which is to bear the global planarizing method to be used in place of the CMP.

PRIOR ART DOCUMENTS

Patent Documents

[Patent Document 1] Japanese Patent Laid-Open Publication No. 2004-205685
[Patent Document 2] Japanese Patent No. 4784784

SUMMARY OF THE INVENTION

The present invention has been done in view of the situation as mentioned and an object thereof is to provide an organic film composition for forming an organic film having high dry etching resistance as well as advanced filling/planarizing characteristics.

In order to solve the problems, the present invention provides a compound for forming an organic film having a partial structure represented by the following formula (i) or (ii), wherein the ring structures Ar1, Ar2 and Ar3 each represent a substituted or unsubstituted benzene ring or naphthalene ring; e is 0 or 1; $R^0$ represents a hydrogen atom or a linear, branched or cyclic monovalent organic group having 1 to 30 carbon atoms; $L_0$ represents a linear, branched or cyclic divalent organic group having 1 to 32 carbon atoms; and the methylene group constituting $L_0$ may be substituted by an oxygen atom or a carbonyl group.

Such a compound for forming an organic film enables to provide an organic film composition for forming an organic film having high dry etching resistance as well as advanced filling/planarizing characteristics.

Also, the compound for forming an organic film containing a compound represented by the following formula (iii) is provided,

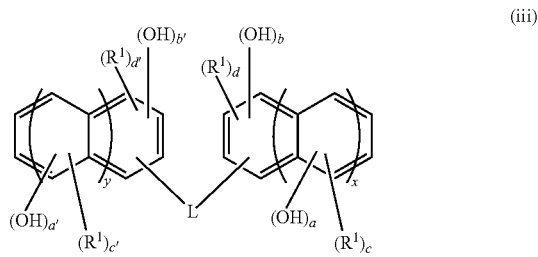

wherein $R^1$ represents a linear, branched or cyclic monovalent hydrocarbon group having 1 to 20 carbon atoms, and the methylene group constituting $R^1$ may be substituted by an oxygen atom; a+b and a'+b' are each independently 1, 2 or 3; c, d, c' and d' are each independently 0, 1 or 2; x and y each independently represent 0 or 1, when x=0, then a=c=0, and when y=0, then a'=c'=0; and L represents a partial structure represented by the formula (ii).

In this case, the compound represented by the formula (iii) is preferably a compound containing an aliphatic hydrocarbon group represented by the following formula (1),

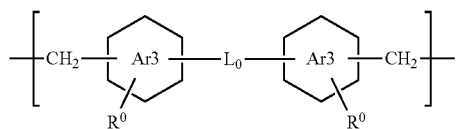

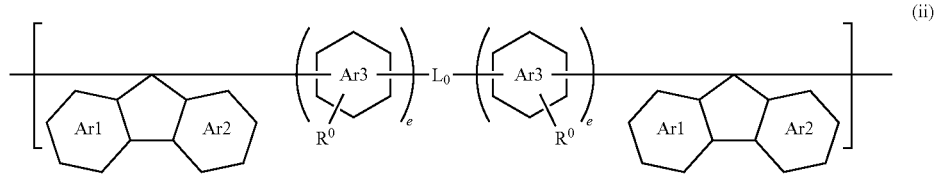

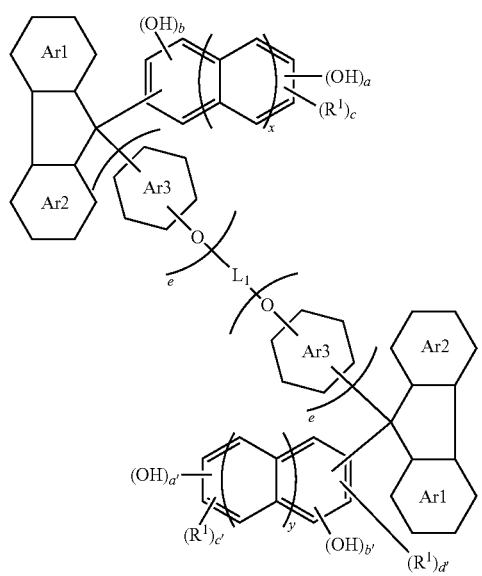

(1)

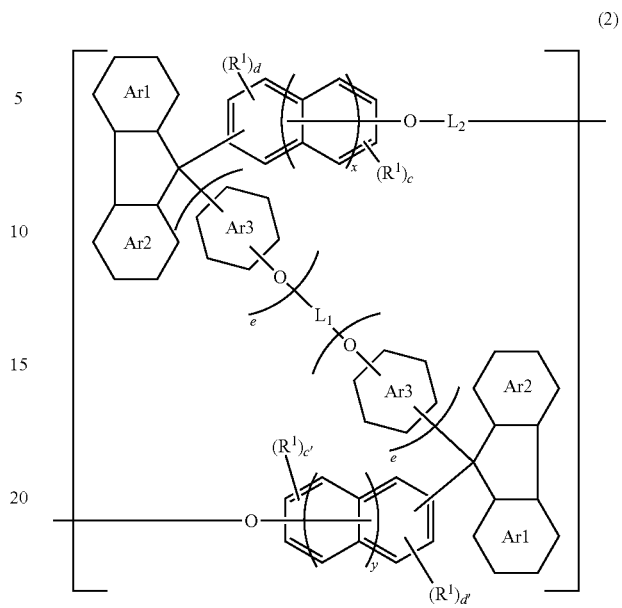

(2)

wherein Ar1, Ar2, Ar3, $R^1$, a, b, a', b', c, d, c', d', x, y and e have the same meanings as defined above; $L_1$ represents a linear, branched or cyclic divalent hydrocarbon group having 2 to 30 carbon atoms containing an aliphatic hydrocarbon group, and the methylene group constituting $L_1$ may be substituted by an oxygen atom or a carbonyl group.

Further, the compound for forming an organic film having a partial structure represented by the following formula (iv) is provided, wherein Ar1, Ar2, Ar3, $R^1$, c, d, c', d', x, y, e and $L_2$ have the same meanings as defined above; $L_1$ represents a linear, branched or cyclic divalent hydrocarbon group having 2 to 30 carbon atoms containing an aliphatic hydrocarbon group, and the methylene group constituting $L_1$ may be substituted by an oxygen atom or a carbonyl group.

Moreover, the compound for forming an organic film preferably contains a polymer compound having a partial structure represented by the following formula (v),

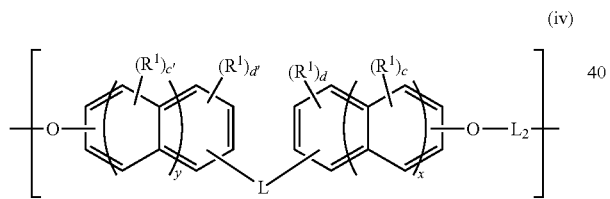

(iv)

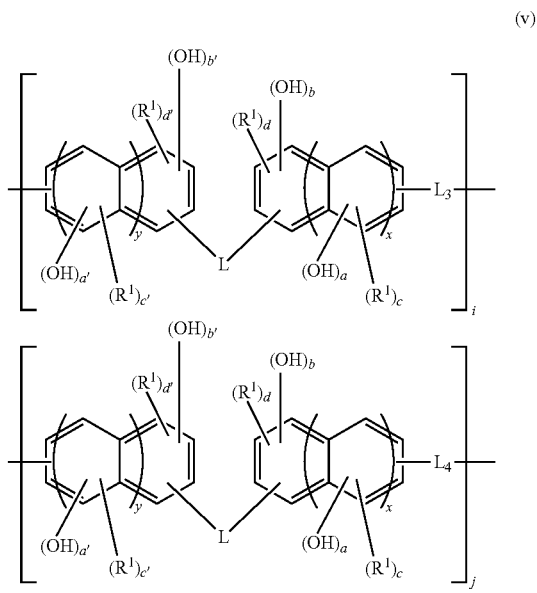

(v)

wherein $R^1$ represents a linear, branched or cyclic monovalent hydrocarbon group having 1 to 20 carbon atoms, and the methylene group constituting $R^1$ may be substituted by an oxygen atom; c, d, c' and d' are each independently 0, 1 or 2; x and y each independently represent 0 or 1, when x=0, then c=0, and when y=0, then c'=0; L represents a partial structure represented by the formula (ii); $L_2$ represents a linear, branched or cyclic divalent organic group having 2 to 30 carbon atoms; and the methylene group constituting $L_2$ may be substituted by an oxygen atom or a carbonyl group, and the hydrogen atom constituting the structure may be substituted by a hydroxyl group.

In this case, the partial structure represented by the formula (iv) is preferably a partial structure represented by the following formula (2), wherein $R^1$, a, b, a', b', c, d, c', d', x, y and L have the same meanings as defined above; $L_3$ represents a linear, branched or cyclic divalent organic group having 1 to 20 carbon atoms, $L_4$ represents $L_3$, the partial structure represented by the formula (i), or the partial structure represented by the formula (ii), and $0 \leq i \leq 1$, $0 \leq j \leq 1$ and i+j=1.

Furthermore, the compound for forming an organic film preferably contains a polymer having a partial structure represented by the following formula (vi),

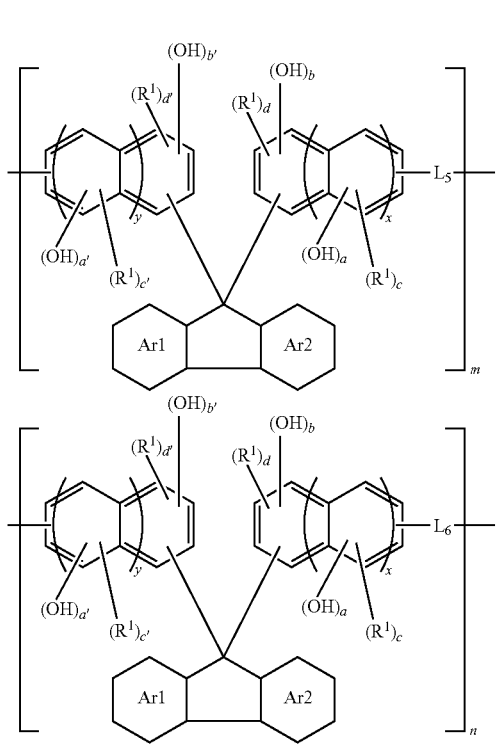

(vi)

wherein Ar1, Ar2, $R^1$, a, b, a', b', c, d, c', d', x and y have the same meanings as defined above; $L_5$ represents a linear, branched or cyclic divalent organic group having 1 to 20 carbon atoms, $L_6$ represents the partial structure represented by the formula (i) or the partial structure represented by the formula (ii), and $0 \leq m < 1$, $0 < n \leq 1$ and $m+n=1$.

Moreover, the compound for forming an organic film preferably contains a polymer having a partial structure represented by the following formula (vii),

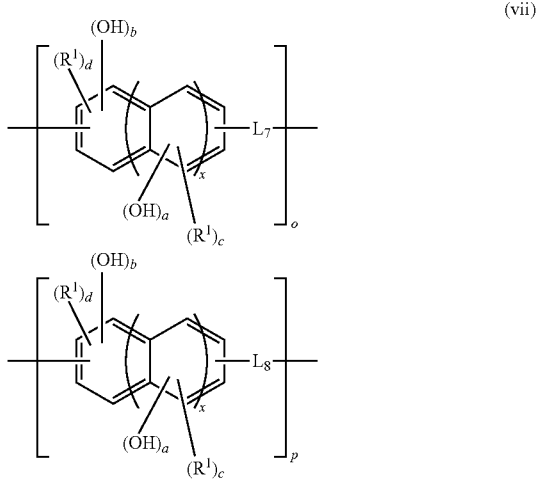

(vii)

wherein $R^1$, a, b, c, d and x have the same meanings as defined above; $L_7$ represents a linear, branched or cyclic divalent organic group having 1 to 20 carbon atoms, $L_8$ represents the partial structure represented by the formula (i) or the partial structure represented by the formula (ii), and $0 \leq o < 1$, $0 < p \leq 1$ and $o+p=1$.

These compounds have a plural number of the aromatic rings, have high carbon density, and show high dry etching resistance. Also, the $L_1$ contains an aliphatic hydrocarbon structure so that the compound contains high flexibility which contributes to improvement in filling/planarizing characteristics. As a result, both of etching characteristics and filling/planarizing characteristics can be satisfied.

By using such a compound for a resist underlayer film composition to be used for forming a multilayer resist film to be applied to a fine processing in the preparation step of a semiconductor apparatus, it is possible to provide a resist underlayer film composition for forming a resist underlayer film having high dry etching resistance as well as advanced filling/planarizing characteristics, a process for forming the resist underlayer film, and a patterning process. Also, it is also possible in the present invention to provide a planarizing composition for manufacturing a semiconductor apparatus having excellent filling/planarizing characteristics, which can be applied for planarizing in the preparation step of a semiconductor apparatus other than the multilayer resist process.

Also, it is provided an organic film composition using the compound for forming an organic film, which organic film composition comprises at least one selected from (A) the compound represented by the formula (iii), (B) the compound having the partial structure represented by the formula (iv), (C-1) the polymer compound having the partial structure represented by the formula (iv) as a part of the repeating unit, (C-2) the polymer compound having the partial structure represented by the formula (v), (C-3) the polymer compound having the partial structure represented by the formula (vi), and (C-4) the polymer compound having the partial structure represented by the formula (vii).

Such an organic film composition is suitable as an organic film composition for manufacturing a semiconductor apparatus. That is, it provides high dry etching resistance, and excellent filling/planarizing characteristics.

It is preferred that the organic film composition further contains (D) a resin containing an aromatic ring which is different from the (C-1) to (C-4).

By adding the (D) resin containing an aromatic ring to the organic film composition, various characteristics required for an organic film composition for manufacturing a semiconductor apparatus such as dry etching resistance, heat resistance and curability can be improved. Also, suitability of characteristics depending on the uses is possible by optionally selecting a resin to be added.

It is preferred that the (D) resin containing an aromatic ring contains a naphthalene ring.

When (D) the resin containing an aromatic ring in the organic film composition contains a naphthalene ring, it is possible to obtain an organic film excellent in etching resistance, heat resistance and optical characteristic.

Further, it is preferred that the (D) resin containing an aromatic ring contains a resin (D-1) obtained by a polycondensation reaction of at least one of compounds represented by the following formulae (3a) and (3b), with a compound represented by the following formula (4),

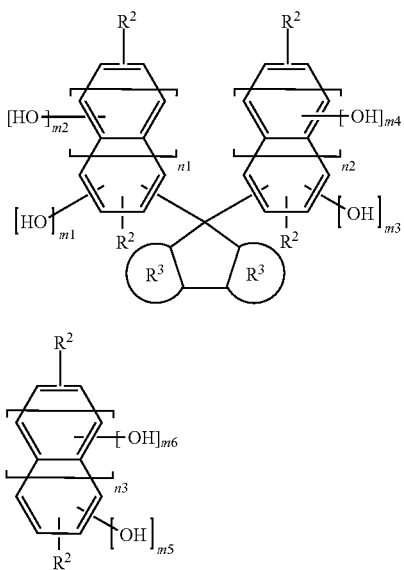

(3a)

(3b)

wherein each $R^2$ independently represent a hydrogen atom or a saturated or unsaturated hydrocarbon group having 1 to 20 carbon atoms; each $R^3$ independently represent a benzene ring or a naphthalene ring; m1+m2, m3+m4 and m5+m6 are each 1 or 2; and n1, n2 and n3 are each 0 or 1,

A-CHO  (4)

wherein A represents either one of a hydrogen atom, a hydrocarbon group having 1 to 10 carbon atoms and a substituted or unsubstituted aromatic hydrocarbon group having 6 to 20 carbon atoms.

When the organic film composition contains (D) the resin containing an aromatic ring including Compound (D-1), it is preferred since the formed organic film is excellent in filling/planarizing characteristics and particularly excellent in etching resistance and heat resistance.

Also, it is preferred that the (D) resin containing an aromatic ring contains (D-2) a resin having one or more repeating units represented by the following formula (5),

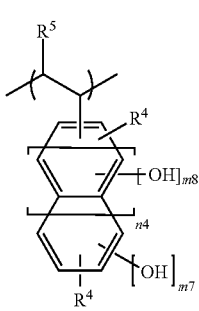

(5)

wherein each $R^4$ independently represent a hydrogen atom or a saturated or unsaturated hydrocarbon group having 1 to 20 carbon atoms; $R^5$ represent a hydrogen atom or may form a ring by bonding to one of $R^4$; when $R^4$ and $R^5$ are bonded to form a ring, —$R^4$—$R^5$— represents a single bond or an alkylene group having 1 to 3 carbon atoms; m7+m8 represents 0, 1 or 2; and n4 represents 0 or 1.

When the organic film composition contains (D) the resin containing an aromatic ring including Compound (D-2), it is preferred since the formed organic film is excellent in filling/planarizing characteristics, and particularly excellent in etching resistance and optical characteristic.

Also, the organic film composition may further contain at least one of (E) a compound containing a phenolic hydroxyl group, (F) an acid generator, (G) a cross-linking agent, (H) a surfactant, and (I) an organic solvent.

Thus, into the organic film composition, (E) a compound containing a phenolic hydroxyl group, (F) an acid generator and (G) a cross-linking agent can be added for further promoting a cross-linking reaction and (H) a surfactant can be also added for improving coatability in spin coating. Also, when (I) an organic solvent is added, the resulting organic film composition is a solution, so that spin coating can be carried out.

Also, the organic film composition can be made to be used for a resist underlayer film composition or a planarizing composition for manufacturing a semiconductor apparatus.

Thus, the organic film composition is used for forming a multilayer resist film to be applied to a fine processing in the preparation process of a semiconductor apparatus, it is possible to provide a resist underlayer film composition for forming a resist underlayer film having both of high dry etching resistance and advanced filling/planarizing characteristics. In addition it is possible to provide a planarizing composition for manufacturing a semiconductor apparatus having excellent filling/planarizing characteristics, which can be applied for planarizing in the preparation process of a semiconductor apparatus other than the multilayer resist process.

Also, the present invention provides a process for forming an organic film which is a process for preparing an organic film to be used as a resist underlayer film or a planarizing film for manufacturing a semiconductor apparatus of a multilayer resist film used in lithography, which comprises coating the organic film composition on a substrate to be processed, and subjecting the composition to heat treatment at a temperature of 100° C. or higher and 600° C. or lower for 10 seconds to 600 seconds to form a cured film.

Thus, by coating the organic film composition and subjecting the organic film composition to heat treatment at a temperature of 100° C. or higher and 600° C. or lower for 10 seconds to 600 seconds whereby the cross-linking reaction can be promoted and mixing with the upper layer film can be prevented.

Also, the present invention provides a process for forming an organic film which is a process for preparing an organic film to be used as a resist underlayer film or a planarizing film for manufacturing a semiconductor apparatus of a multilayer resist film used in lithography, which comprises coating the organic film composition on a substrate to be processed, and baking the composition in an atmosphere with an oxygen concentration of 0.1% or more and 21% or less to form a cured film.

The organic film composition is baked in such an oxygen atmosphere, thereby enabling to obtain a fully cured film.

Also, as the substrate to be processed, a substrate having a structural composition or step(s) each with a height of 30 nm or more can be used.

The organic film composition is excellent in filling/planarizing characteristics, so that it is particularly useful for forming a planarizing organic film on the substrate having a structural composition or step(s) each with a height of 30 nm or more.

Further, the present invention provides patterning process which is a process for forming a pattern on a substrate to be processed, which comprises the steps of, at least, forming a resist underlayer film on the substrate to be processed by using the organic film composition; forming a resist middle layer film on the resist underlayer film by using a resist middle layer film composition containing a silicon atom; forming a resist upper layer film on the resist middle layer film by using a resist upper layer film composition comprising a photoresist composition, to form a multilayer resist film; conducting exposure of a pattern circuit region of the resist upper layer film and then developing it by a developer to form a resist pattern on the resist upper layer film; etching the resist middle layer film by using the obtained pattern-formed resist upper layer film as an etching mask; etching the resist underlayer film by using the obtained pattern-formed resist middle layer film as an etching mask; and etching the substrate to be processed by using the obtained pattern-formed resist underlayer film as an etching mask, to form a pattern on the substrate to be processed.

In such a multilayer resist process, it is the patterning process using the organic film composition, a fine pattern can be formed to the substrate to be processed with high precision.

In addition, etching of the resist underlayer film using the obtained pattern-formed resist middle layer film as an etching mask can be carried out by using an etching gas mainly comprising an oxygen gas or a hydrogen gas.

The resist middle layer film containing a silicon atom shows etching resistance to an oxygen gas or a hydrogen gas, so that etching of the resist underlayer film by using the resist middle layer film as a mask can be carried out by using an etching gas mainly comprising an oxygen gas or a hydrogen gas.

Further, the present invention provides a patterning process which is a process for forming a pattern on the substrate to be processed, and comprises the steps of, at least, forming a resist underlayer film on the substrate to be processed by using the organic film composition; forming an inorganic hard mask middle layer film selected from any one of a silicon oxide film, a silicon nitride film and a silicon oxynitride film on the resist underlayer film; forming a resist upper layer film on the inorganic hard mask middle layer film by using a resist upper layer film composition comprising a photoresist composition, to make a multilayer resist film; conducting exposure of a pattern circuit region of the resist upper layer film and then developing it by a developer to form a resist pattern on the resist upper layer film; etching the inorganic hard mask middle layer film by using the obtained resist pattern as an etching mask; etching the resist underlayer film by using the obtained pattern-formed inorganic hard mask middle layer film as an etching mask; and etching the substrate to be processed by using the obtained pattern-formed resist underlayer film as an etching mask, to form a pattern on the substrate to be processed.

Moreover, the present invention is to provide a patterning process which is a process for forming a pattern on the substrate to be processed, which comprises the steps of, at least, forming a resist underlayer film on the substrate to be processed by using the organic film composition; forming an inorganic hard mask middle layer film selected from any one of a silicon oxide film, a silicon nitride film and a silicon oxynitride film on the resist underlayer film; forming an organic antireflection film on the inorganic hard mask middle layer film; forming a resist upper layer film on the organic antireflection film by using a resist upper layer film composition comprising a photoresist composition, to make a multilayer resist film; conducting exposure of a pattern circuit region of the resist upper layer film and then developing it by a developer to form a resist pattern on the resist upper layer film; etching the organic antireflection film and the inorganic hard mask middle layer film by using the obtained resist pattern as an etching mask; etching the resist underlayer film by using the obtained pattern-formed inorganic hard mask middle layer film as an etching mask; and etching the substrate to be processed by using the obtained pattern-formed resist underlayer film as an etching mask, to form a pattern on the substrate to be processed.

Thus, a resist middle layer film may be formed on a resist underlayer film, and an inorganic hard mask middle layer film selected from any one of a silicon nitride film and a silicon oxynitride film may be formed on the resist underlayer film. Further, a photoresist film may be formed on the inorganic hard mask middle layer film as a resist upper layer film, and an organic antireflection film (BARC: bottom-antireflective coating) is formed on the inorganic hard mask middle layer film by spin coating, and a photoresist film may be formed thereon. When a silicon oxynitride film (SiON film) is used as a middle layer film, it is enabled to restrict reflection by virtue of the two-layer antireflective films, i.e., the SiON film and BARC film, even by a liquid immersion exposure at a higher NA exceeding 1.0. Another merit of the formation of the BARC resides in obtainment of an effect to reduce footing of a photoresist pattern compared to a photoresist pattern just above the SiON film.

Further, the inorganic hard mask middle layer film can be formed by the CVD method or the ALD method.

In the patterning process, the inorganic hard mask middle layer film formed by the CVD method or the ALD method can be used in combination with the resist underlayer film formed by the spin coating method.

Also, as the substrate to be processed, a substrate having a structural composition or a step(s) each with a height of 30 nm or more can be used.

The organic film composition is excellent in filling/planarizing characteristics, so that it is particularly useful for forming a pattern on a substrate having a structural composition or step(s) each with a height of 30 nm or more by a multilayer resist process lithography.

As explained above, the organic film composition using the compound for forming an organic film a polymer compound containing the compound as a part of the repeating unit has excellent filling/planarizing characteristics as well as does not impair other characteristics such as etching resistance, so that it is extremely useful as, for example, a resist underlayer film composition for a multilayer resist process or a planarizing composition for manufacturing a semiconductor apparatus such as a silicon-containing two-layer resist process, a three-layer resist process using a silicon-containing middle layer film, and a four-layer resist process using a silicon-containing middle layer film and an organic antireflection film.

DETAILED DESCRIPTION OF THE PREFERRED EMBODIMENTS

Figure 1A:
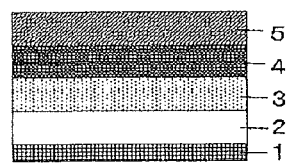
FIGS. 1A-1F are explanatory views of an example (three-layer resist process) of a patterning process using the present invention.

For realizing characteristics required for a resist underlayer film, in particular, characteristics such as etching resistance, heat resistance, and causing no occurrence of wiggling during etching of a substrate, a film having a high carbon atom density and a low hydrogen atom density is required. The present inventors have researched variously about a composition for an underlayer having a high carbon atom density and a low hydrogen atom density, and they have developed a biphenyl derivative represented by the following formula (6):

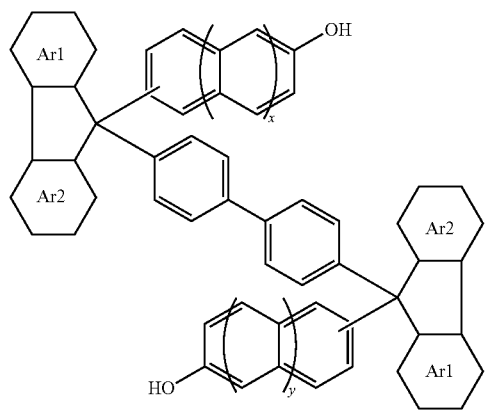

(6)

The biphenyl derivative has two fluorene structures and a phenol/naphthol structure in the molecule, has high carbon atom density (has low hydrogen atom density), and has excellent dry etching resistance. In addition, phenol/naphthol structures having a heat/acid cross-linking reactivity are effectively provided at the both ends of the molecule so that sufficient curability can be shown at the time of film formation.

Moreover, the present inventors thought to develop formulation components specialized in improvement of the characteristics by modifying the structure of the biphenyl derivative, to comply with the requirement to improve filling/planarizing characteristics that had been in demand in recent years. As a result, they have found out that advanced filling/planarizing characteristics have been realized by using a compound into which a structure having flexibility, that is, a partial structure represented by the following formula (i) or (ii) as a divalent organic group containing an aliphatic hydrocarbon group or a polyether group is introduced in place of a rigid biphenyl structure. And, the compound represented by the following formula (iii) which is a compound into which a partial structure represented by the following formula (i) or (ii) is introduced showed high dry etching resistance and sufficient curing reactivity at the time of an organic film as expected. Also, in the compound having a partial structure represented by the following formula (iv) which is based on the similar design as above, it has been found that high dry etching resistance and excellent filling/planarizing characteristics can be simultaneously realized, whereby they have accomplished the present invention.

In the following, the present invention is explained in more detail.

The most important structure possessed by the compound provided by the present invention is a partial structure represented by the following formula (i) or (ii),

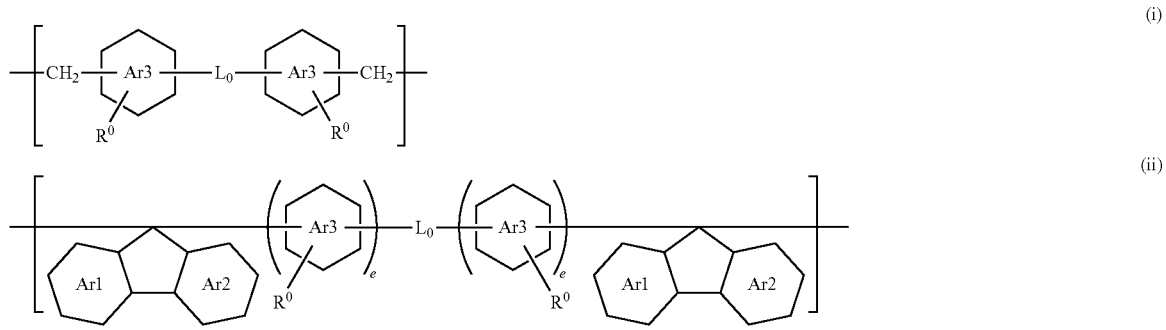

wherein the ring structures Ar1 and Ar2 each represents a benzene ring or a naphthalene ring; each and x and y independently represent 0 or 1.

wherein the ring structures Ar1, Ar2 and Ar3 each represent a substituted or unsubstituted benzene ring or naphthalene ring; e is 0 or 1; $R^0$ represents a hydrogen atom or a linear, branched or cyclic monovalent organic group having 1 to 30 carbon atoms; $L_0$ represents a linear, branched or cyclic divalent organic group having 1 to 32 carbon atoms; and the methylene group constituting $L_0$ may be substituted by an oxygen atom or a carbonyl group.

The compound for forming an organic film into which the structures are introduced has fluorene structures and a phenol/naphthol structure in the molecule, has high carbon atom density (has low hydrogen atom density), and has excellent dry etching resistance. In addition, phenol/naphthol structures having a heat/acid cross-linking reactivity are effectively provided at the both ends of the molecule so that sufficient curability can be shown at the time of film formation. Moreover, by incorporating an aliphatic hydrocarbon group having flexibility or a divalent organic group containing a polyether group, an organic film composition which shows advanced filling/planarizing characteristics, and has high dry etching resistance and excellent filling/planarizing characteristics can be obtained.

Ar3 in the formula (i) or (ii) represents a benzene ring or a naphthalene ring. Specifically the partial structures shown below may be preferably exemplified.

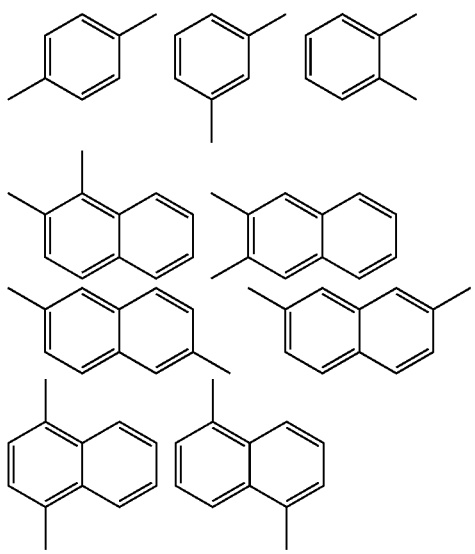

Ar3 may be substituted by a linear, branched or cyclic monovalent hydrocarbon group having 1 to 20 carbon atoms, and the methylene group constituting the monovalent hydrocarbon group may be substituted by an oxygen atom. The monovalent hydrocarbon group may be specifically exemplified by a methyl group, an ethyl group, an n-propyl group, an isopropyl group, an n-butyl group, a sec-butyl group, a tert-butyl group, an n-pentyl group, a neopentyl group, an n-hexyl group, an n-heptyl group, an n-octyl group, an n-nonyl group, an n-decyl group, an n-dodecyl group, an n-pentadecyl group, an n-eicosyl group, a cyclopentyl group, a cyclohexyl group, a cyclopentylmethyl group, a cyclohexylmethyl group, a cyclopentylethyl group, a cyclohexylethyl group, a cyclopentylbutyl group, a cyclohexylbutyl group and an adamantyl group.

By introducing Ar3, dry etching resistance can be improved. Also, as compared with the case where, as $L_0$ of the compound represented by the formula (i) or (ii), for example, a polymethylene group, etc., is introduced and made e=0, there is a superior point in synthesis that a by-product(s) difficultly formed.

Ar1 and Ar2 in the formula (ii) each represents a benzene ring or a naphthalene ring.

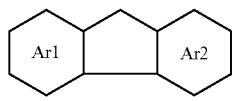

A fluorine ring structure and a benzofluorene structure are particularly preferred as the partial structure. In addition, the hydrogen atom in these groups may be substituted by a halogen atom, a hydrocarbon group, a hydroxyl group, an alkoxy group, a nitro group or a cyano group. Specific partial structures are exemplified below.

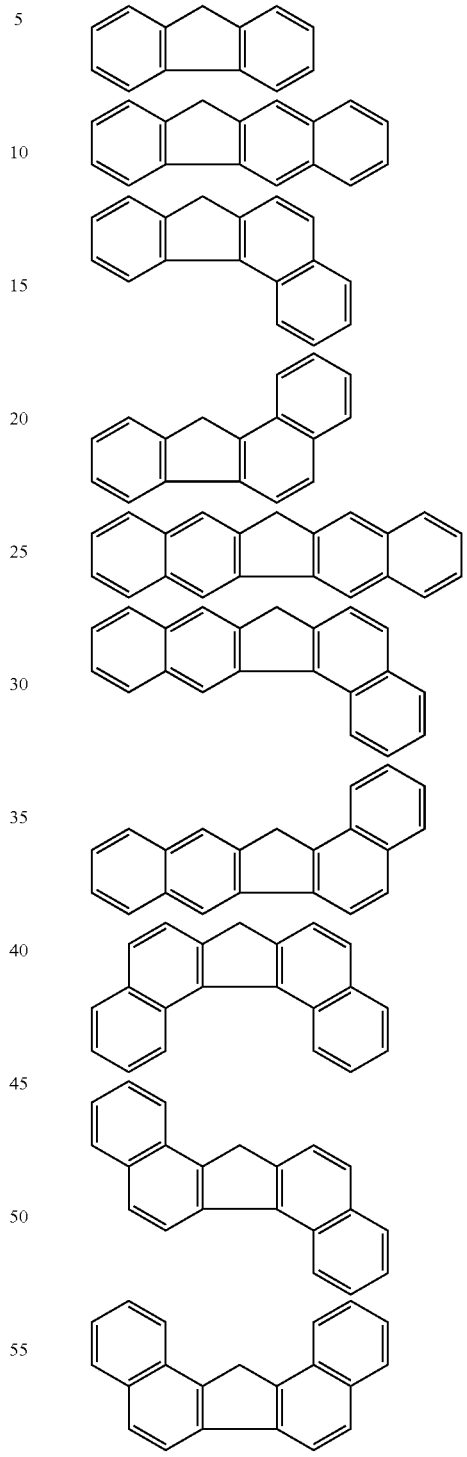

$R_0$ in the formula (i) or (ii) represents a linear, branched or cyclic monovalent hydrocarbon group having 1 to 20 carbon atoms, and the methylene group constituting the may hydrocarbon group be substituted by an oxygen atom. The monovalent hydrocarbon group may be specifically exemplified by a methyl group, an ethyl group, an n-propyl group, an isopropyl group, an n-butyl group, a sec-butyl group, a tert-butyl group, an n-pentyl group, a neopentyl group, an n-hexyl group, an n-heptyl group, an n-octyl group, an n-nonyl group, an n-decyl group, an n-dodecyl group, an n-pentadecyl group, an n-eicosyl group, a cyclopentyl group, a cyclohexyl group, cyclopentylmethyl group, a cyclohexylmethyl group, a cyclopentylethyl group, a cyclohexylethyl group, a cyclopentylbutyl group, a cyclohexylbutyl group, an adamantyl group, a methoxy group, an ethoxy group, a propoxy group, a butoxy group, a pentoxy group, a hexyloxy group, a heptoxy group, a methoxyethoxy group and an ethoxyethoxy group.

$L_0$ in the formula (i) or (ii) represents a linear, branched or cyclic divalent organic group having 1 to 32 carbon atoms; and the methylene group constituting it may be substituted by an oxygen atom or a carbonyl group. Such a divalent organic group may be specifically exemplified by the following.

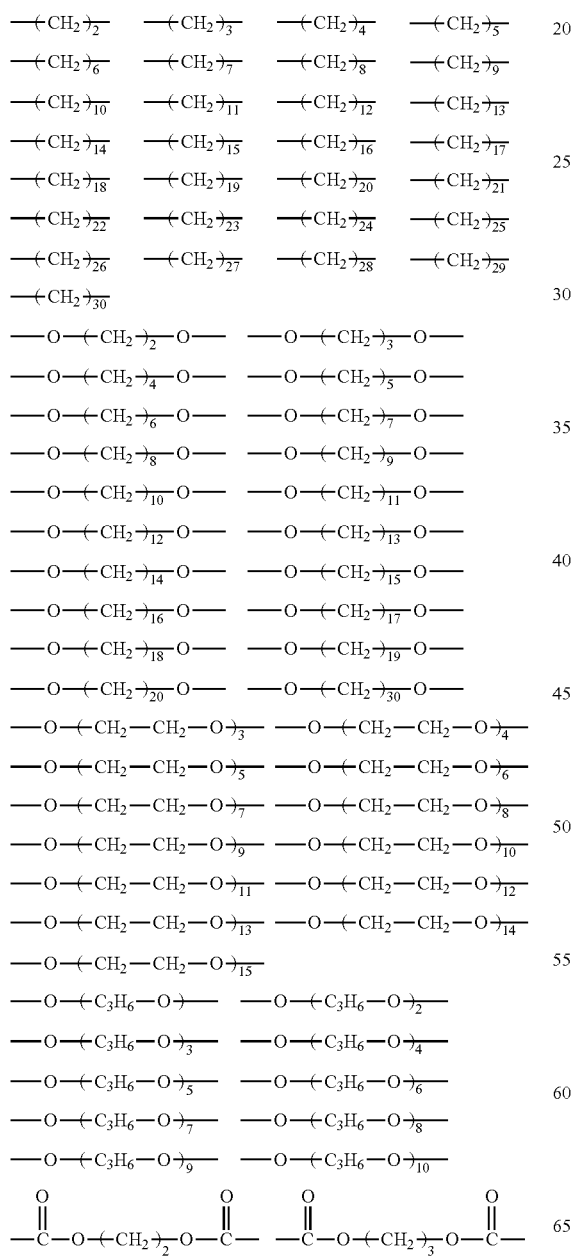
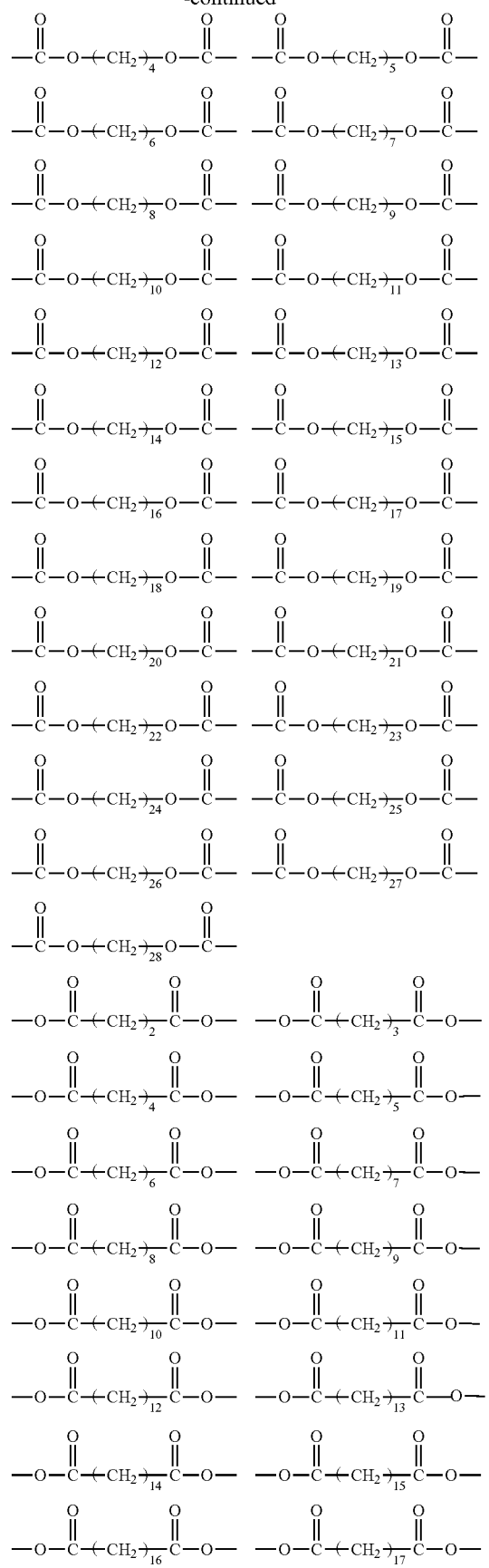

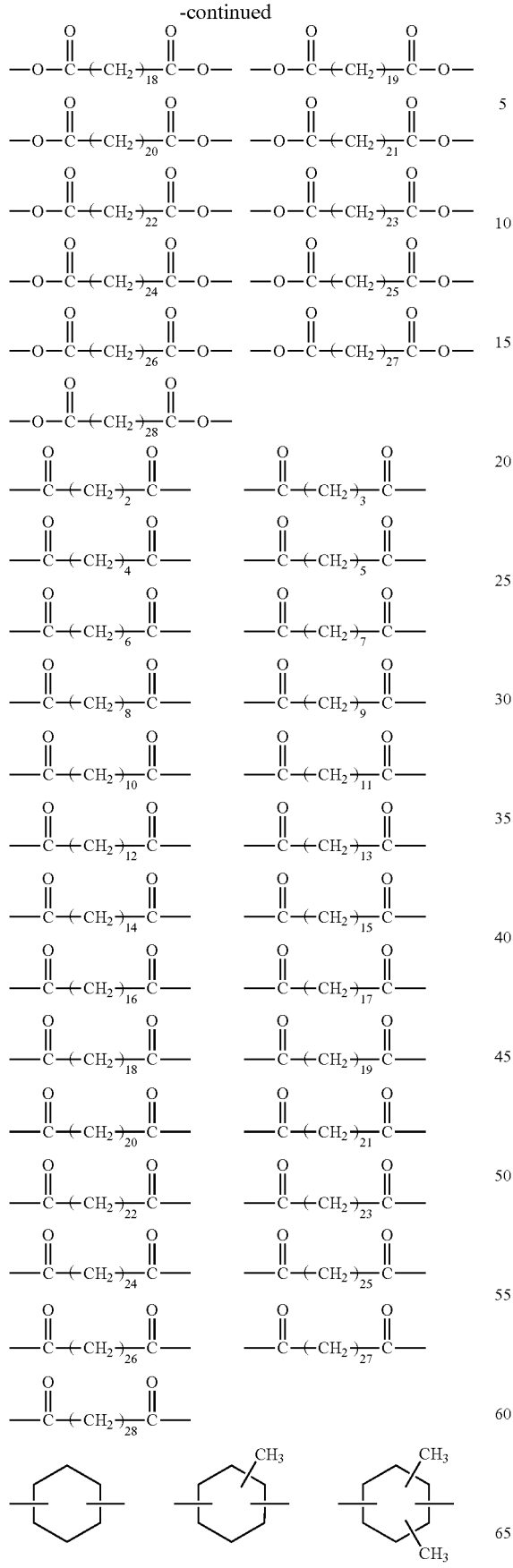
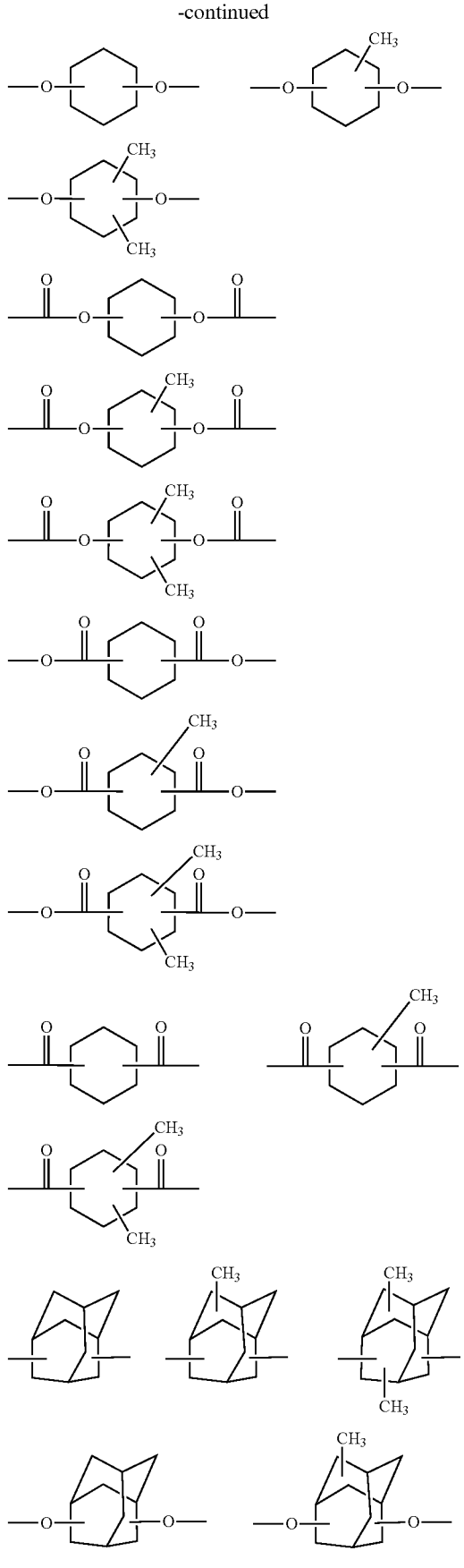

-continued

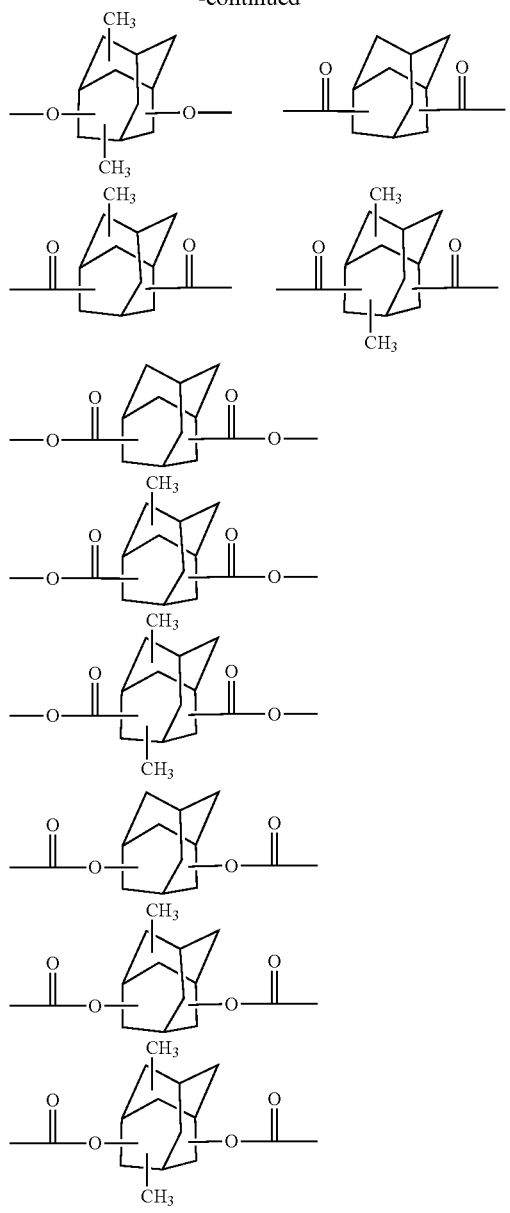

Next, as a process for preparing the partial structure represented by the formula (i), the methods shown by the following reaction schemes are exemplified,

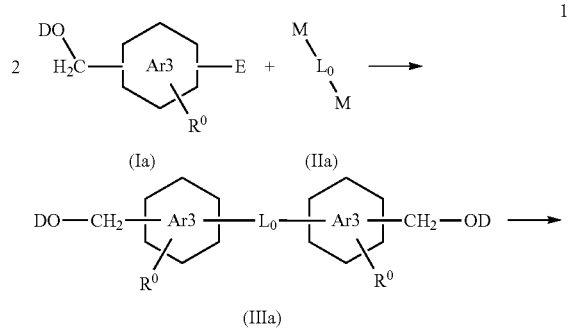

-continued

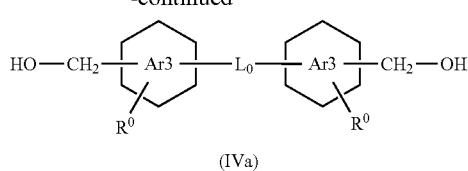

(IVa)

wherein D represents a protective group for an alcohol against an organometal; E represents an eliminatable group on the aromatic ring to an organometallic reagent; M represents Li or MgX, where X represents a halogen atom; and $L_0$, $R^0$ and Ar3 have the same meanings as defined above.

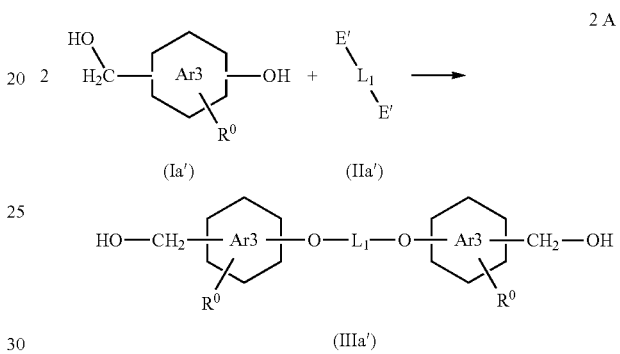

wherein E' represents an eliminatable group which eliminates with the hydroxyl group by an etherification reaction; $L_1$ represents a linear, branched or cyclic divalent hydrocarbon group having 2 to 30 carbon atoms containing an aliphatic hydrocarbon group; and $R^0$ and Ar3 have the same meanings as defined above.

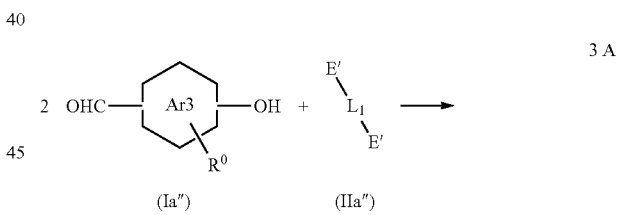

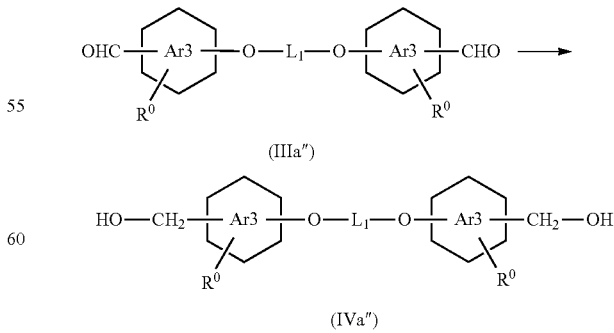

wherein E', $L_1$, $R^0$ and Ar3 have the same meanings as defined above.

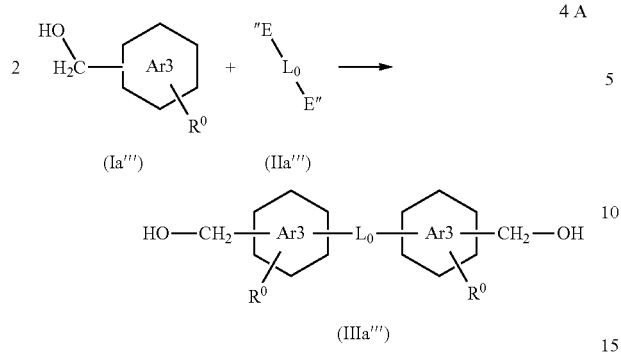

4A (Ia''')  (IIa''')  (IIIa''')

wherein E" represents an eliminatable group to the aromatic electrophilic reagent in the Friedel-Crafts reaction; and $L_0$, $R^0$ and Ar3 have the same meanings as defined above.

Next, as a process for preparing the partial structure represented by the formula (ii), the methods shown by the following reaction schemes 1B and 2B are exemplified,

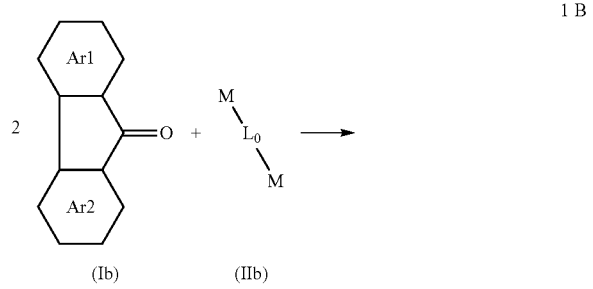

1B (Ib)  (IIb)

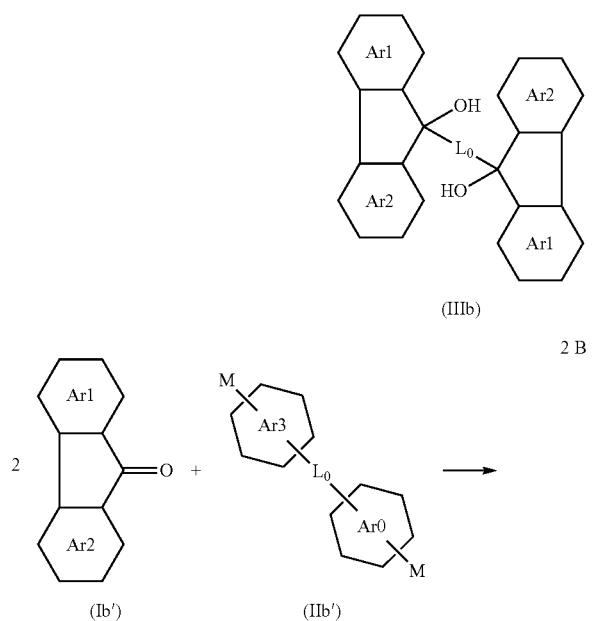

(IIIb)

2B (Ib')  (IIb')

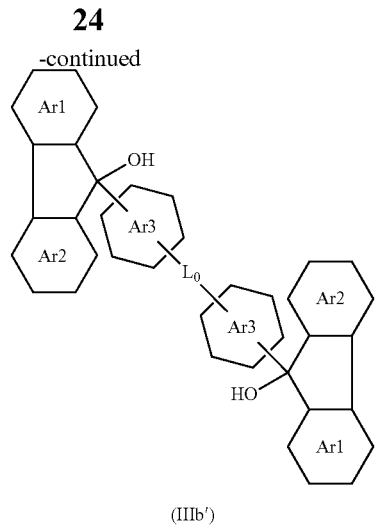

(IIIb')

wherein Ar1, Ar2, Ar3, $L_0$ and M have the same meanings as defined above.

As the organometallic reagent to be used in the reaction scheme 1A, Grignard reagents, organolithium reagents, organozinc reagents and organotitanium reagents are exemplified, and Grignard reagents and organolithium reagents are particularly preferred. The Grignard reagent and the organolithium reagent may be prepared by direct metallation of a corresponding halide and metal magnesium or metal lithium, or may be formed by a metal-halogen exchange reaction with an isopropyl magnesium halide or an aliphatic organometallic compound such as methyl lithium and butyl lithium. Also, the organozinc reagent or the organotitanium reagent can be prepared from a corresponding Grignard reagent or organolithium reagent by the reaction with a zinc halide, a titanium(IV) halide or a titanium(IV) alkoxide. At the time of preparing the organometallic reagent (1A-IIa), or at the time of reacting the organometallic reagent and the aromatic compound (1A-Ia), a metal salt compound may be co-presented. At this time, the reaction proceeds smoothly by the presence of a transition metal catalyst such as palladium and nickel. The metal salt compound may be mentioned a cyanide, a halide and a perhalogenic acid salt, and particularly a lithium salt such as lithium chloride, lithium bromide, lithium iodide and lithium perchlorate, and a copper salt such as copper(I) cyanide, copper(II) cyanide, copper(I) chloride, copper(II) chloride and dilithium tetrachlorocuprate are preferably exemplified. The metal salt compound is added in an amount of 0.01 to 5.0 equivalents, preferably 0.2 to 2.0 equivalents based on an amount of the organometallic reagent, whereby the solubility of the organometallic reagent is increased to make it easily prepared, and, nucleophilicity or Lewis acidity of the reagent can be controlled. The solvent to be used for preparing the organometallic reagent (1A-IIa) and in the reaction with the aromatic compound (1A-Ia) may be mentioned an ether such as diethyl ether, dibutyl ether, tetrahydrofuran, 1,4-dioxane and cyclopentyl methyl ether; a hydrocarbon such as benzene, toluene, xylene, mesitylene, hexane, heptane, octane and isooctane; an aprotic polar solvent such as N,N,N',N'-tetramethylethylenediamine, hexamethylphosphoric triamide and N,N-dimethylformamide, singly or in admixture. The reaction temperature may vary depending on a kind of the aromatic compound (1A-Ia) or the organometallic reagent (1A-IIa) and reaction conditions, and preferably −70 to 150° C. For example, in the case of an organozinc reagent or a Grignard reagent as (1A-IIa), it can be variously selected from room temperature to under reflux at the boiling point of the solvent. The reaction time is desirably determined by tracing the reaction using chromatography to complete the reaction, and it is generally carried out from 30 minutes to 48 hours.

As the protective group for an alcohol to be used in the reaction scheme 1A, those generally known may be used, and an acetal group or a silyl group is preferred.

As the organometallic reagent to be used in the reaction schemes 1B and 2B, Grignard reagents, organolithium reagents, organozinc reagents and organotitanium reagents are exemplified, and Grignard reagents and organolithium reagents are particularly preferred. The Grignard reagent and the organolithium reagent may be prepared by direct metallation of a corresponding halide and metal magnesium or metal lithium, or may be formed by a metal-halogen exchange reaction with an isopropyl magnesium halide or an aliphatic organometallic compound such as methyl lithium and butyl lithium. Also, the organozinc reagent or the organotitanium reagent can be prepared from a corresponding Grignard reagent or organolithium reagent by the reaction with a zinc halide, a titanium(IV) halide or a titanium (IV) alkoxide. At the time of preparing the organometallic reagent (1B-IIb) or (2B-IIb'), or at the time of reacting the organometallic reagent and the ketone compound (1B-Ib, 2B-Ib'), a metal salt compound may be co-presented. The metal salt compound may be mentioned a cyanide, a halide and a perhalogenic acid salt, and particularly a lithium salt such as lithium chloride, lithium bromide, lithium iodide and lithium perchlorate, and a copper salt such as copper(I) cyanide, copper(II) cyanide, copper(I) chloride, copper(II) chloride and dilithium tetrachlorocuprate are preferably exemplified. The metal salt compound is added in an amount of 0.01 to 5.0 equivalents, preferably 0.2 to 2.0 equivalents based on an amount of the organometallic reagent, whereby the solubility of the organometallic reagent is increased to make it easily prepared, and, nucleophilicity or Lewis acidity of the reagent can be controlled. The solvent to be used for preparing the organometallic reagent (1B-IIb) or (2B-IIb') and in the reaction with the ketone compound (1B-Ib, 2B-Ib') may be mentioned an ether such as diethyl ether, dibutyl ether, tetrahydrofuran, 1,4-dioxane and cyclopentyl methyl ether; a hydrocarbon such as benzene, toluene, xylene, mesitylene, hexane, heptane, octane and isooctane; an aprotic polar solvent such as N,N,N',N'-tetramethylethylenediamine, hexamethylphosphoric triamide and N,N-dimethylformamide, singly or in admixture. The reaction temperature may vary depending on a kind of the ketone compound (1B-Ib, 2B-Ib') or the organometallic reagent (1B-IIb) or (2B-IIb') and reaction conditions, and, for example, in the case of an organolithium reagent as (1B-IIb) or (2B-IIb'), it is −70 to 0° C. and in the case of a Grignard reagent, it can be variously selected from room temperature to under reflux at the boiling point of the solvent. The reaction time is desirably determined by tracing the reaction using chromatography to complete the reaction, and it is generally carried out from 30 minutes to 48 hours.

As an example of the reaction of the reaction scheme 2A, P1) condensation reaction with an organic halogen compound and
P2) condensation reaction with a polyol are mentioned below specifically.
P1) Condensation Reaction with an Organic Halogen Compound The condensation reaction of the aromatic compound (2A-Ia') and the organic halogen compound is generally carried out in the absence of a solvent or in a solvent at room temperature, or under cooling or under heating, if necessary.

The organic halogen compound may be specifically exemplified by a dihaloalkane such as 1,2-dichloroethane, 1,2-dibromoethane, 1,3-dichloropropane, 1,3-dibromopropane, 1,3-diiodopropane, 1,4-dichlorobutane, 1,4-dibromobutane, 1-bromo-4-chlorobutane, 1,4-diiodobutane, 1,5-dichloropentane, 1,5-dibromopentane, 1,5-diiodopentane, 1,6-dichlorohexane, 1,6-dibromohexane, 1-bromo-6-chlorohexane, 1,6-diiodohexane, 1,7-dibromoheptane, 1,8-dibromooctane, 1,9-dibromononane, 1,10-dibromodecane, 1,12-dibromododecane, α,α'-dibromo-m-xylene, α,α'-dibromo-o-xylene, α,α'-dibromo-p-xylene, 2,5-bromomethylnaphthalene, 2,6-bromomethylnaphthalene, 2,7-bromomethylnaphthalene and 1,8-bromomethylnaphthalene; an epihalohydrin such as epifluorohydrin, epichlorohydrin, epibromohydrin, epiiodohydrin and β-methylepichlorohydrin, but the invention is not limited by these. These organic halogen compounds may be used alone or may be used in combination of two or more kinds.

An amount of the organic halogen compound is preferably 0.05 to 5 mol, more preferably 0.1 to 1.5 mol based on 1 mol of the compound represented by the formula (I).

The condensation reaction with the organic halogen compound is preferably carried out under basic conditions. The base to be used may be exemplified by an inorganic base such as sodium hydroxide, potassium hydroxide, barium hydroxide, sodium carbonate, sodium hydrogen carbonate, potassium carbonate, lithium hydride, sodium hydride, potassium hydride and calcium hydride; an alkyl metal such as methyl lithium, n-butyl lithium, methylmagnesium chloride and ethylmagnesium bromide; an alkoxide such as sodium methoxide, sodium ethoxide and potassium t-butoxide; and an organic base such as triethylamine, diisopropylethylamine, N,N-dimethylaniline, pyridine and 4-dimethylaminopyridine. An amount of the base to be used is preferably 1.0 to 5.0 mol, more preferably 2.0 to 3.0 mol based on 1 mol of the compound represented by the formula (I). As the method of the reaction, there is a method in which the compound represented by the formula (I), the organic halogen compound and a base are charged at once, or a method in which an optional component is added dropwise. The base or metal impurities can be removed by the usual aqueous post-treatment. As others, by adding a poor solvent and separating the poor solvent layer, starting composition(s) or low molecular weight polymer fraction(s) can be removed. Moreover, if necessary, an amount of the metal impurities can be reduced by passing through a metal-removing filter. These purification treatments may be carried out singly or may be carried out in combination of two or more kinds.

The solvent to be used in the condensation reaction may be exemplified by an ether such as diethyl ether, dibutyl ether, diethylene glycol diethyl ether, diethylene glycol dimethyl ether, tetrahydrofuran and 1,4-dioxane; a chlorine solvent such as methylene chloride, chloroform, dichloroethane and trichloroethylene; a hydrocarbon such as hexane, heptane, benzene, toluene, xylene and cumene; a nitrile such as acetonitrile; a ketone such as acetone, ethyl methyl ketone and isobutyl methyl ketone; an ester such as ethyl acetate, n-butyl acetate and propylene glycol methyl ether acetate; and an aprotic polar solvent such as dimethylsulfoxide, N,N-dimethylformamide, hexamethylphosphoric triamide and N-methyl-2-pyrrolidone, and these may be used alone or may be used in combination of two or more kinds. The reaction may be carried out by two-layer using the organic solvent and water, and in this case, to proceed the reaction rapidly, there may be added a phase-transfer catalyst such as tetramethylammonium chloride, tetraethylammonium bromide, tetraethylammonium chloride, tetrapropylammonium bromide, tetrapropylammonium hydroxide, tetrabutylammonium bromide, tetrabutylammonium hydroxide, tetrabutylammonium hydrogen sulfate, tributylmethylammonium chloride, trioctylmethylammonium chloride, trilaurylmethylammonium chloride, benzyltrimethylammonium chloride, benzyltrimethylammonium hydroxide, benzyltriethylammonium chloride, benzyltributylammonium chloride and phenyltrimethylammonium chloride.

A reaction temperature of the condensation reaction is preferably from −50° C. to the boiling point of the solvent, more preferably room temperature to 150° C.

P2) Condensation Reaction with a Polyol

The condensation reaction of the aromatic compound (2A-Ia') and a polyol is generally carried out in the absence of a solvent or in a solvent, at room temperature or under cooling or under heating, if necessary.

The polyol may be exemplified by ethylene glycol, polyethylene glycol such as diethylene glycol, triethylene glycol, tetraethylene glycol, pentaethylene glycol and hexaethylene glycol; propylene glycol, and glycerin, but the invention is not limited by these. These polyols may be used alone or may be used in combination of two or more kinds.

An amount of the polyol to be used is preferably 0.1 to 10.0 mol, more preferably 0.3 to 5.0 mol based on 1 mol of the compound represented by the formula (I).

In the condensation reaction, a catalyst may be used. An acid catalyst is particularly preferred. The acid catalyst which can be used may be mentioned an inorganic acid such as hydrochloric acid, hydrobromic acid, nitric acid, sulfuric acid, formic acid, phosphoric acid and heteropoly acid; an organic acid such as oxalic acid, acetic acid, trifluoroacetic acid, methanesulfonic acid, benzenesulfonic acid, p-toluenesulfonic acid and trifluoromethanesulfonic acid; and a Lewis acid such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide and titanium(IV) oxide. More specifically, there may be mentioned an acid catalyst such as hydrochloric acid, nitric acid, sulfuric acid, formic acid, oxalic acid, acetic acid, methanesulfonic acid, camphorsulfonic acid, p-toluenesulfonic acid and trifluoromethanesulfonic acid. An amount of these acid catalysts is preferably 0.1 to 50.0 mol based on 1 mol of the compound represented by the formula (I). As the method of the reaction, there is a method in which the compound represented by the formula (I), a polyol and a catalyst are charged at once, or a method in which an optional component is added dropwise. After completion of the reaction, to remove unreacted starting composition(s) or a catalyst existing in the reaction system, a temperature of the reaction vessel is raised to 130 to 230° C., and a volatile component(s) can be removed at 1 to 50 mmHg. The catalyst or metal impurities can be removed by the usual aqueous post-treatment. As others, by adding a poor solvent and separating the poor solvent layer, starting composition(s) or low molecular weight polymer fraction(s) can be removed. Moreover, if necessary, an amount of the metal impurities can be reduced by passing through a metal-removing filter. These purification treatments may be carried out singly or may be carried out in combination of two or more kinds.

The solvent to be used in the condensation reaction may be exemplified by an alcohol such as methanol, ethanol, isopropyl alcohol, butanol, ethylene glycol, propylene glycol, diethylene glycol and glycerol; an ether such as ethylene glycol monomethyl ether, propylene glycol monomethyl ether, diethyl ether, dibutyl ether, diethylene glycol diethyl ether, diethylene glycol dimethyl ether, tetrahydrofuran and 1,4-dioxane; a chlorine solvent such as methylene chloride, chloroform, dichloroethane and trichloroethylene; a hydrocarbon such as hexane, heptane, benzene, toluene, xylene and cumene; a nitrile such as acetonitrile; a ketone such as acetone, ethyl methyl ketone and isobutyl methyl ketone; an ester such as ethyl acetate, n-butyl acetate and propylene glycol methyl ether acetate; and an aprotic polar solvent such as dimethylsulfoxide, N,N-dimethylformamide and hexamethylphosphoric triamide, and these may be used alone or may be used in combination of two or more kinds.

A reaction temperature of the condensation reaction is preferably from −50° C. to the boiling point of the solvent, more preferably room temperature to 150° C.

In the reaction scheme 3A, the objective composition can be obtained by reducing the formyl group contained in the ether compound prepared by the reaction scheme 2A.

As the reducing agent, a generally known compound such as sodium boronhydride and lithium aluminum hydride can be used. A reaction temperature is possible between −70° C. and 150° C., and it is optionally selectable in view of a reaction rate or the like.

The solvent to be used may be mentioned an ether such as diethyl ether, dibutyl ether, tetrahydrofuran, 1,4-dioxane and cyclopentyl methyl ether; a hydrocarbon such as benzene, toluene, xylene, mesitylene, hexane, heptane, octane and isooctane; an aprotic polar solvent such as N,N,N',N'-tetramethylethylenediamine, hexamethylphosphoric triamide and N,N-dimethylformamide, singly or in admixture.

As an example of the reaction according to the reaction scheme 4A, there may be exemplified acylation according to an aromatic electrophilic substitution reaction of a Lewis acid and an acid halide. This substitution reaction is generally carried out in the absence of a solvent or in a solvent at room temperature, or under cooling or under heating, if necessary.

As the Lewis acid, those generally known such as boron trifluoride, aluminum trichloride and iron trichloride can be used. As the acid halide to be used, there may be exemplified by succinyl chloride and adipoyl chloride. The solvent may be exemplified by a halogenated hydrocarbon such as carbon disulfide, dichloromethane, chloroform, carbon tetrachloride and dichloroethylene; and nitrobenzene.

These compounds can be used not only as a preparation intermediate of the compound for forming an organic film, but also, by further acting on the obtained compound for forming an organic film, to form a polymer, whereby an organic film composition can be formed.

In the present invention, a compound represented by the following formula (iii) utilizing a partial structure represented by the formula (ii) obtained as mentioned above can be used.

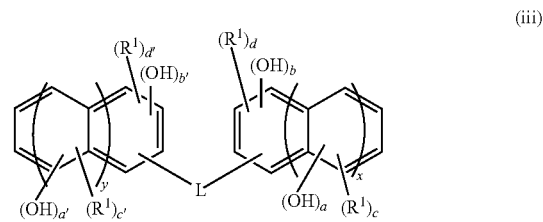

(iii)

wherein the ring structures Ar1, Ar2 and Ar3 each represent a substituted or unsubstituted benzene ring or naphthalene ring; $R^1$ represents a linear, branched or cyclic monovalent hydrocarbon group having 1 to 20 carbon atoms, the methylene group constituting $R^1$ may be substituted by an oxygen atom; a+b and a'+b' are each independently 1, 2 or 3; c, d, c' and d' are each independently 0, 1 or 2; x and y each independently represent 0 or 1, when x=0, then a=c=0, and when y=0, then a'=c'=0; e is 0 or 1; and L represents a partial structure represented by the formula (ii).

The compound for forming an organic film represented by the formula (iii) has fluorene structures and a phenol/naphthol structure in the molecule, has high carbon atom density (has low hydrogen atom density), and has excellent dry etching resistance. In addition, phenol/naphthol structures having a heat/acid cross-linking reactivity are effectively provided at the both ends of the molecule so that sufficient curability can be shown at the time of film formation. Moreover, by introducing an aliphatic hydrocarbon group having flexibility and a divalent organic group containing a polyether group in place of a rigid biphenyl structure, an organic film composition showing advanced filling/planarizing characteristics and having high dry etching resistance and excellent filling/planarizing characteristics is provided.

Each x and y in the partial structure of the formula (iii) independently represent 0 or 1. Also, a+b and a'+b' are each independently 1, 2 or 3. c, d, c' and d' are each independently 0, 1 or 2. When x=0, then, a=c=0, and when y=0, then, a'=c'=0.

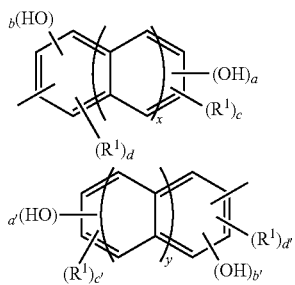

The partial structure may be preferably exemplified by the following structures (the dotted line represents a bonding arm.).

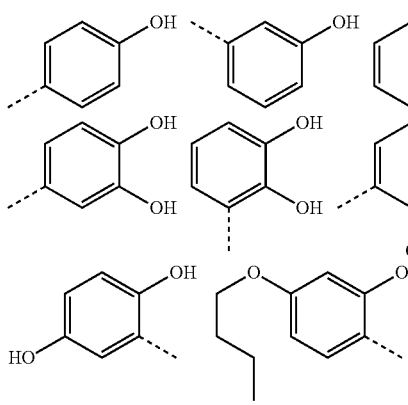

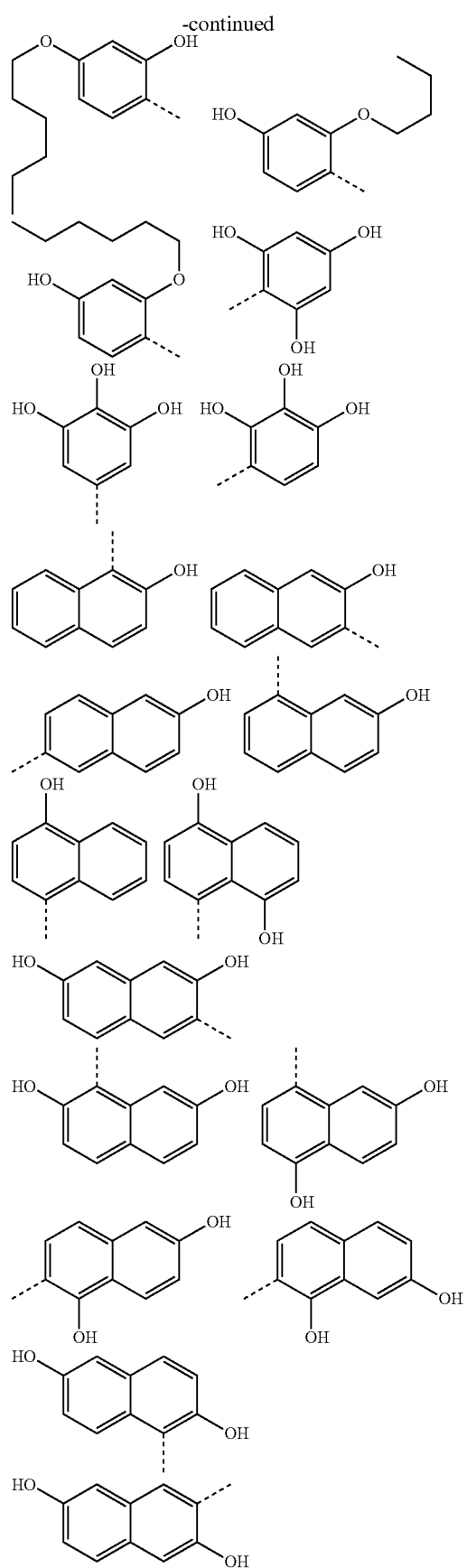

R¹ in the formula (iii) represents a linear, branched or cyclic monovalent hydrocarbon group having 1 to 20 carbon atoms, and the methylene group constituting the same may be substituted by an oxygen atom. The monovalent hydrocarbon group may be specifically exemplified by a methyl group, an ethyl group, an n-propyl group, an isopropyl group, an n-butyl group, a sec-butyl group, a tert-butyl group, an n-pentyl group, a neopentyl group, an n-hexyl group, an n-heptyl group, an n-octyl group, an n-nonyl group, an n-decyl group, an n-dodecyl group, an n-pentadecyl group, an n-eicosyl group, a cyclopentyl group, a cyclohexyl group, a cyclopentylmethyl group, a cyclohexylmethyl group, a cyclopentylethyl group, a cyclohexylethyl group, a cyclopentylbutyl group, a cyclohexylbutyl group and an adamantyl group.

As a preferred form of the compound represented by the formula (iii), a compound containing an aliphatic hydrocarbon group represented by the following formula (1) may be mentioned.

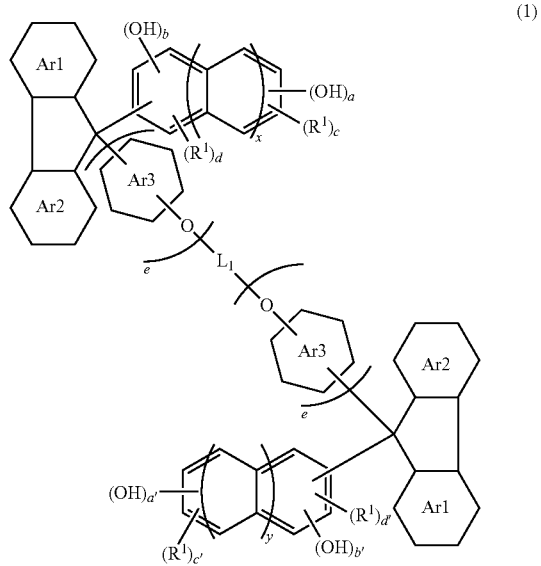

(1)

wherein the ring structures Ar1, Ar2 and Ar3 each represent a substituted or unsubstituted benzene ring or naphthalene ring; R¹ represents a linear, branched or cyclic monovalent hydrocarbon group having 1 to 20 carbon atoms, the methylene group constituting R¹ may be substituted by an oxygen atom; a+b and a'+b' are each independently 1, 2 or 3; c, d, c' and d' are each independently 0, 1 or 2; x and y each independently represent 0 or 1, when x=0, then a=c=0, and when y=0, then a'=c'=0; e is 0 or 1; $L_1$ represents a linear, branched or cyclic divalent hydrocarbon group having 2 to 30 carbon atoms containing an aliphatic hydrocarbon group, and the methylene group constituting $L_1$ may be substituted by an oxygen atom or a carbonyl group.

The compound containing an aliphatic hydrocarbon group represented by the formula (1) has two fluorene structures and a phenol/naphthol structure in the molecule, has high carbon atom density (has low hydrogen atom density), and has excellent dry etching resistance. In addition, phenol/naphthol structures having a heat/acid cross-linking reactivity are effectively provided at the both ends of the molecule so that sufficient curability can be shown at the time of film formation. Moreover, by introducing a divalent hydrocarbon group containing an aliphatic hydrocarbon group having flexibility in place of a rigid biphenyl structure, an organic film composition showing advanced filling/planarizing characteristics, and having high dry etching resistance and excellent filling/planarizing characteristics is provided.

$L_1$ in the formula (1) represents a linear, branched or cyclic divalent hydrocarbon group having 2 to 30 carbon atoms containing an aliphatic hydrocarbon group, and the methylene group constituting the same may be substituted by an oxygen atom or a carbonyl group. The divalent hydrocarbon group may be specifically exemplified by a group in which two hydrogen atoms are removed from ethane, propane, propylene, n-butane, 1-butene, 2-butene, isobutane, n-pentane, n-hexane, n-heptane, n-octane, n-nonane, n-decane, n-dodecane, n-eicosane, n-triacontane, 1,4-dimethylcyclohexane, 1,3-dimethyladamantane, o-xylene, m-xylene, p-xylene, 2,5-dibutyl-p-xylene, 2,5-dibutoxy-p-xylene, 2,5-dioctyl-p-xylene, 2,5-dioctyloxy-p-xylene, 1,4-dimethylnaphthalene, 1,5-dimethylnaphthalene, 2,6-dimethylnaphthalene and 2,7-dimethylnaphthalene.

More preferred form of the compound represented by the formula (iii) may be mentioned a compound represented by the following formula (7),

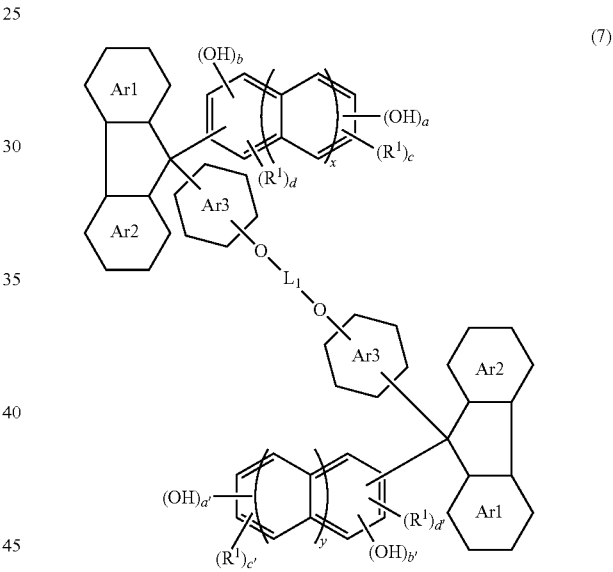

(7)

wherein the ring structures Ar1, Ar2 and Ar3 each represent a substituted or unsubstituted benzene ring or naphthalene ring; R¹ represents a linear, branched or cyclic monovalent hydrocarbon group having 1 to 20 carbon atoms, R¹ and the methylene group constituting the same may be substituted by an oxygen atom; a+b and a'+b' are each independently 1, 2 or 3; c, d, c' and d' are each independently 0, 1 or 2; x and y each independently represent 0 or 1, when x=0, then a=c=0, and when y=0, then a'=c'=0; $L_1$ represents a linear, branched or cyclic divalent hydrocarbon group having 2 to 30 carbon atoms containing an aliphatic hydrocarbon group, and the methylene group constituting $L_1$ may be substituted by an oxygen atom or a carbonyl group.

As a typical example in the preparation process of the compound represented by the formula (7) (e=1) or (8) (e=0) which is an example of the formula (1), there is a route in which an intermediate product (11) (above-mentioned IIIb') or (13) (above-mentioned IIIb) is obtained by the addition reaction of an organometallic reagent (10) (above-mentioned IIb') or (12) (above-mentioned IIb) to the following ketone compound (9) (above-mentioned Ib and Ib'), and a phenol or naphthol analogues is/are reacted thereto to obtain (7) or (8), but the preparation method of the compound is not limited by the method. In the case of the following method, the organometallic reagent (10) or (12) is preferably used in an amount of 0.1 to 20 mol, particularly 0.25 to 0.5 mol based on 1 mol of the ketone compound of the formula (9),

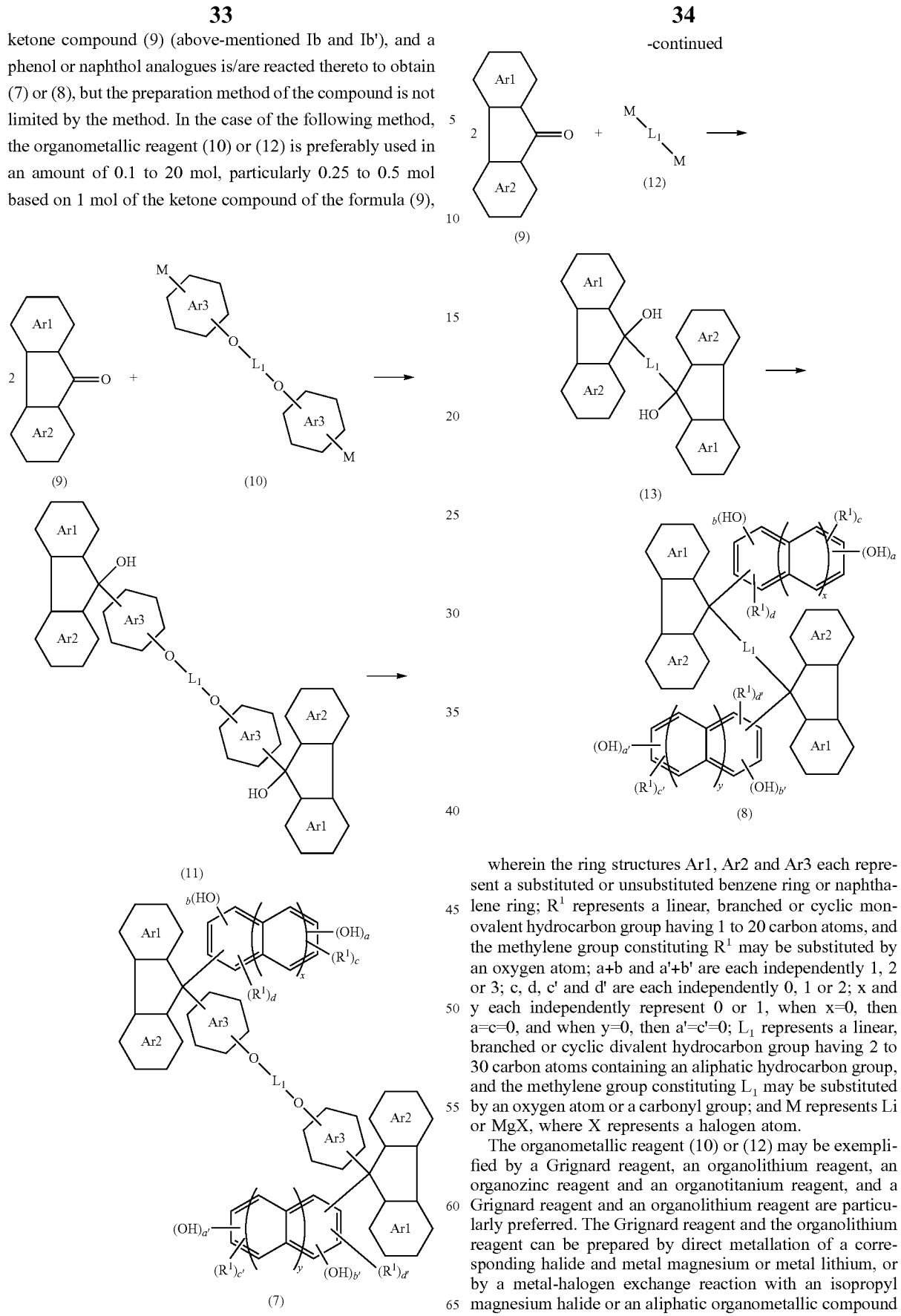

wherein the ring structures Ar1, Ar2 and Ar3 each represent a substituted or unsubstituted benzene ring or naphthalene ring; $R^1$ represents a linear, branched or cyclic monovalent hydrocarbon group having 1 to 20 carbon atoms, and the methylene group constituting $R^1$ may be substituted by an oxygen atom; a+b and a'+b' are each independently 1, 2 or 3; c, d, c' and d' are each independently 0, 1 or 2; x and y each independently represent 0 or 1, when x=0, then a=c=0, and when y=0, then a'=c'=0; $L_1$ represents a linear, branched or cyclic divalent hydrocarbon group having 2 to 30 carbon atoms containing an aliphatic hydrocarbon group, and the methylene group constituting $L_1$ may be substituted by an oxygen atom or a carbonyl group; and M represents Li or MgX, where X represents a halogen atom.

The organometallic reagent (10) or (12) may be exemplified by a Grignard reagent, an organolithium reagent, an organozinc reagent and an organotitanium reagent, and a Grignard reagent and an organolithium reagent are particularly preferred. The Grignard reagent and the organolithium reagent can be prepared by direct metallation of a corresponding halide and metal magnesium or metal lithium, or by a metal-halogen exchange reaction with an isopropyl magnesium halide or an aliphatic organometallic compound such as methyl lithium and butyl lithium. Also, the organozinc reagent or the organotitanium reagent can be prepared from a corresponding Grignard reagent or organolithium reagent by the reaction with a zinc halide, a titanium(IV) halide or a titanium(IV) alkoxide. At the time of preparing the organometallic reagent (10) or (12), or at the time of reacting the organometallic reagent and the ketone compound (9), a metal salt compound may be co-presented. The metal salt compound may be mentioned a cyanide, a halide and a perhalogenic acid salt, and particularly a lithium salt such as lithium chloride, lithium bromide, lithium iodide and lithium perchlorate, and a copper salt such as copper(I) cyanide, copper(II) cyanide, copper(I) chloride, copper(II) chloride and dilithium tetrachlorocuprate are preferably exemplified. The metal salt compound is added in an amount of 0.01 to 5.0 equivalents, preferably 0.2 to 2.0 equivalents based on an amount of the organometallic reagent, whereby the solubility of the organometallic reagent is increased to make it easily prepared, or, nucleophilicity or Lewis acidity of the reagent can be controlled. The solvent to be used for preparing the organometallic reagent (10) or (12) and in the reaction with the ketone compound (9) may be mentioned an ether such as diethyl ether, dibutyl ether, tetrahydrofuran, 1,4-dioxane and cyclopentyl methyl ether; a hydrocarbon such as benzene, toluene, xylene, mesitylene, hexane, heptane, octane and isooctane; an aprotic polar solvent such as N,N,N',N'-tetramethylethylenediamine, hexamethylphosphoric triamide and N,N-dimethylformamide, singly or in admixture. The reaction temperature may vary depending on a kind of the ketone compound (9) or the organometallic reagent (10) or (12) and reaction conditions, and preferably −70 to 150° C. For example, in the case of an organozinc reagent as (10) or (12), it is −70 to 0° C., and in the case of a Grignard reagent, it can be variously selected from room temperature to under reflux at the boiling point of the solvent.

The dehydration condensation reaction of the intermediate product (11) or (13) and a phenol or naphthol analogue is generally carried out by using an acid as a catalyst in the absence of a solvent or in a solvent at room temperature, or under cooling or under heating, if necessary. The solvent to be used may be exemplified by an alcohol such as methanol, ethanol, isopropyl alcohol, butanol, ethylene glycol, propylene glycol, diethylene glycol and glycerol; an ether such as ethylene glycol monomethyl ether, propylene glycol monomethyl ether, diethyl ether, dibutyl ether, diethylene glycol diethyl ether, diethylene glycol dimethyl ether, tetrahydrofuran and 1,4-dioxane; a chlorine solvent such as methylene chloride, chloroform, dichloroethane and trichloroethylene; a hydrocarbon such as hexane, heptane, benzene, toluene, xylene and cumene; a nitrile such as acetonitrile; a ketone such as acetone, ethyl methyl ketone and isobutyl methyl ketone; an ester such as ethyl acetate, n-butyl acetate and propylene glycol methyl ether acetate; and an aprotic polar solvent such as dimethylsulfoxide, N,N-dimethylformamide and hexamethylphosphoric triamide, and these may be used alone or may be used in combination of two or more kinds. The acid catalyst to be used may be mentioned an inorganic acid such as hydrochloric acid, hydrobromic acid, sulfuric acid, nitric acid, phosphoric acid and heteropoly acid; an organic acid such as oxalic acid, trifluoroacetic acid, methanesulfonic acid, benzenesulfonic acid, p-toluenesulfonic acid and trifluoromethanesulfonic acid; and a Lewis acid such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dimethoxide, dibutyltin oxide, titanium tetrachloride, titanium tetrabromide, titanium(IV) methoxide, titanium (IV) ethoxide, titanium(IV) isopropoxide and titanium(IV) oxide. The base catalyst to be used may be mentioned an inorganic base such as sodium hydroxide, potassium hydroxide, barium hydroxide, sodium carbonate, sodium hydrogen carbonate, potassium carbonate, lithium hydride, sodium hydride, potassium hydride and calcium hydride; an alkyl metal such as methyl lithium, n-butyl lithium, methylmagnesium chloride and ethylmagnesium bromide; an alkoxide such as sodium methoxide, sodium ethoxide and potassium t-butoxide; and an organic base such as triethylamine, diisopropylethylamine, N,N-dimethylaniline, pyridine and 4-dimethylaminopyridine. A reaction temperature is preferably from −50° C. to the boiling point of the solvent, more preferably room temperature to 100° C.

Here, for leading from (13) to (8) by the dehydration condensation reaction, when $L_1$ in (13) is, for example, a group having a carbon atom substituted by one or more hydrogen atoms at the terminal such as a polymethylene group, etc., (in the following (13'), $L_3$ represents a linear, branched or cyclic divalent hydrocarbon group having 1 to 28 carbon atoms, and the methylene group constituting $L_3$ may be substituted by an oxygen atom or a carbonyl group.), an intramolecular dehydration reaction proceeds to produce a by-product(s) (14) and (15) so that the objective composition (8) cannot be obtained with good yield.

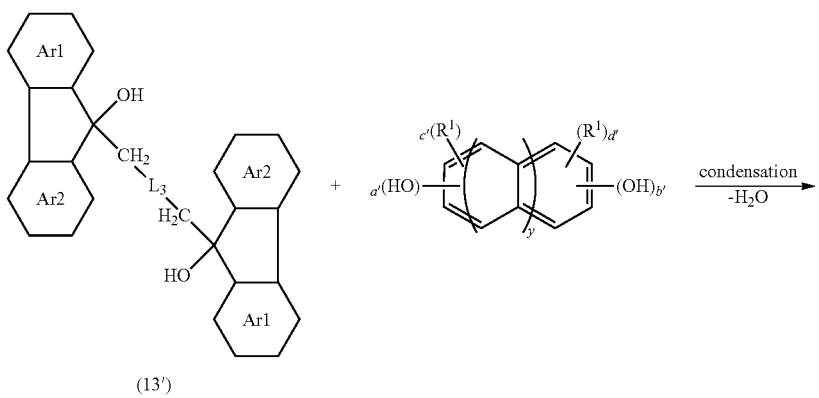

(13')

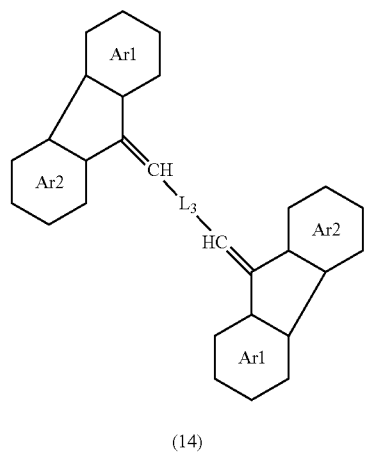

(14)

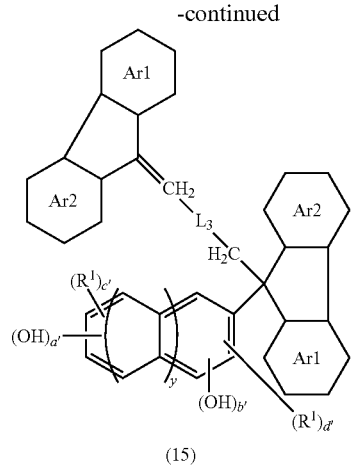

(15)

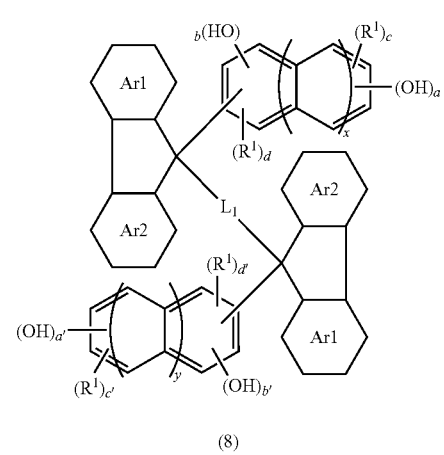

(8)

In the intermediate product (11) in which the ring structure Ar3 is introduced, it is preferred since an intramolecular dehydration reaction in the intermediate product does not occur whereby the objective composition (7) can be obtained with good yield.

The compound represented by the formula (1) may be exemplified by the following, but the invention is not limited by these.

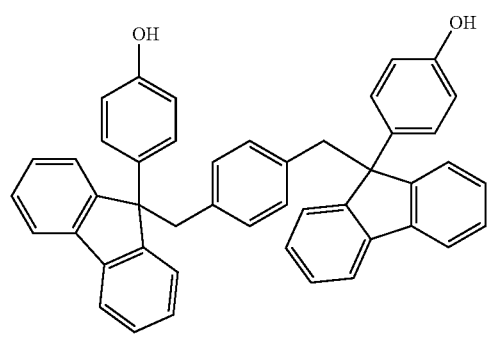

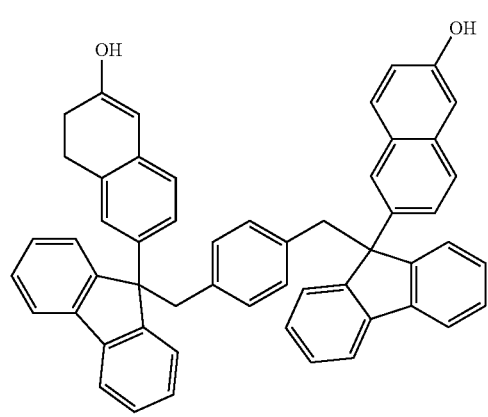

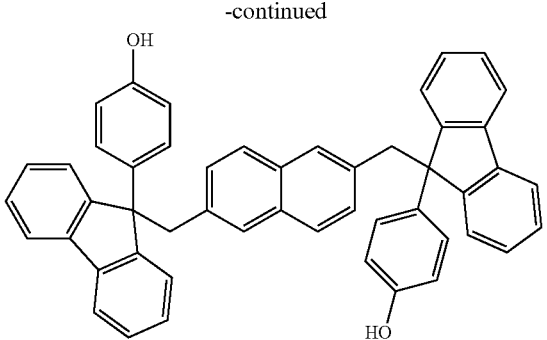

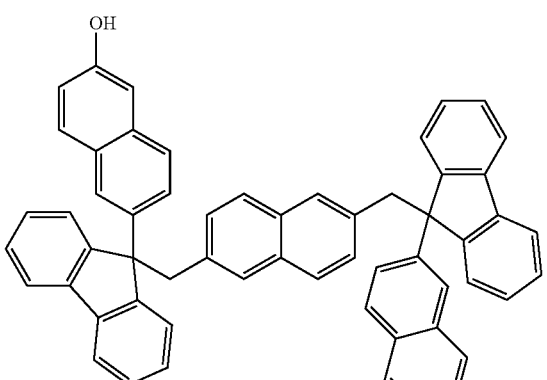

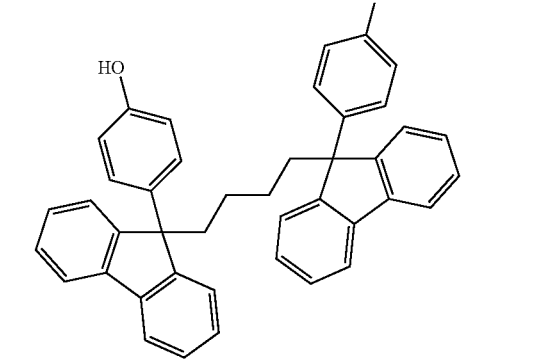

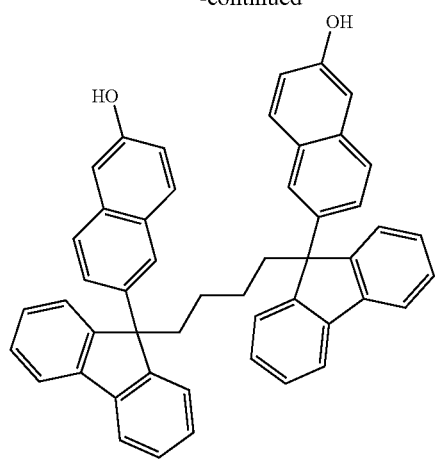
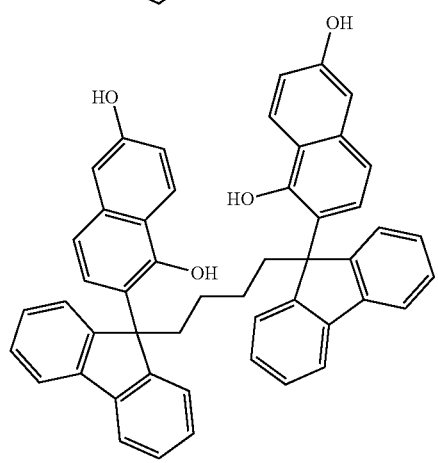
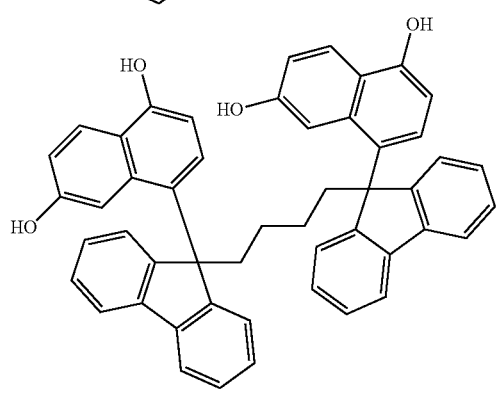
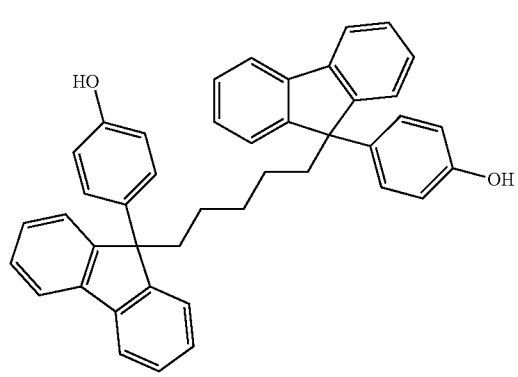
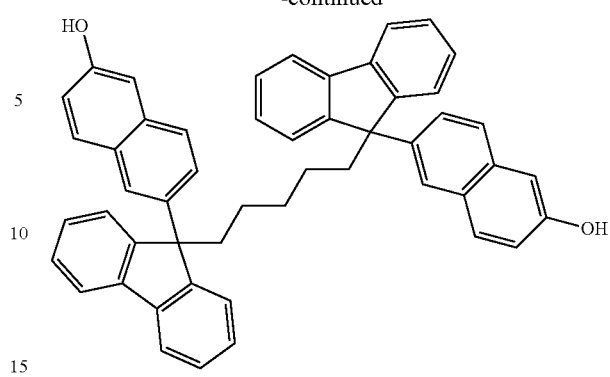
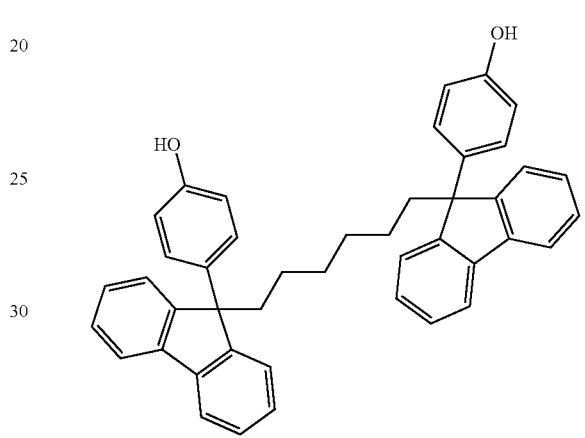
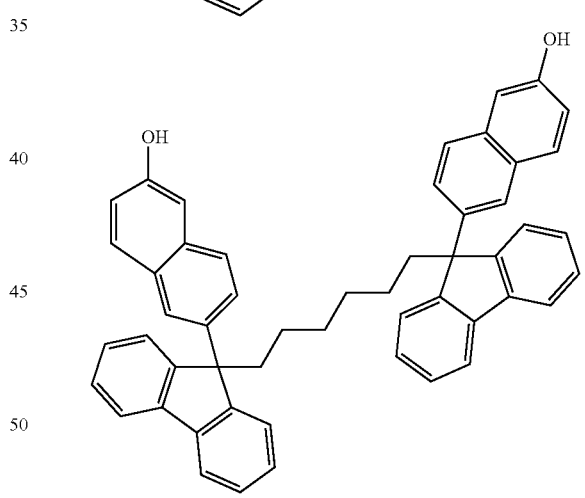
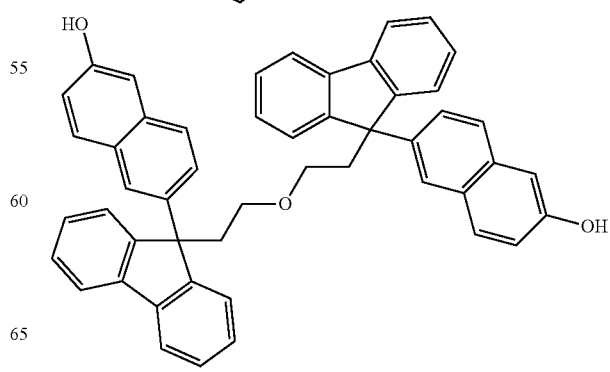

41
-continued
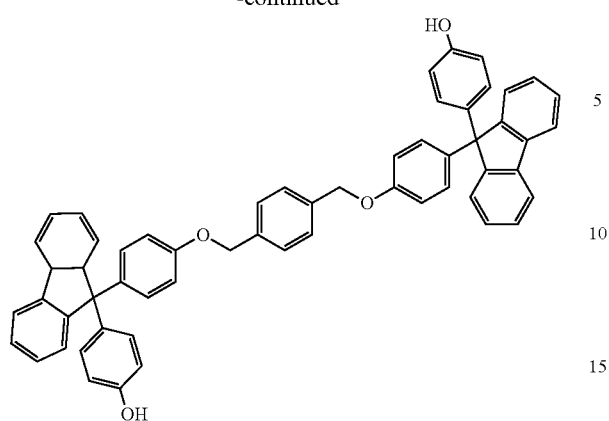
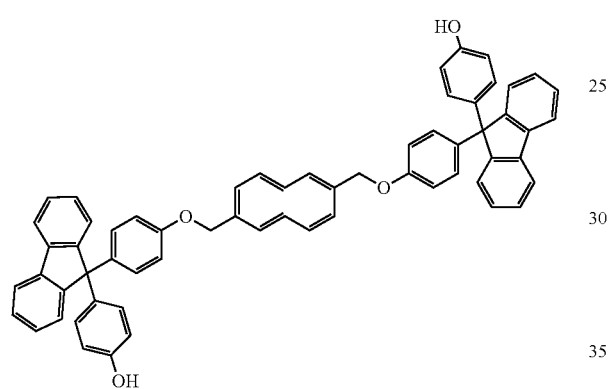
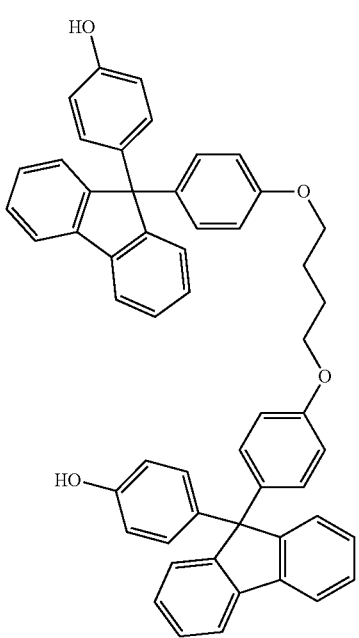
42
-continued
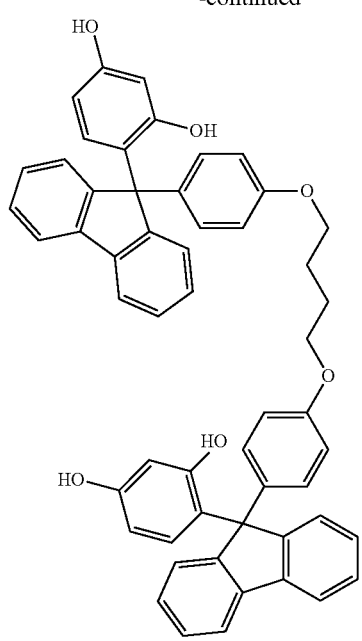
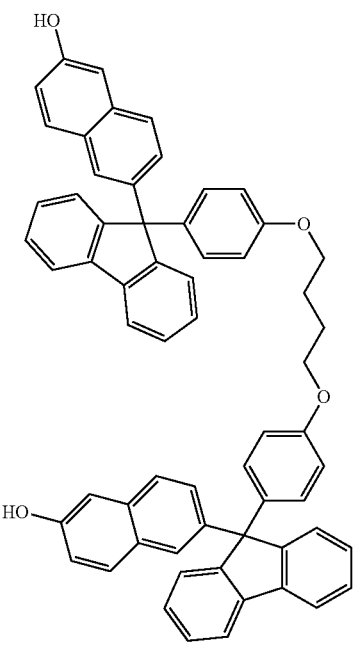

43
-continued
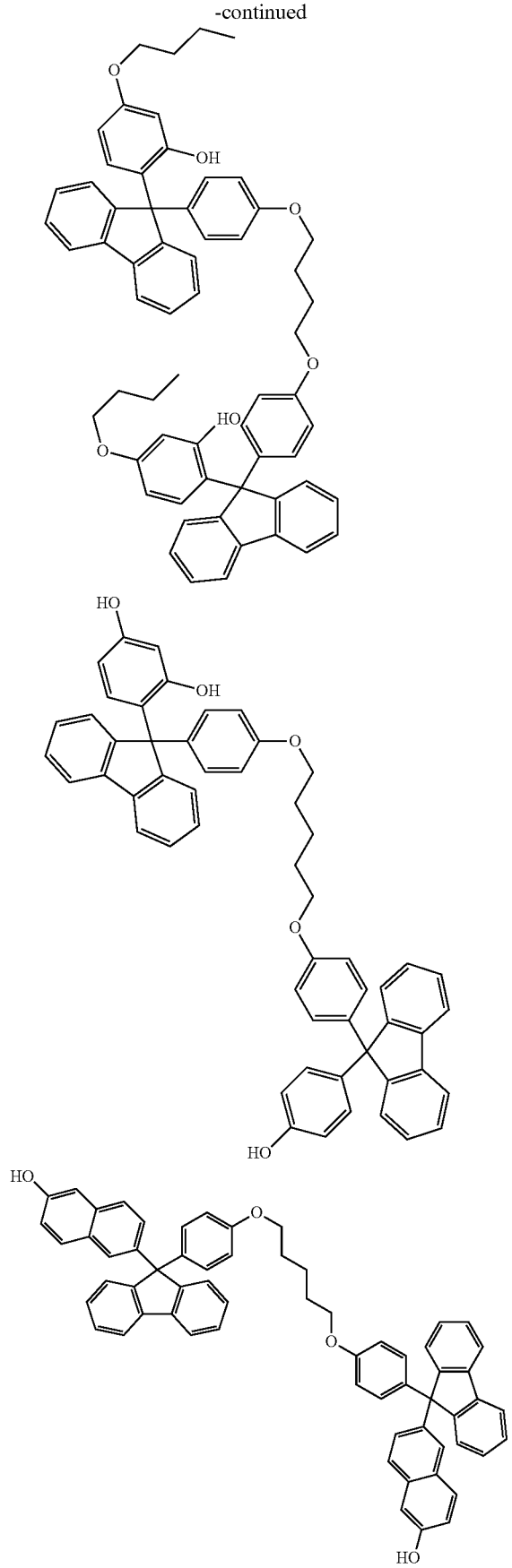
44
-continued
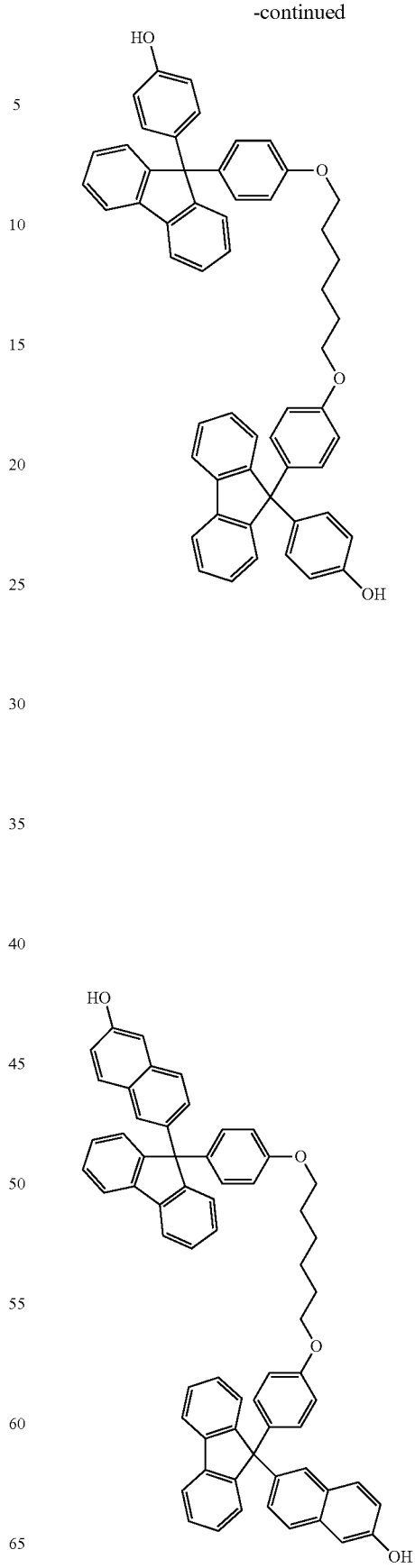

45
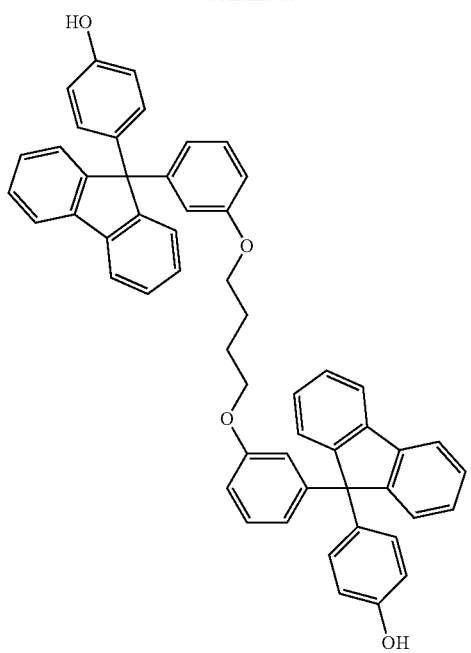
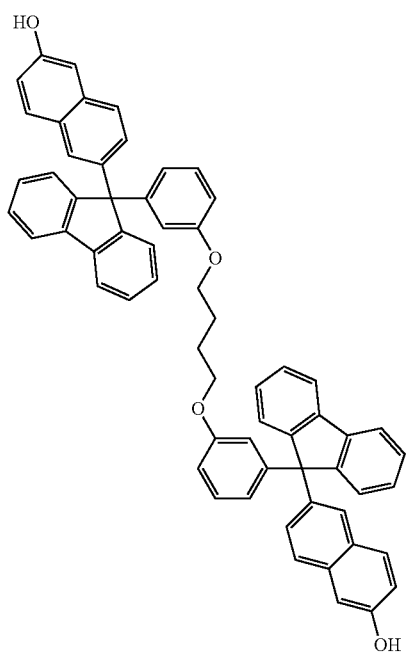
46
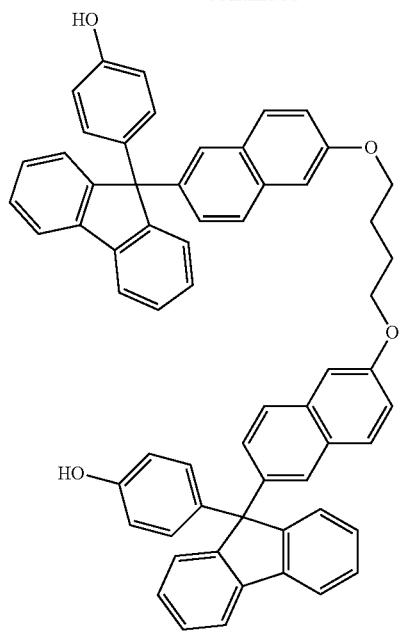
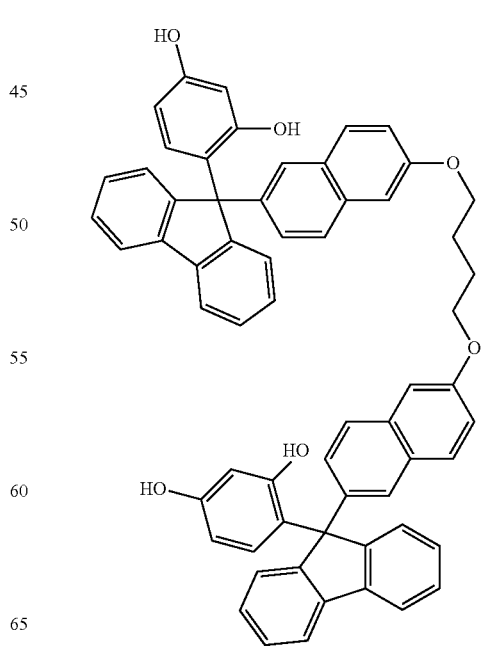

47
-continued
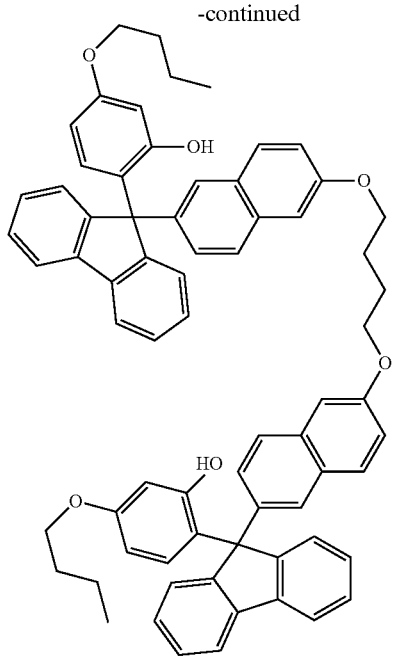
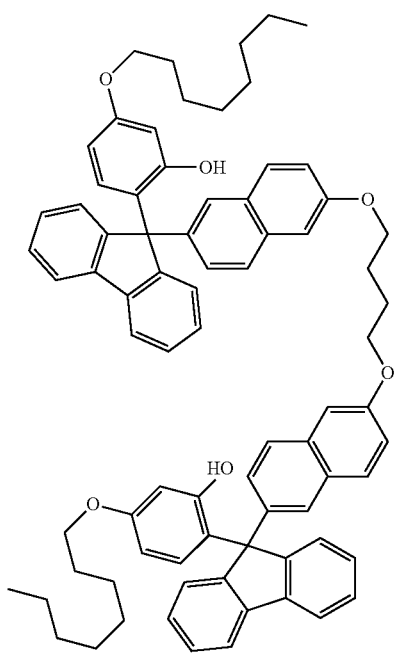
48
-continued
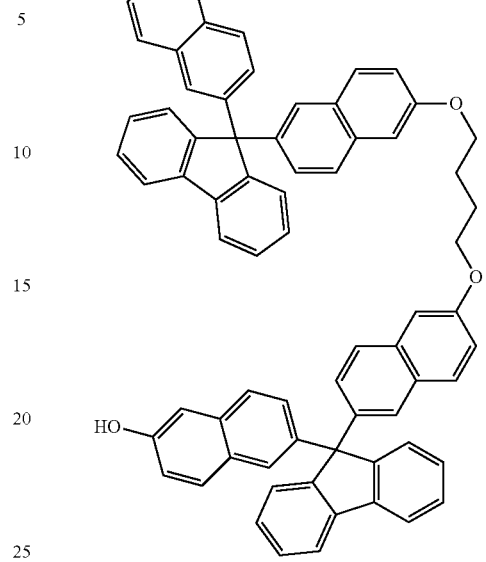
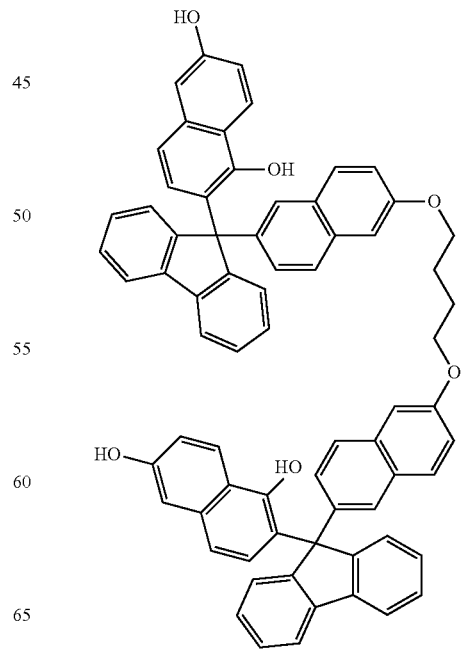

49
-continued
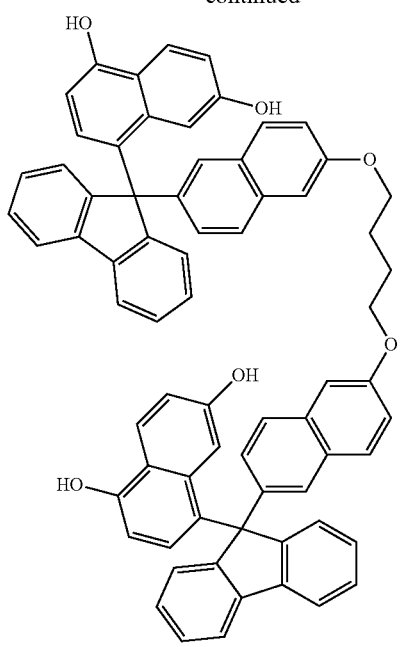
50
-continued
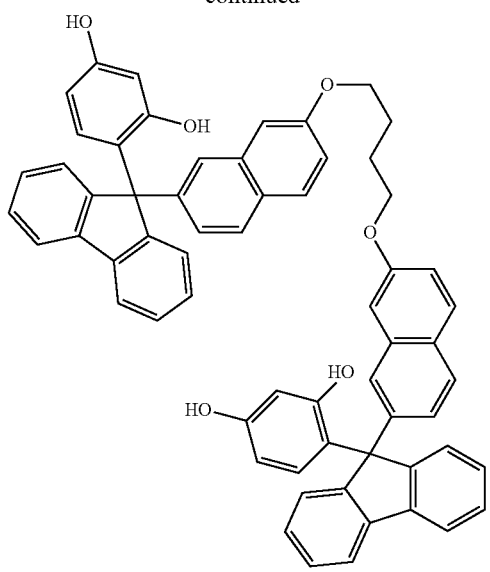
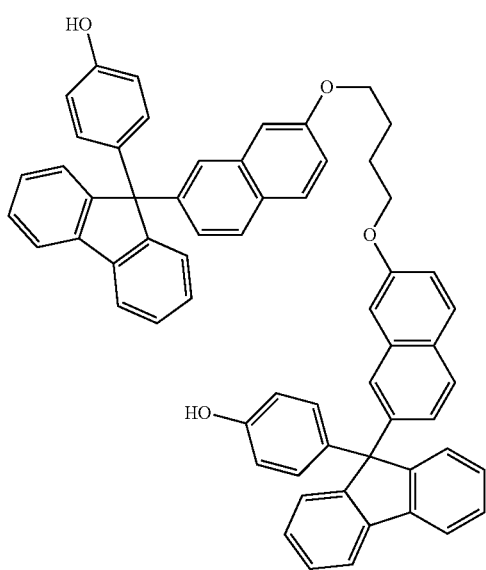
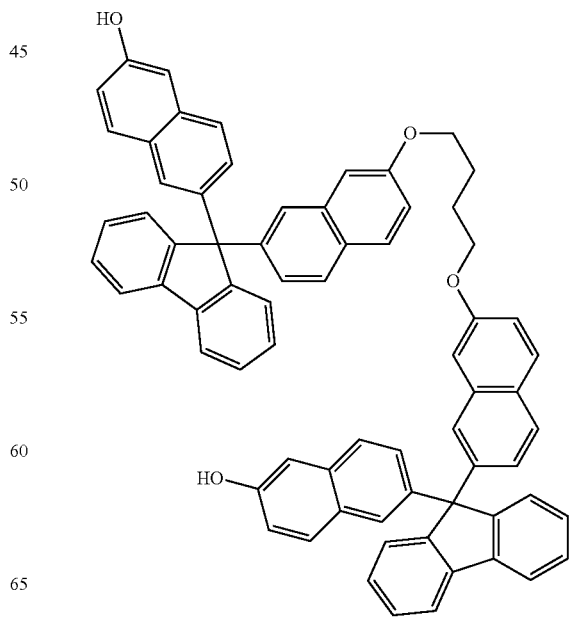

-continued

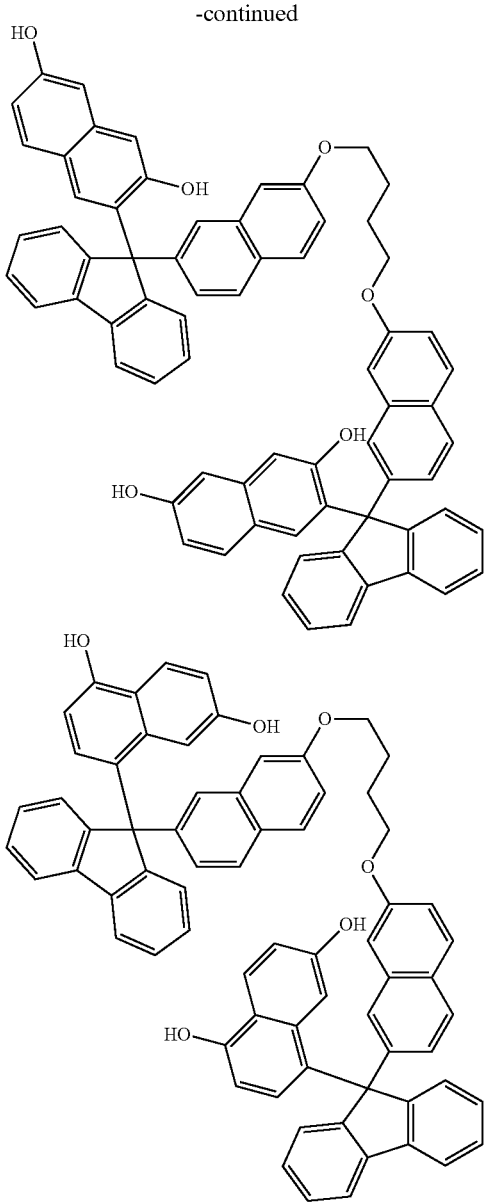

For using the organic film composition obtained by the present invention as a resist underlayer film or a planarizing composition for manufacturing a semiconductor apparatus, the compound represented by the formula (iii) may be polymerized, if necessary, to prepare a compound having a partial structure represented by the following formula (iv), (iv)

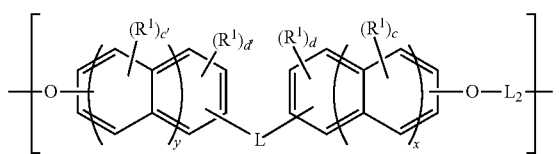

wherein $R^1$ represents a linear, branched or cyclic monovalent hydrocarbon group having 1 to 20 carbon atoms, and the methylene group constituting $R^1$ may be substituted by an oxygen atom; each c, d, c' and d' represent independently 0, 1 or 2; x and y each independently represent 0 or 1, when x=0, then c=0, and when y=0, then c'=0; L represents a partial structure represented by the formula (ii); $L_2$ represents a linear, branched or cyclic divalent organic group having 2 to 30 carbon atoms; and the methylene group constituting $L_2$ may be substituted by an oxygen atom or a carbonyl group, and the hydrogen atom constituting the structure may be substituted by a hydroxyl group.

As a preferred form of the partial structure represented by the formula (iv), a partial structure represented by the following formula (2) may be mentioned, (2)

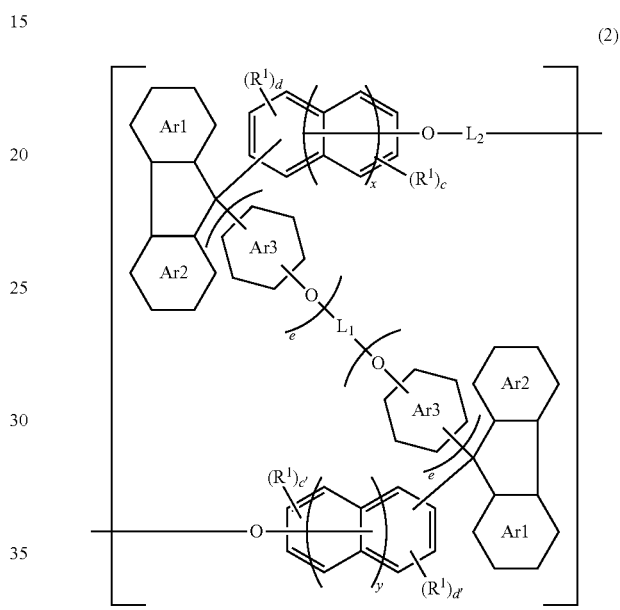

wherein the ring structures Ar1, Ar2 and Ar3 each represent a substituted or unsubstituted benzene ring or naphthalene ring; $R^1$ represents a linear, branched or cyclic monovalent hydrocarbon group having 1 to 20 carbon atoms, and the methylene group constituting $R^1$ may be substituted by an oxygen atom; each c, d, c' and d' represent independently 0, 1 or 2; x and y each independently represent 0 or 1, when x=0, then c=0, and when y=0, then c'=0; e is 0 or 1; $L_1$ represents a linear, branched or cyclic divalent hydrocarbon group having 2 to 30 carbon atoms containing an aliphatic hydrocarbon group; $L_2$ represents a linear, branched or cyclic divalent hydrocarbon group having 2 to 30 carbon atoms, and the methylene group constituting $L_1$ and $L_2$ may be substituted by an oxygen atom or a carbonyl group, and the hydrogen atom constituting $L_2$ may be substituted by a hydroxyl group.

The $L_2$ is a linear, branched or cyclic divalent hydrocarbon group having 2 to 30 carbon atoms, and the divalent hydrocarbon group may be specifically exemplified by the following.

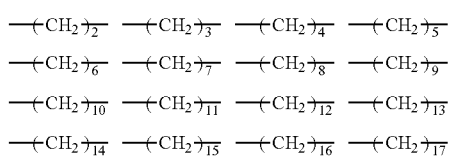

-continued

—(CH$_2$)$_{18}$—  —(CH$_2$)$_{19}$—  —(CH$_2$)$_{20}$—  —(CH$_2$)$_{21}$—

—(CH$_2$)$_{22}$—  —(CH$_2$)$_{23}$—  —(CH$_2$)$_{24}$—  —(CH$_2$)$_{25}$—

—(CH$_2$)$_{26}$—  —(CH$_2$)$_{27}$—  —(CH$_2$)$_{28}$—  —(CH$_2$)$_{29}$—

—(CH$_2$)$_{30}$—

—O—(CH$_2$)$_2$—O—    —O—(CH$_2$)$_3$—O—

—O—(CH$_2$)$_4$—O—    —O—(CH$_2$)$_5$—O—

—O—(CH$_2$)$_6$—O—    —O—(CH$_2$)$_7$—O—

—O—(CH$_2$)$_8$—O—    —O—(CH$_2$)$_9$—O—

—O—(CH$_2$)$_{10}$—O—    —O—(CH$_2$)$_{11}$—O—

—O—(CH$_2$)$_{12}$—O—    —O—(CH$_2$)$_{13}$—O—

—O—(CH$_2$)$_{14}$—O—    —O—(CH$_2$)$_{15}$—O—

—O—(CH$_2$)$_{16}$—O—    —O—(CH$_2$)$_{17}$—O—

—O—(CH$_2$)$_{18}$—O—    —O—(CH$_2$)$_{19}$—O—

—O—(CH$_2$)$_{20}$—O—    —O—(CH$_2$)$_{30}$—O—

—O—(CH$_2$—CH$_2$—O)$_3$—    —O—(CH$_2$—CH$_2$—O)$_4$—

—O—(CH$_2$—CH$_2$—O)$_5$—    —O—(CH$_2$—CH$_2$—O)$_6$—

—O—(CH$_2$—CH$_2$—O)$_7$—    —O—(CH$_2$—CH$_2$—O)$_8$—

—O—(CH$_2$—CH$_2$—O)$_9$—    —O—(CH$_2$—CH$_2$—O)$_{10}$—

—O—(CH$_2$—CH$_2$—O)$_{11}$—    —O—(CH$_2$—CH$_2$—O)$_{12}$—

—O—(CH$_2$—CH$_2$—O)$_{13}$—    —O—(CH$_2$—CH$_2$—O)$_{14}$—

—O—(CH$_2$—CH$_2$—O)$_{15}$—

—O—(C$_3$H$_6$—O)—    —O—(C$_3$H$_6$—O)$_2$—

—O—(C$_3$H$_6$—O)$_3$—    —O—(C$_3$H$_6$—O)$_4$—

—O—(C$_3$H$_6$—O)$_5$—    —O—(C$_3$H$_6$—O)$_6$—

—O—(C$_3$H$_6$—O)$_7$—    —O—(C$_3$H$_6$—O)$_8$—

—O—(C$_3$H$_6$—O)$_9$—    —O—(C$_3$H$_6$—O)$_{10}$—

In addition, there may be exemplified by a group in which two hydrogen atoms are removed from a hydrocarbon group such as propylene, n-butane, 1-butene, 2-butene, isobutane, n-pentane, n-hexane, n-heptane, n-octane, n-nonane, n-decane, n-dodecane, n-eicosane, 1,4-dimethylcyclohexane, 1,3-dimethyladamantane, o-xylene, m-xylene, p-xylene, 1,4-dimethylnaphthalene, 1,5-dimethylnaphthalene, 2,6-dimethylnaphthalene and 2,7-dimethylnaphthalene.

Examples of making a higher molecular weight of the compound represented by the formula (iii),
P1) condensation reaction with an organic halogen compound and
P2) condensation reaction with a polyol are mentioned and explained.

P1) Condensation Reaction with an Organic Halogen Compound

The condensation reaction of the compound represented by the formula (iii) and an organic halogen compound is generally carried out in the absence of a solvent or in a solvent, at room temperature, or under cooling or under heating, if necessary.

The organic halogen compound may be specifically exemplified by a dihaloalkane such as 1,2-dichloroethane, 1,2-dibromoethane, 1,3-dichloropropane, 1,3-dibromopropane, 1,3-diiodopropane, 1,4-dichlorobutane, 1,4-dibromobutane, 1-bromo-4-chlorobutane, 1,4-diiodobutane, 1,5-dichloropentane, 1,5-dibromopentane, 1,5-diiodopentane, 1,6-dichlorohexane, 1,6-dibromohexane, 1-bromo-6-chlorohexane, 1,6-diiodohexane, α,α'-dibromo-m-xylene, α,α'-dibromo-o-xylene, α,α'-dibromo-p-xylene, 2,5-bromomethylnaphthalene, 2,6-bromomethylnaphthalene, 2,7-bromomethylnaphthalene and 1,8-bromomethylnaphthalene; and an epihalohydrin such as epifluorohydrin, epichlorohydrin, epibromohydrin, epiiodohydrin and β-methylepichlorohydrin, but the invention is not limited by these. These organic halogen compounds may be used alone or may be used in combination of two or more kinds.

An amount of the organic halogen compound to be used is preferably 0.05 to 5 mol, more preferably 0.1 to 1.5 mol based on 1 mol of the compound represented by the formula (iii).

The condensation reaction with the organic halogen compound is preferably carried out under basic conditions. The base to be used may be exemplified by an inorganic base such as sodium hydroxide, potassium hydroxide, barium hydroxide, sodium carbonate, sodium hydrogen carbonate, potassium carbonate, lithium hydride, sodium hydride, potassium hydride and calcium hydride; an alkyl metal such as methyl lithium, n-butyl lithium, methylmagnesium chloride and ethylmagnesium bromide; an alkoxide such as sodium methoxide, sodium ethoxide and potassium t-butoxide; and an organic base such as triethylamine, diisopropylethylamine, N,N-dimethylaniline, pyridine and 4-dimethylaminopyridine. An amount of the base to be used is preferably 1.0 to 5.0 mol, more preferably 2.0 to 3.0 mol based on 1 mol of the compound represented by the formula (iii). As the method of the reaction, the compound represented by the formula (iii), the organic halogen compound and a base are charged at once, or a method in which an optional component is added dropwise. The base or metal impurities can be removed by the usual aqueous post-treatment. As others, by adding a poor solvent and separating the poor solvent layer, starting composition(s) or low molecular weight polymer fraction(s) can be removed. Moreover, if necessary, an amount of the metal impurities can be reduced by passing through a metal-removing filter. These purification treatments may be carried out singly or may be carried out in combination of two or more kinds.

The solvent to be used in the condensation reaction may be exemplified by an ether such as diethyl ether, dibutyl ether, diethylene glycol diethyl ether, diethylene glycol dimethyl ether, tetrahydrofuran and 1,4-dioxane; a chlorine solvent such as methylene chloride, chloroform, dichloroethane and trichloroethylene; a hydrocarbon such as hexane, heptane, benzene, toluene, xylene and cumene; a nitrile such as acetonitrile; a ketone such as acetone, ethyl methyl ketone and isobutyl methyl ketone; an ester such as ethyl acetate, n-butyl acetate and propylene glycol methyl ether acetate; and an aprotic polar solvent such as dimethylsulfoxide, N,N-dimethylformamide, hexamethylphosphoric triamide and N-methyl-2-pyrrolidone, and these may be used alone or may be used in combination of two or more kinds. The reaction may be carried out by two-layer using the organic solvent and water, and in this case, to proceed the reaction rapidly, there may be added a phase-transfer catalyst such as tetramethylammonium chloride, tetraethylammonium bromide, tetraethylammonium chloride, tetrapropylammonium bromide, tetrapropylammonium hydroxide, tetrabutylammonium bromide, tetrabutylammonium hydroxide, tetrabutylammonium hydrogen sulfate, tributylmethylammonium chloride, trioctylmethylammonium chloride, trilaurylmethylammonium chloride, benzyltrimethylammonium chloride, benzyltrimethylammonium hydroxide, benzyltriethylammonium chloride, benzyltributylammonium chloride and phenyltrimethylammonium chloride.

A reaction temperature of the condensation reaction is preferably from −50° C. to the boiling point of the solvent, more preferably room temperature to 150° C.

At the time of the condensation reaction of the compound represented by the formula (iii), co-condensation may be carried out by co-presenting other phenol compound(s) having a plural number of phenolic hydroxyl groups. The phenol compound capable of carrying out the co-condensation may be mentioned resorcinol, 2-methylresorcinol, 4-methylresorcinol, 5-methylresorcinol, catechol, hydroquinone, 4-t-butylcatechol, 1,5-dihydroxynaphthalene, 1,6-dihydroxynaphthalene, 1,7-dihydroxynaphthalene, 2,6-dihydroxynaphthalene, 2,7-dihydroxynaphthalene, bisphenol, 9,9-bis(4-hydroxyphenyl)fluorene, 9,9-bis(6-hydroxy-2-naphthyl)fluorene and trisphenol. Also, the hydrogen atom(s) in these compounds may be substituted by a halogen atom, a hydrocarbon group, a hydroxyl group, an alkoxy group, a nitro group, and a cyano group.

Incidentally, there is a case that the compound having a partial structure represented by the formula (iv) when e=1, there can be synthesized bypassing the condensation reaction of the compound represented by the formula (iii). That is, a compound represented by the formula (3a) mentioned below and the organic halogen compound are reacted under the basic conditions to obtain a compound wherein $L_1$ and $L_2$ in the formula (iv) are the same. Examples of the compound represented by the formula (3a) are mentioned below. At this time, an amount of the organic halogen compound to be used is preferably 0.1 to 10 mol, more preferably 0.3 to 5 mol based on 1 mol of (3a).

P2) Condensation Reaction with a Polyol

The condensation reaction of the compound represented by the formula (iii) with a polyol is generally carried out in the absence of a solvent or in a solvent, at room temperature, or under cooling or under heating, if necessary.

The polyol may be specifically exemplified by ethylene glycol, polyethylene glycol such as diethylene glycol, triethylene glycol, tetraethylene glycol, pentaethylene glycol and hexaethylene glycol; propylene glycol and glycerin, but the invention is not limited by these. These polyols may be used alone or may be used in combination of two or more kinds.

An amount of the polyol to be used is preferably 0.1 to 10.0 mol, more preferably 0.3 to 5.0 mol based on 1 mol of the compound represented by the formula (iii).

In the condensation reaction, a catalyst may be used. An acid catalyst is particularly preferred. The acid catalyst which can be used may be mentioned an inorganic acid such as hydrochloric acid, hydrobromic acid, nitric acid, sulfuric acid, formic acid, phosphoric acid and heteropoly acid; an organic acid such as oxalic acid, acetic acid, trifluoroacetic acid, methanesulfonic acid, benzenesulfonic acid, p-toluenesulfonic acid and trifluoromethanesulfonic acid; and a Lewis acid such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide and titanium(IV) oxide. More specifically, there may be mentioned an acid catalyst such as hydrochloric acid, nitric acid, sulfuric acid, formic acid, oxalic acid, acetic acid, methanesulfonic acid, camphorsulfonic acid, p-toluenesulfonic acid and trifluoromethanesulfonic acid. An amount of these acid catalysts to be used is 0.1 to 50.0 mol based on 1 mol of the compound represented by the formula (iii). As the method of the reaction, there is a method in which the compound represented by the formula (iii), a polyol and a catalyst are charged at once, or a method in which an optional component is added dropwise. After completion of the reaction, to remove unreacted starting composition(s) or a catalyst existing in the reaction system, a temperature of the reaction vessel is raised to 130 to 230° C., and a volatile component(s) can be removed at 1 to 50 mmHg. The catalyst or metal impurities can be removed by the usual aqueous post-treatment. As others, by adding a poor solvent and separating the poor solvent layer, starting composition(s) or low molecular weight polymer fraction(s) can be removed. Moreover, if necessary, an amount of the metal impurities can be reduced by passing through a metal-removing filter. These purification treatments may be carried out singly or may be carried out in combination of two or more kinds.

The solvent to be used in the condensation reaction may be exemplified by an alcohol such as methanol, ethanol, isopropyl alcohol, butanol, ethylene glycol, propylene glycol, diethylene glycol and glycerol; an ether such as ethylene glycol monomethyl ether, propylene glycol monomethyl ether, diethyl ether, dibutyl ether, diethylene glycol diethyl ether, diethylene glycol dimethyl ether, tetrahydrofuran and 1,4-dioxane; a chlorine solvent such as methylene chloride, chloroform, dichloroethane and trichloroethylene; a hydrocarbon such as hexane, heptane, benzene, toluene, xylene and cumene; a nitrile such as acetonitrile; a ketone such as acetone, ethyl methyl ketone and isobutyl methyl ketone; an ester such as ethyl acetate, n-butyl acetate and propylene glycol methyl ether acetate; and an aprotic polar solvent such as dimethylsulfoxide, N,N-dimethylformamide and hexamethylphosphoric triamide, and these may be used alone or may be used in combination of two or more kinds.

A reaction temperature of the condensation reaction is preferably from −50° C. to the boiling point of the solvent, more preferably room temperature to 150° C.

At the time of the condensation reaction of the compound represented by the formula (iii), co-condensation may be carried out by co-presenting other phenol compound(s) having a plural number of phenolic hydroxyl groups. The phenol compound capable of carrying out the co-condensation may be mentioned resorcinol, 2-methylresorcinol, 4-methylresorcinol, 5-methylresorcinol, catechol, hydroquinone, 4-t-butylcatechol, 1,5-dihydroxynaphthalene, 1,6-dihydroxynaphthalene, 1,7-dihydroxynaphthalene, 2,6-dihydroxynaphthalene, 2,7-dihydroxynaphthalene, bisphenol, 9,9-bis(4-hydroxyphenyl)fluorene, 9,9-bis(6-hydroxy-2-naphthyl)fluorene and trisphenol. Also, the hydrogen atom(s) in these compounds may be substituted by a halogen atom, a hydrocarbon group, a hydroxyl group, an alkoxy group, a nitro group, and a cyano group.

Also, into the phenol structure and naphthol structure of the compound represented by the formula (iii) or the compound having a partial structure represented by the formula (iv) may be introduced an aromatic or alicyclic substituent. Here, the substituent which can be introduced may be specifically mentioned as follows.

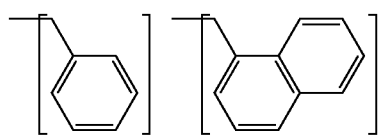

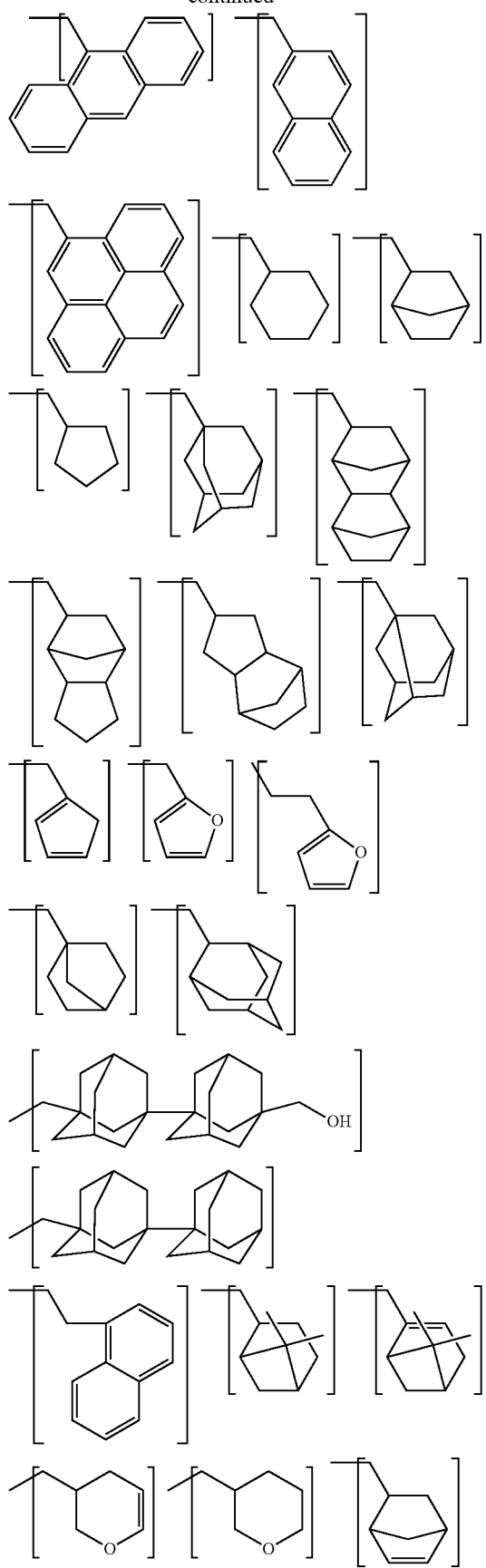
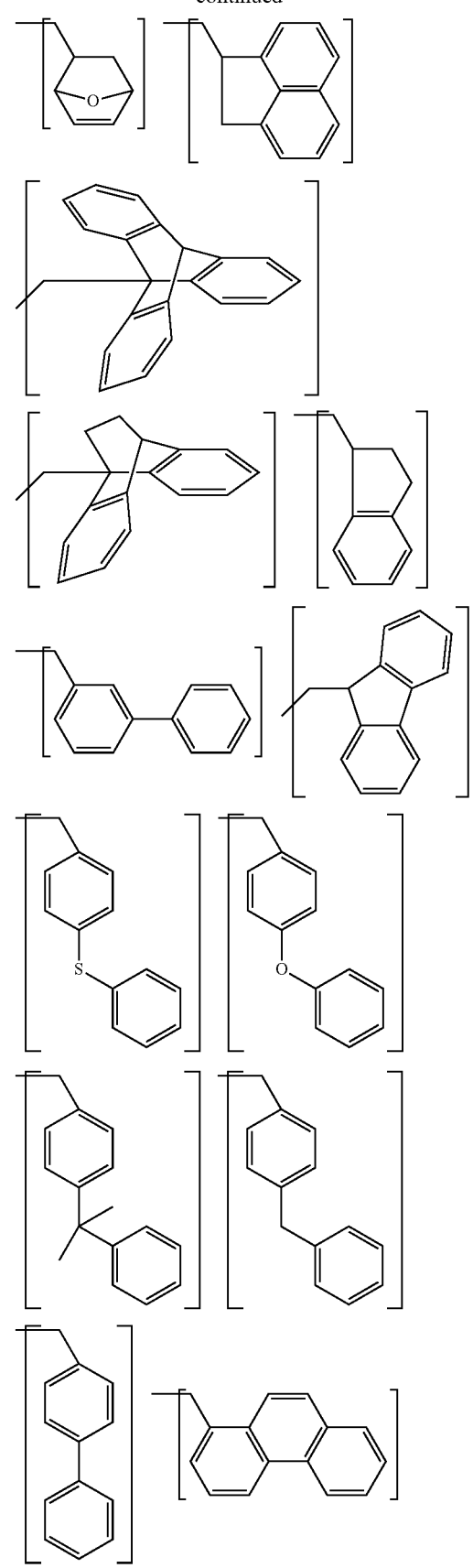

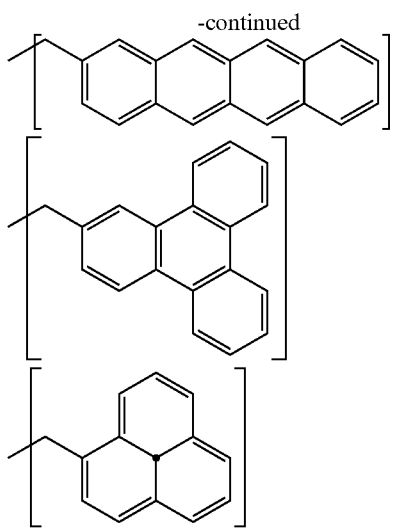

Among the substituents, for exposure at 248 nm, a polycyclic aromatic group, for example, an anthracenemethyl group and a pyrenemethyl group are most preferably used. To improve transparency at 193 nm, those having an alicyclic structure or those having a naphthalene structure are preferably used. The introducing method of the substituent may be mentioned a method in which an alcohol compound which the bonding position of the substituent is a hydroxyl group is introduced into the compound represented by the formula (iii) or the compound having a partial structure represented by the formula (iv) in the presence of an acid catalyst. Examples of the acid catalyst may be mentioned the same one as the acid catalyst mentioned in the condensation reaction (P2) of the polyol.

A molecular weight of the compound having the partial structure represented by the formula (iv) is preferably a weight average molecular weight (Mw) in terms of a polystyrene according to gel permeation chromatography (GPC) using tetrahydrofuran as a solvent of 400 to 100,000, particularly preferably 500 to 10,000. A molecular weight distribution in the range of 1.2 to 7 is preferably used. When a monomer component, an oligomer component or a low molecular weight component having a molecular weight (Mw) of less than 1,000 is cut to narrow the molecular weight distribution, cross-linking efficiency becomes high. Also, by restraining an amount of the volatile component during the baking, contamination at the peripheral of the baking cup can be prevented.

Also, in the present invention, as those having the partial structure represented by the formula (ii), a polymer compound having at least one of a partial structure represented by the following formula (v), a partial structure represented by the following formula (vi), and a partial structure represented by the following formula (vii) can be used.

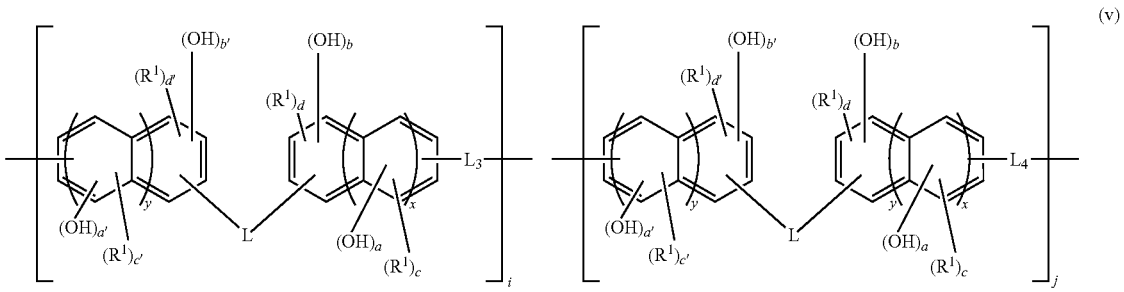

wherein $R^1$, a, b, a', b', c, d, c', d', x, y and L have the same meanings as defined above; $L_3$ represents a linear, branched or cyclic divalent organic group having 1 to 20 carbon atoms, $L_4$ represents $L_3$, a partial structure represented by the formula (i), or a partial structure represented by the formula (ii); $0 \leq i \leq 1$, $0 \leq j \leq 1$ and $i+j=1$.

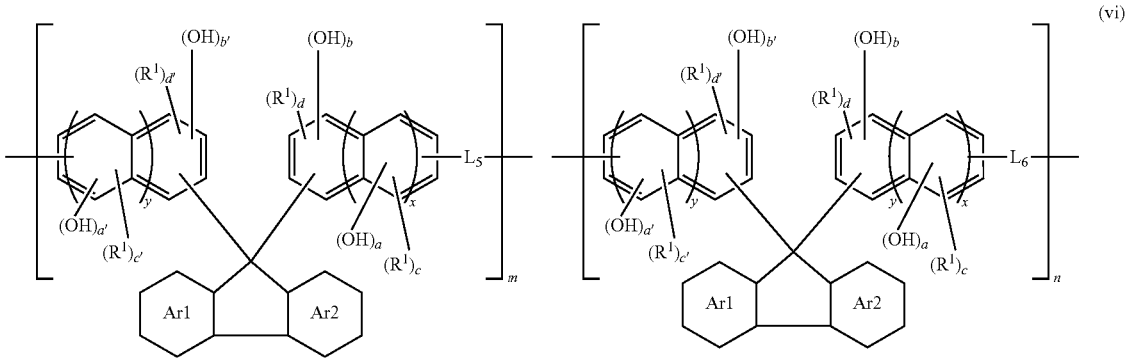

wherein Ar1, Ar2, R$^1$, a, b, a', b', c, d, c', d', x and y have the same meanings as defined above; L$_5$ represents a linear, branched or cyclic divalent organic group having 1 to 20 carbon atoms, L$_6$ represents a partial structure represented by the formula (i) or a partial structure represented by the formula (ii); 0≤m<1, 0<n≤1 and m+n=1.

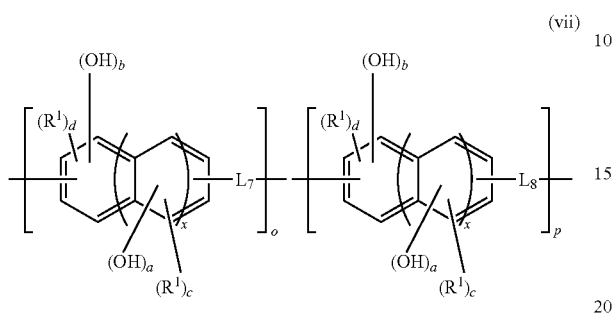

(vii)

wherein R$^1$, a, b, c, d and x have the same meanings as defined above; L$_7$ represents a linear, branched or cyclic divalent organic group having 1 to 20 carbon atoms, L$_8$ represents a partial structure represented by the formula (i) or a partial structure represented by the formula (ii); 0≤o<1, 0<p≤1 and o+p=1.

The organic group represented by L$_3$, L$_5$ or L$_7$ in the formulae may be exemplified by the following.

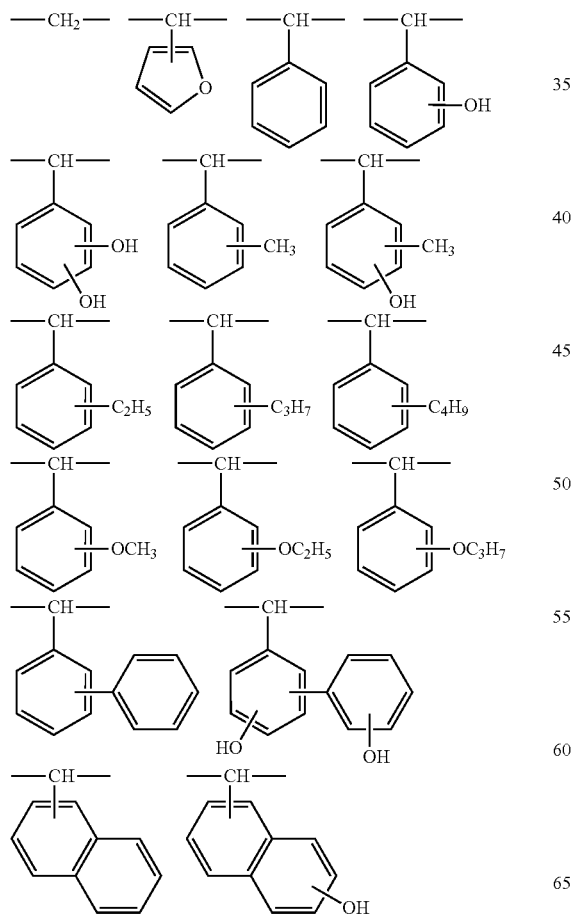

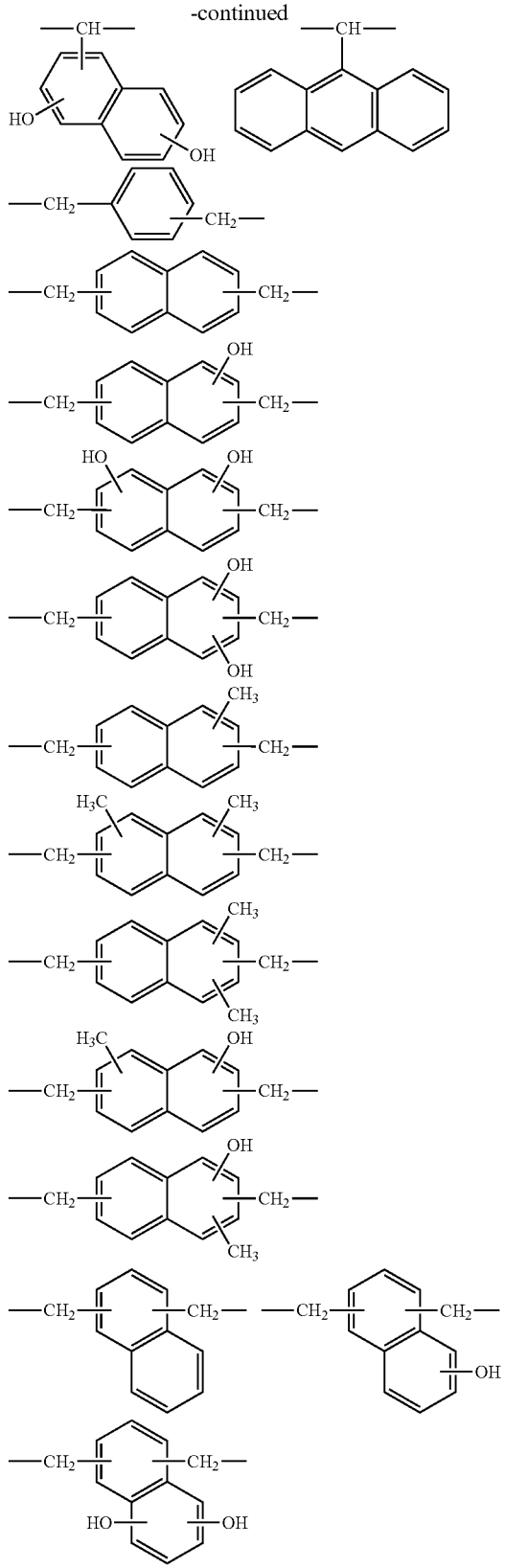

Of these, the partial structure represented by the formula (v) can be obtained by reacting the compound represented by the formula (ii) mentioned above with Compound (11) or Compound (13) which is a reaction intermediate. At this time, A-CHO is further reacted with Compound (10) to obtain a compound represented by the formula (v). The reaction conditions are the same as the conditions of obtaining (D) the resin containing an aromatic ring as mentioned below.

Also, the present invention provides an organic film composition which uses one or more of (A) the compound represented by the formula (iii), (B) the compound having the partial structure represented by the formula (iv), (C-1) the polymer compound having the partial structure represented by the formula (iv) as a part of the repeating unit, (C-2) the polymer compound having the partial structure represented by the formula (v), (C-3) the polymer compound having the partial structure represented by the formula (vi), and (C-4) the polymer compound having the partial structure represented by the formula (vii). The organic film composition can be used for the use of a resist underlayer film composition or a planarizing composition for manufacturing a semiconductor apparatus.

The organic film composition may further contain (D) a resin containing an aromatic ring which is different from the (C-1) to (C-4).

The resin (D) containing an aromatic ring which can be formulated into the organic film composition is not specifically limited so long as it is a resin satisfying a film-forming property by spin coating and curability, and it is more preferred to contain a naphthalene ring in the view points of etching resistance, optical characteristic and heat resistance.

As (D) the resin containing an aromatic ring suitably formulated with the organic film composition, more specifically, there may be preferably mentioned those containing a resin obtained by polycondensating one or two or more kinds of the following aromatic ring-containing compounds, and a compound represented by the below mentioned formula (4) under acidic or basic conditions, in addition to (D-1) and (D-2) mentioned hereinbelow. In the following formulae, Me represents a methyl group, and hereinafter the same.

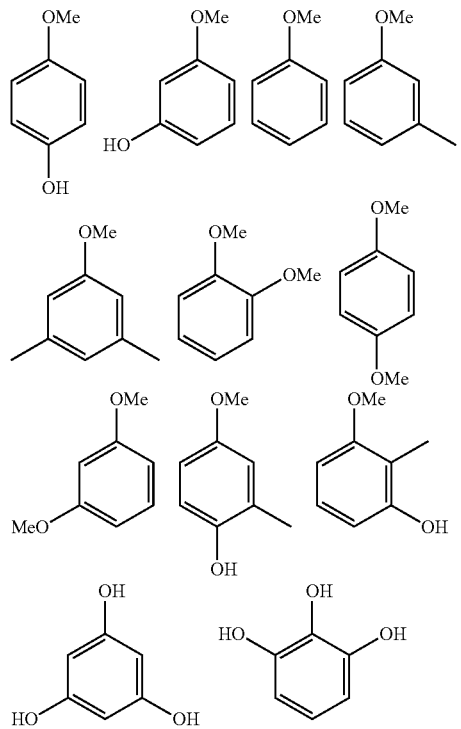

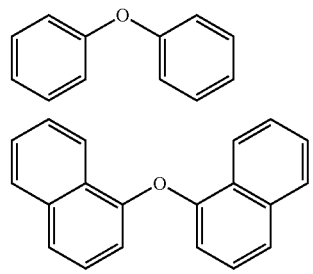

-continued

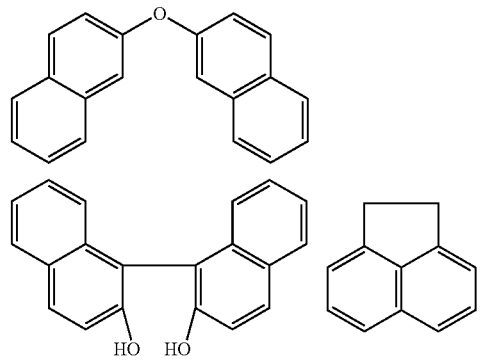

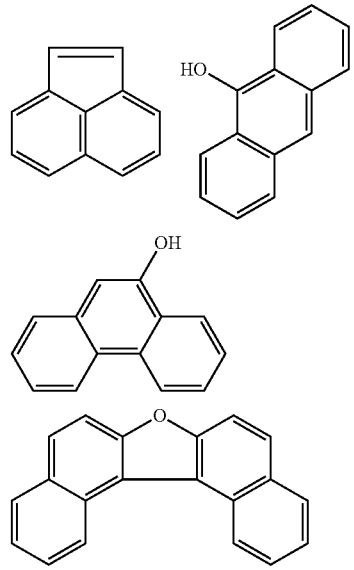

As (D) the resin containing an aromatic ring to be formulated into the organic film composition, more specifically, there may be preferably mentioned those containing a resin (D-1) obtained by polycondensating either one or more of the compound(s) represented by the following formulae (3a) and (3b), and a compound represented by the below mentioned formula (4),

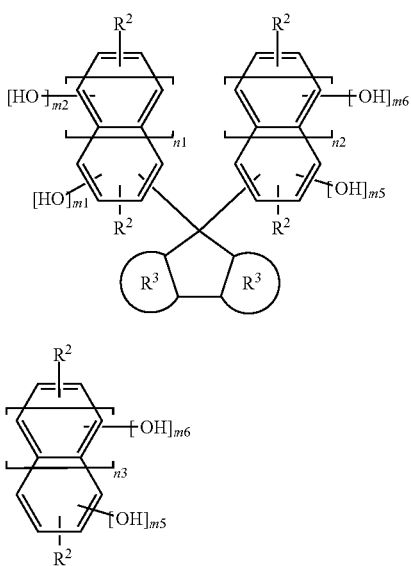

(3a)

(3b)

wherein each $R^2$ each independently represent a hydrogen atom or a saturated or unsaturated hydrocarbon group having 1 to 20 carbon atoms; each $R^3$ independently represent a benzene ring or a naphthalene ring; each m1+m2, m3+m4 and m5+m6 represent 1 or 2; and each n1, n2 and n3 represent 0 or 1,

A-CHO    (4)

wherein A represents either one of a hydrogen atom, a hydrocarbon group having 1 to 10 carbon atoms and a substituted or unsubstituted aromatic hydrocarbon group having 6 to 20 carbon atoms.

The compound represented by the formula (3a) may be specifically exemplified as follows.

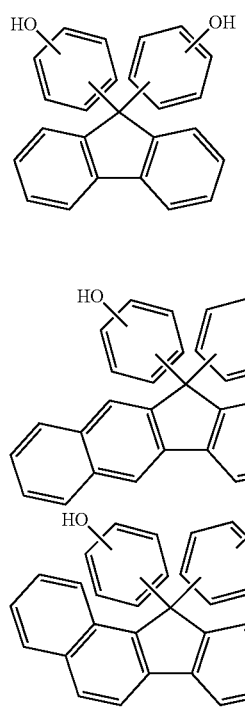

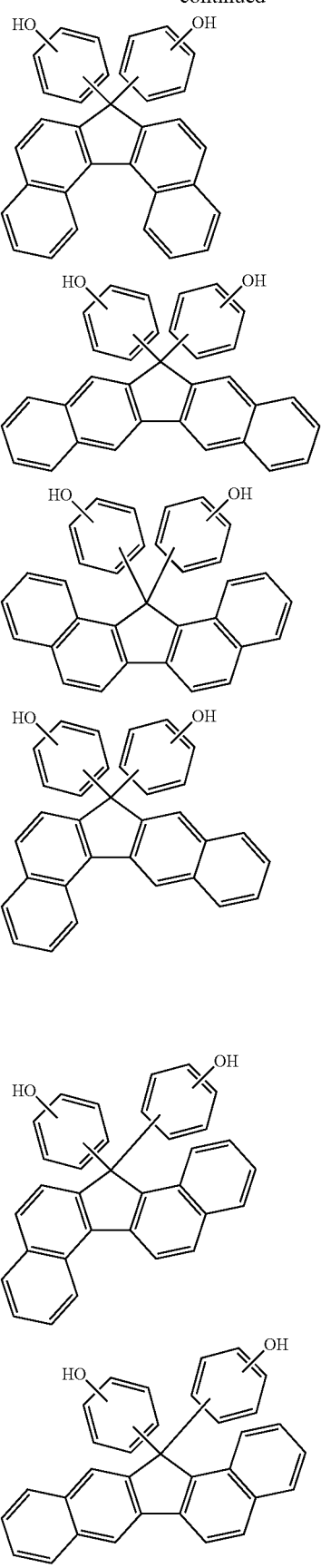

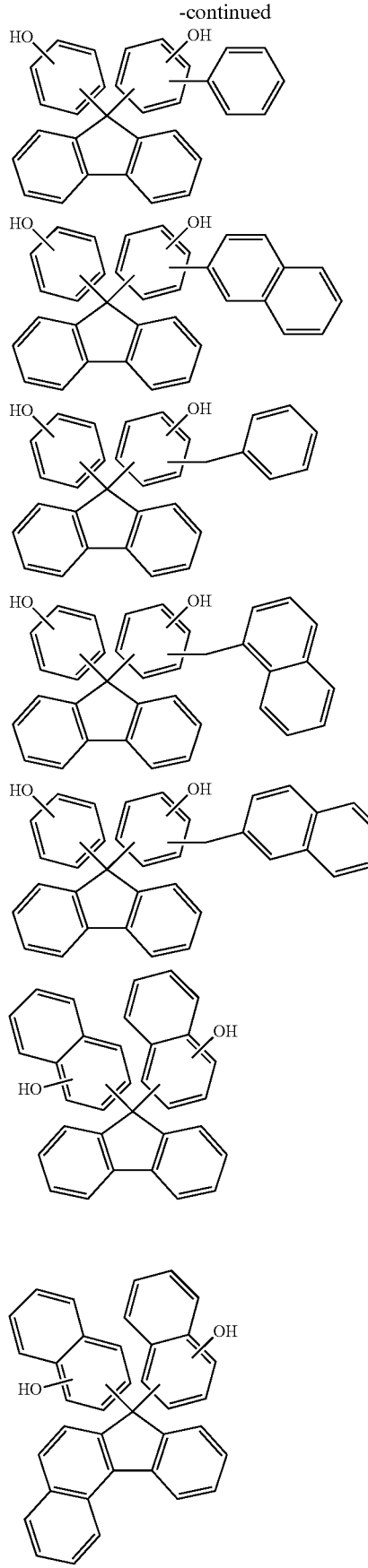
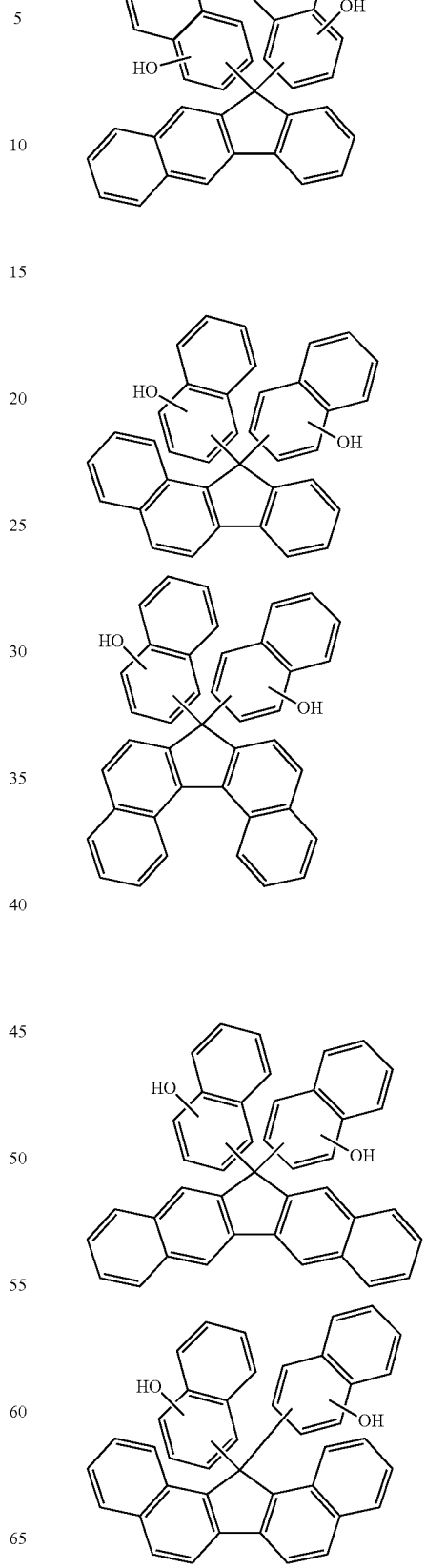

69
-continued
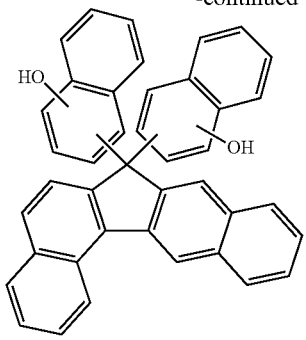
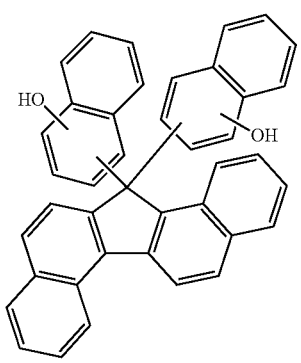
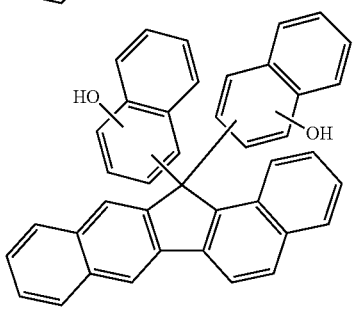
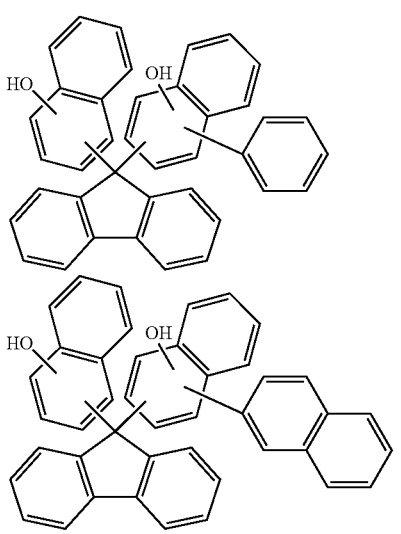
70
-continued
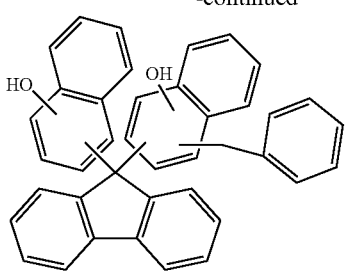
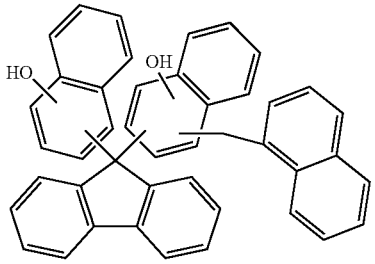
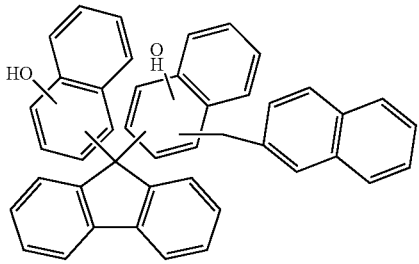
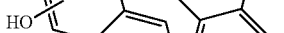
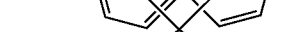
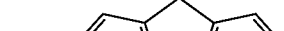

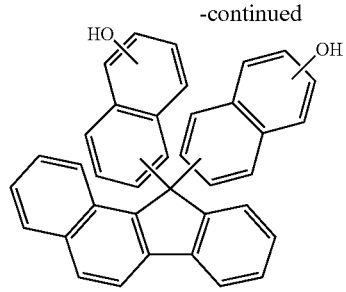
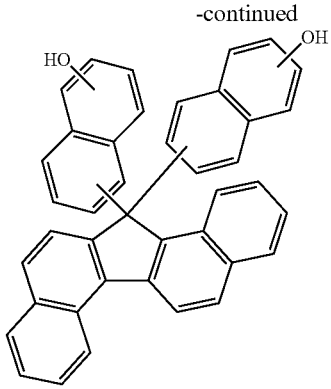
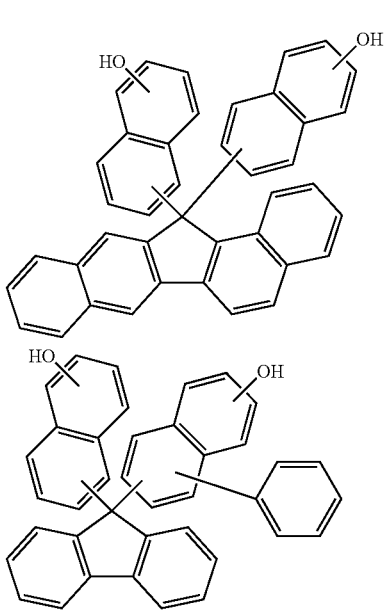
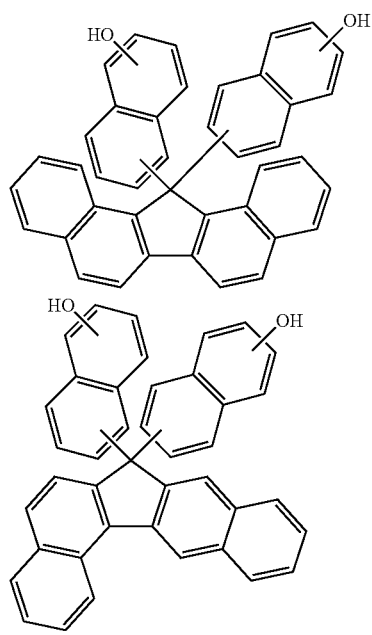

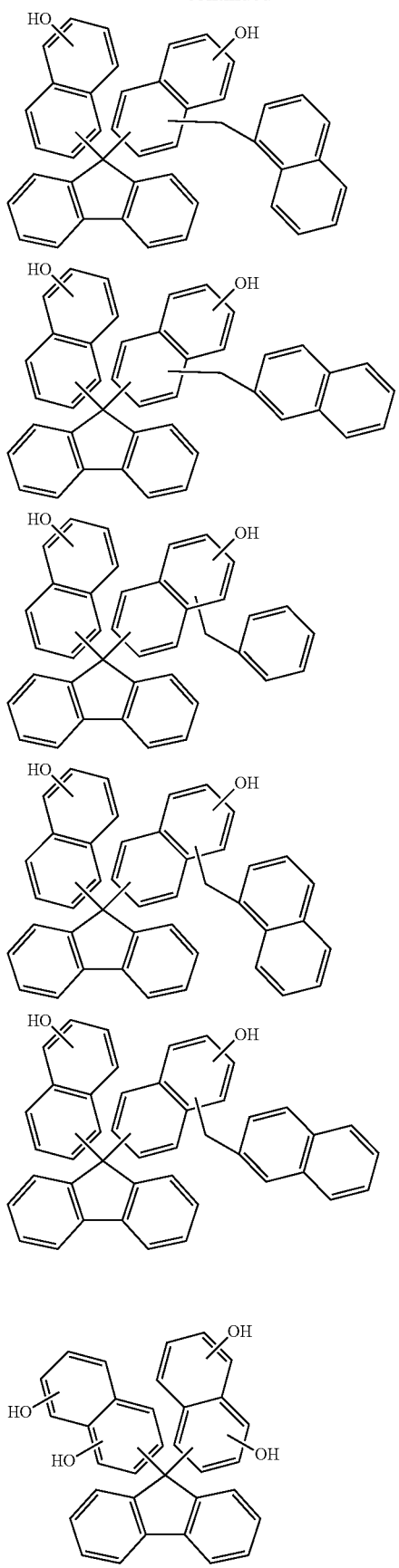
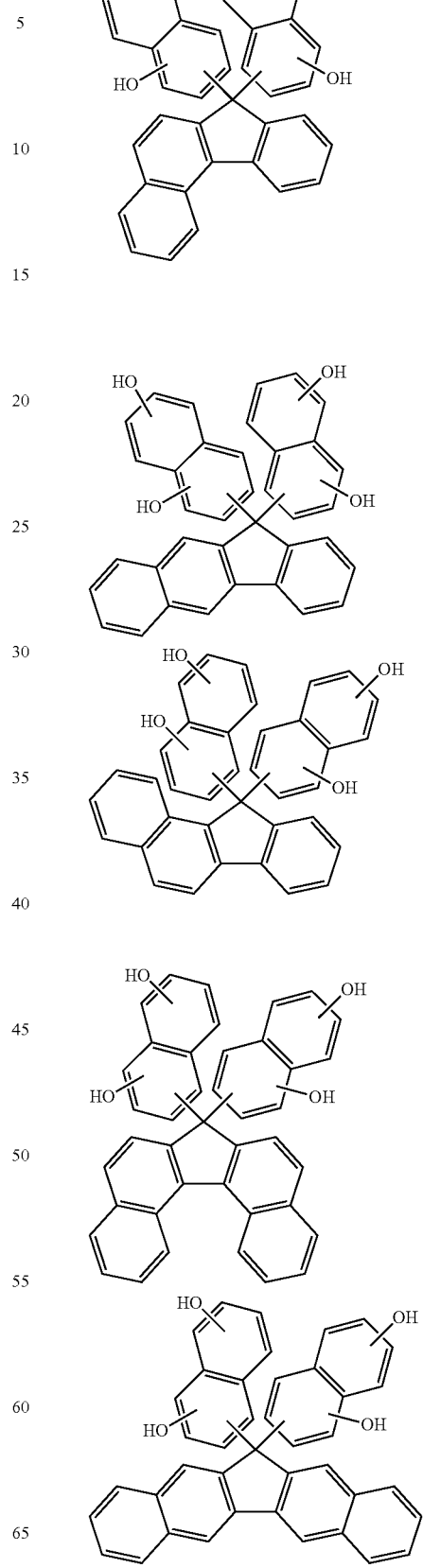

75
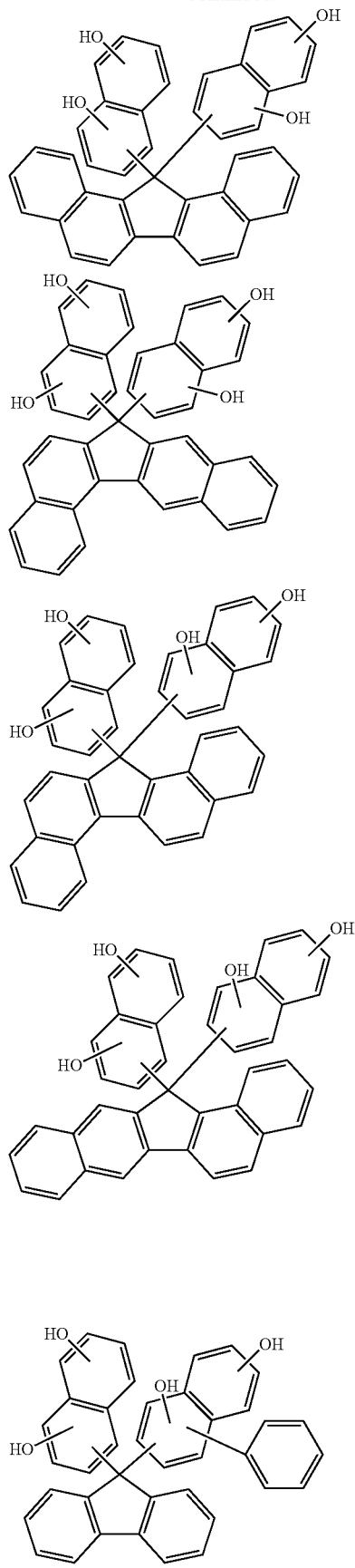
76
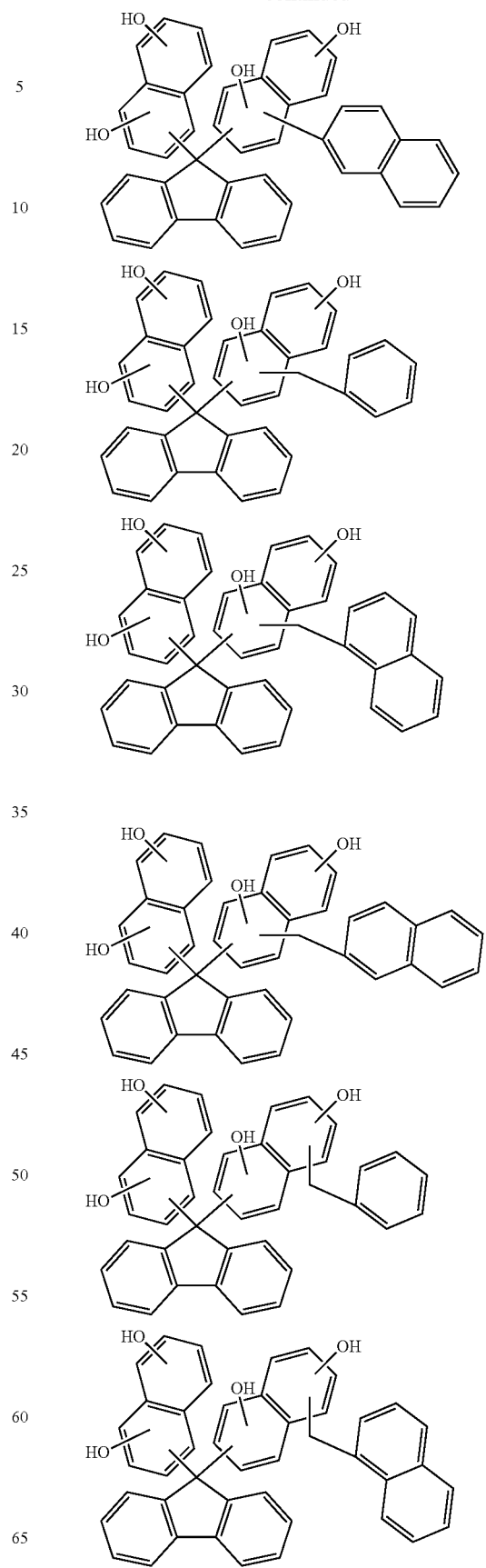

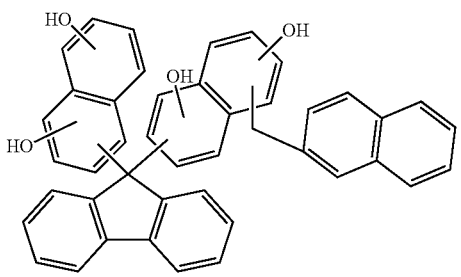

The compound contains a cardo structure of quaternary carbon, whereby it contains an extremely high heat resistance. When an inorganic hard mask middle layer film such as a silicon oxide film, a silicon nitride film and a silicon oxynitride film on a resist underlayer film or a planarizing film for manufacturing a semiconductor apparatus by CVD or the like, high temperatures exceeding 300° C. are required particularly in the case of nitride based films, and it can be suitably used for such a use.

The compound represented by the formula (3b) may be specifically exemplified as follows. In the following formulae, Ph represents a phenyl group, and hereinafter the same.

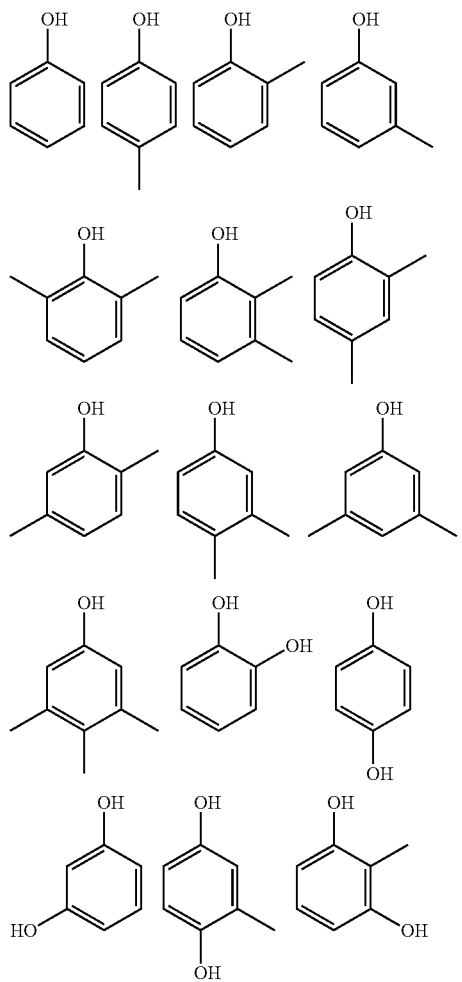

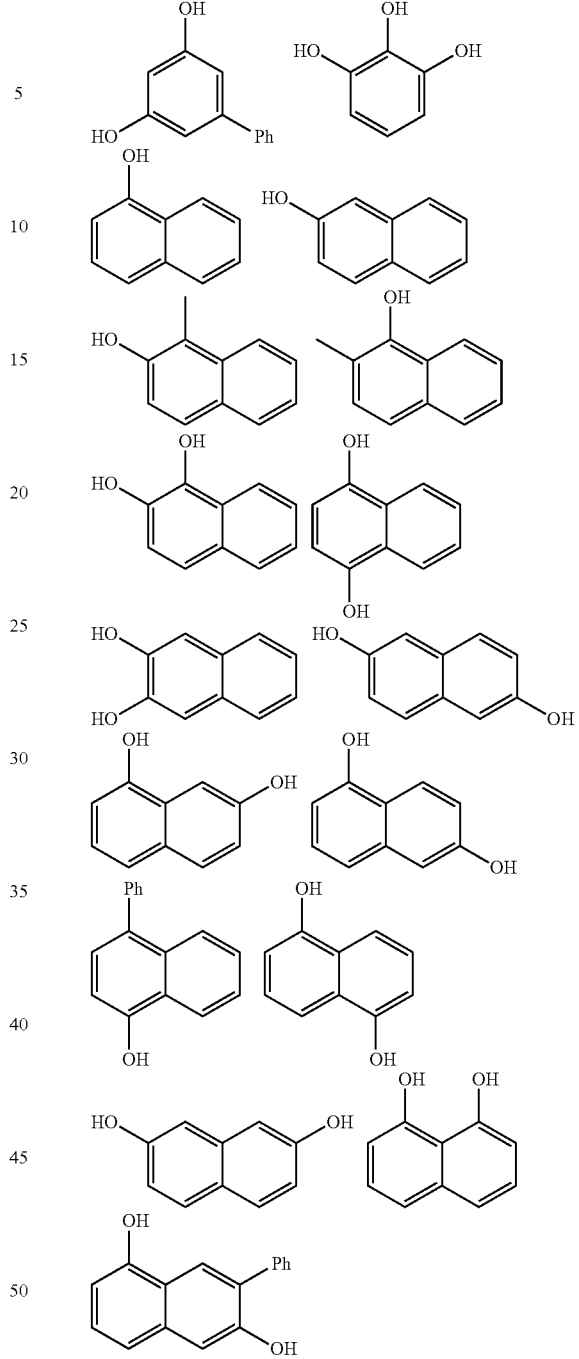

The polycondensation resin using the compound as a starting composition is excellent in thermosetting property, and dense and hard film can be formed after film formation, so that deformation at etching and heat treatment can be inhibited, and it is suitably used for various kinds of fine processing as an underlayer or a planarizing film.

The compound (aldehydes) represented by the formula (4) may be mentioned, for example, formaldehyde, acrolein, benzaldehyde, acetaldehyde, propionaldehyde, phenylacetaldehyde, α-phenylpropionaldehyde, β-phenylpropionaldehyde, o-hydroxybenzaldehyde, m-hydroxybenzaldehyde, p-hydroxybenzaldehyde, o-chlorobenzaldehyde, m-chlorobenzaldehyde, p-chlorobenzaldehyde, o-nitrobenzaldehyde, m-nitrobenzaldehyde, p-nitrobenzaldehyde, o-methylbenzaldehyde, m-methylbenzaldehyde, p-methylbenzaldehyde, p-ethylbenzaldehyde, p-n-butylbenzaldehyde, 1-naphthoaldehyde, 2-naphthoaldehyde, 6-hydroxy-2-naphthoaldehyde, 1-hydroxy-2-naphthoaldehyde and furfural, preferably formaldehyde, benzaldehyde, 1-naphthoaldehyde and 2-naphthoaldehyde.

In this case, formaldehyde can be particularly suitably used. Also, these aldehydes can be used alone or in combination of two or more kinds. An amount of the aldehydes to be used is preferably 0.2 to 5 mol, more preferably 0.5 to 2 mol based on 1 mol of the compound represented by the formulae (3a) and (3b).

As a supplying form when formaldehyde is to be used, in addition to an aqueous formaldehyde solution generally used, any compounds can be used so long as it shows the same reactivity as that of the formaldehyde during the polycondensation reaction such as paraformaldehyde, hexamethylenetetraamine, 1,3,5-trioxane, and an acetal such as formaldehyde dimethyl acetal.

Also, the resin (D-1) can be obtained by polycondensating either one or more of the compound(s) represented by the formulae (3a) and (3b), and the compound represented by the formula (4) by using an acid catalyst or a base catalyst.

The acid catalyst which can be used may be mentioned an organic acid or a mineral acid such as hydrochloric acid, nitric acid, sulfuric acid, formic acid, oxalic acid, acetic acid, methanesulfonic acid, camphorsulfonic acid, tosylic acid, trifluoromethanesulfonic acid and phosphoric acid. An amount of these acid catalysts to be used is preferably $1 \times 10^{-5}$ to $5 \times 10^{-1}$ mol based on 1 mol of the compound represented by the formula (3a) and (3b).

The base catalyst may be specifically mentioned an inorganic base or an organic base such as potassium hydroxide, sodium hydroxide, lithium hydroxide, barium hydroxide, calcium hydroxide, potassium carbonate, sodium carbonate, tetramethylammonium hydroxide, aqueous ammonia and diazabicycloundecene (DBU). An amount of these base catalysts to be used is preferably $1 \times 10^{-3}$ to $1 \times 10$ mol based on 1 mol of the compound represented by the formula (3a) and (3b).

The reaction solvent in the polycondensation of the compound represented by the formula (3a) and (3b) may be mentioned, for example, water, methanol, ethanol, propanol, butanol, isopropyl alcohol, tetrahydrofuran, dioxane, toluene, xylene, methylene chloride, dichloroethane, methyl cellosolve, methoxypropyl acetate, γ-butyrolactone, butyl cellosolve, propylene glycol monomethyl ether, or a mixed solvent thereof. These solvents are preferably used in the range of 0 to 5,000 parts by mass based on 100 parts by mass of the starting compositions of the reaction.

A reaction temperature in the polycondensation may be optionally selected depending on the reactivity of the reaction starting composition(s), and generally in the range of 0 to 200° C.

As the method of the polycondensation, there may be mentioned a method in which either one or more of the compound(s) represented by the formulae (3a) and (3b), the compound represented by the formula (4), and a reaction catalyst are charged at once, or a method in which either one or more of the compound(s) represented by the formulae (3a) and (3b), and the compound represented by the formula (4) are added dropwise in the presence of a reaction catalyst.

After completion of the polycondensation reaction, to remove unreacted starting composition(s) or reaction catalyst existing in the reaction system, a temperature of the reaction vessel is raised to 130 to 230° C., and volatile component(s) may be removed under 1 to 50 mmHg, if necessary. The catalyst or metal impurities can be removed by the usual aqueous post-treatment. As others, by adding a poor solvent and separating the poor solvent layer, starting composition(s) or low molecular weight polymer fraction(s) can be removed. Moreover, if necessary, an amount of the metal impurities can be reduced by passing through a metal-removing filter. These purification treatments may be carried out singly or may be carried out in combination of two or more kinds.

The compound(s) represented by the formulae (3a) and (3b) may be polymerized alone, or may be used two or more kinds in combination with the other compound(s) represented by the formulae (3a) and (3b).

A molecular weight of the resin (D-1) obtained by the polycondensation in terms of a polystyrene is a weight average molecular weight (Mw) of 1,000 to 30,000, particularly preferably 1,500 to 20,000. A molecular weight distribution in the range of 1.2 to 7 is preferably used.

When the organic film composition contains (D) the resin containing an aromatic ring which includes such a resin (D-1), the formed resist underlayer film or the planarizing film for manufacturing a semiconductor apparatus is excellent in filling/planarizing characteristics to the substrate, and becomes a composition having solvent resistance and heat resistance.

As (D) the resin containing an aromatic ring, a resin (D-2) having 1 or more repeating units represented by the following formula (5) is also preferably mentioned,

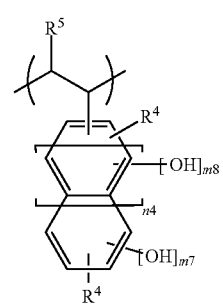

(5)

wherein each $R^4$ independently represent a hydrogen atom or a saturated or unsaturated hydrocarbon group having 1 to 20 carbon atoms; $R^5$ represents a hydrogen atom or may form a ring by bonding with one of $R^4$, and when $R^4$ and $R^5$ are bonded to form a ring, —$R^4$—$R^5$— represents a single bond or an alkylene group having 1 to 3 carbon atoms; m7+m8 represents 0, 1 or 2; and n4 represents 0 or 1.

The repeating unit represented by the formula (5) may be specifically exemplified by the following.

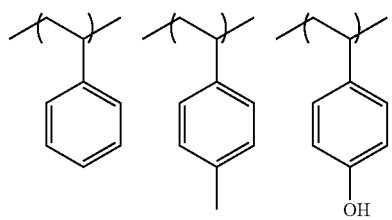

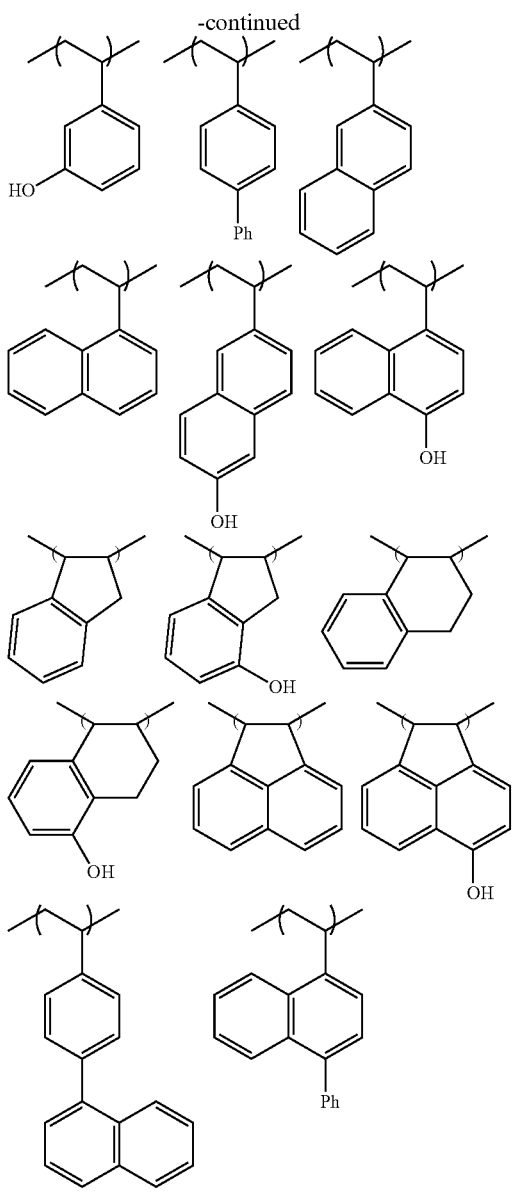

The resin (D-2) having the repeating unit can be made a high carbon density, so that it is excellent in etching resistance, whereby particularly suitably used for fine processing by etching.

Also, the resin (D-2) can be obtained by applying one or two or more kinds of a monomer(s) containing a polymerizable olefin compound corresponding to a repeating unit represented by the formula (5) or a protected product thereof to addition polymerization, and deprotecting the resulting product, if necessary. The addition polymerization can be carried out by the conventional manner such as radical polymerization, anion polymerization, and cation polymerization.

For example, in the case of the radical polymerization, it is generally carried out by mixing a monomer(s) and a radical initiator in a solvent or without solvent, and heating the mixture.

The radical initiator used may be mentioned an azo compound such as azobisisobutyronitrile and dimethyl azobisisobutyrate, and a peroxide such as benzoyl peroxide.

As a method of mixing, a suitable method can be selected depending on the design of the polymer, and there may be mentioned, for example, a mixing method in a lump, a method in which a monomer(s) and a radical initiator are mixed and the mixture is gradually added to a heated solvent, or a method in which a monomer(s) and a radical initiator are each separately added to a heated solvent, and either of which method can be used in the present invention.

An amount of the radical initiator is preferably $1 \times 10^{-5}$ to $5 \times 10^{-1}$ mol based on 1 mol of the monomer. Also, at the time of the polymerization, a chain transfer agent such as octanethiol, 3-mercaptopropionic acid and 2-mercaptoethanol may be co-presented for the purpose of controlling the molecular weight or improving the yield.

The reaction solvent when a solvent is used in the radical polymerization may by mentioned, for example, water, methanol, ethanol, propanol, butanol, isopropyl alcohol, tetrahydrofuran, dioxane, toluene, xylene, methylene chloride, dichloroethane, methyl cellosolve, methoxypropyl acetate, γ-butyrolactone, butyl cellosolve, propylene glycol monomethyl ether, 2-butanone, methyl isobutyl ketone, cyclohexanone, propylene glycol monomethyl ether acetate or a mixed solvent thereof. An amount of these solvents is preferably in the range of 0 to 5,000 parts by mass based on 100 parts by mass of the starting compositions. A reaction temperature may be optionally selected depending on reactivities of starting compositions and a decomposition temperature of the initiator, and generally in the range of 0 to 100° C.

After completion of the polymerization reaction, impurities such as a metal can be removed by the usual aqueous post-treatment. By adding a poor solvent and subsequently separating the poor solvent layer, starting composition(s) or low molecular weight polymer fraction(s) can be removed. Moreover, if necessary, an amount of the metal impurities can be reduced by passing through a metal-removing filter. These purification treatments may be carried out singly or may be carried out in combination of two or more kinds.

The polymerizable olefin compound corresponding to a repeating unit represented by the formula (5) or a protected product thereof may be polymerized alone, or may be polymerized two or more kinds, or may be polymerized further in combination with the other known polymerizable olefin monomer(s).

A molecular weight of the resin (D-2) in terms of a polystyrene is preferably a weight average molecular weight (Mw) of 1,000 to 100,000, particularly preferably 1,500 to 50,000. A molecular weight distribution thereof preferably used is in the range of 1.2 to 7.

As the other resins than (D) the resin containing an aromatic ring, resins described in paragraphs (0028) to (0029) of JP 2006-227391A can be used.

Also, the organic film composition obtained by the present invention preferably contains (E) a compound containing a phenolic hydroxyl group, if necessary. Such (E) a compound containing a phenolic hydroxyl group may be preferably a compound represented by the formula (3a) or (3b). Also used are phenol, o-cresol, m-cresol, p-cresol, 2,3-dimethylphenol, 2,5-dimethylphenol, 3,4-dimethylphenol, 3,5-dimethylphenol, 2,4-dimethylphenol, 2,6-dimethylphenol, 2,3,5-trimethylphenol, 3,4,5-trimethylphenol, 2-t-butylphenol, 3-t-butylphenol, 4-t-butylphenol, 2-phenylphenol, 3-phenylphenol, 4-phenylphenol, 3,5-diphenylphenol, 2-naphthylphenol, 3-naphthylphenol, 4-naphthylphenol, 4-tritylphenol, resorcinol, 2-methylresorcinol, 4-methylresorcinol, 5-methylresorcinol, catechol, 4-t-butylcatechol, 2-methoxyphenol, 3-methoxyphenol, 2-propylphenol, 3-propylphenol, 4-propylphenol, 2-isopropylphenol, 3-isopropylphenol, 4-isopropylphenol, 2-methoxy-5-methylphenol, 2-t-butyl-5-methylphenol, pyrogallol, thymol, isothymol, 1-naphthol, 2-naphthol, 1-anthracenol, 1-pyrenol and 9-phenanthrenol.

When the organic film composition contains (E) the compound containing a phenolic hydroxyl group, filling/planarizing characteristics can be further improved in some cases.

Into the organic film composition, (F) an acid generator and (G) a cross-linking agent can be added to further promote a thermal cross-linking reaction.

In (F) the acid generators, there are one generating an acid by thermal decomposition and one generating an acid by light irradiation, and any one can be added. Specifically, compositions described in paragraphs (0061) to (0085) of JP 2007-199653A can be added.

As (G) the cross-linking agent usable for the organic film composition, compositions described in paragraphs (0055) to (0060) of JP 2007-199653A can be added.

Further, into the organic film composition, (H) a surfactant can be added to improve coatability in spin coating. The surfactant can be used those described in paragraphs (0142) to (0147) of JP 2009-269953A.

As (I) an organic solvent usable in the organic film composition, it is not specifically limited so long as it can dissolve the compound represented by the formula (1) of Component (A), the compound having a partial structure represented by the formula (2) of Component (B), the polymer compound containing the compound of the formula (2) as a part of the repeating unit of Component (C), and the resin containing an aromatic ring (D), and those which can also dissolve (E) a compound containing a phenolic hydroxyl group, (F) an acid generator, (G) a cross-linking agent and (H) a surfactant are preferred. Specifically, the solvents described in paragraphs (0091) to (0092) of JP 2007-199653A can be added. Of these, propylene glycol monomethyl ether acetate, propylene glycol monomethyl ether, 2-heptanone, cyclopentanone, cyclohexanone, γ-butyrolactone, and a mixture of two or more kinds of these compositions are preferably used.

Furthermore, into the organic film composition, a basic compound can be blended to improve storage stability. The basic compound acts as a quencher to an acid to prevent trace of the acid generated from the acid generator from proceeding with a cross-linking reaction. Specifically, compositions described in paragraphs (0086) to (0090) of JP 2007-199653A can be added as such a basic compound.

Also, into the organic film composition, an additive to further improve filling/planarizing characteristics may be added in addition to the compositions.

The additive is not particularly limited so long as it provides filling/planarizing characteristics, and preferably used are, for example, a liquid state additive having a polyethylene glycol or polypropylene glycol structure, or, a thermo-decomposable polymer having a weight loss ratio between 30° C. and 250° C. of 40% by mass or more and a weight average molecular weight of 300 to 200,000. The thermo-decomposable polymer preferably contains a repeating unit having an acetal structure represented by the following formula (DP1) or (DP2):

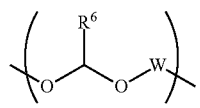
(DP1)

wherein $R^6$ represents a hydrogen atom or a saturated or unsaturated monovalent organic group having 1 to 30 carbon atoms which may be substituted; and W represents a saturated or unsaturated divalent organic group having 2 to 30 carbon atoms.

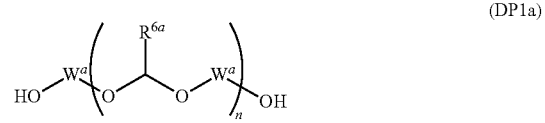
(DP1a)

wherein $R^{6a}$ represents an alkyl group having 1 to 4 carbon atoms; $W^a$ represents a saturated or unsaturated divalent hydrocarbon group having 4 to 10 carbon atoms, which may have an ether bond; and n represents an average repeating unit number and is 3 to 500.

In the process for forming an organic film, the organic film composition is coated onto a substrate to be processed by a method such as spin coating method. Adopting the spin coating method, etc., allows for obtainment of an excellent filling property. After spin coating, baking thereof is conducted in order to evaporate the solvent, to prevent mixing of the composition with a resist upper layer film or a resist middle layer film, and to promote a cross-linking reaction. The baking is conducted at a temperature in the range of 100° C. or higher and 600° C. or lower, for 10 to 600 seconds, preferably for 10 to 300 seconds. The baking temperature is more preferably 200° C. or higher and 500° C. or lower. In consideration of affections on device damage and wafer deformation, the upper limit of the heating temperature in a wafer process of lithography is preferably 600° C. or lower, more preferably 500° C. or lower.

Further, in the process for forming an organic film, the organic film composition is coated on a substrate to be processed by a spin coating method as mentioned above, and the composition is baked in an atmosphere with an oxygen concentration of 0.1% or more and 21% or less to be cured, thereby forming an organic film.

The organic film composition is based in such an oxygen atmosphere, thereby enabling to obtain a fully cured film.

Baking atmosphere may be air, and inert gas such as $N_2$, Ar and He may be filled. Also, a baking temperature, etc., may be employed as mentioned above.

Such a process for forming an organic film can provide a flat cured film irrespective of unevenness of the substrate to be processed due to its excellent filling/planarizing characteristics, so that it is extremely useful for forming a flat cured film on a substrate having a structural composition or step(s) with a height of 30 nm or more.

Incidentally, a thickness of the organic film such as the resist underlayer film or the planarizing film for manufacturing a semiconductor apparatus can be optionally selected, and generally 30 to 20,000 nm, particularly preferably 50 to 15,000 nm.

The organic film composition is extremely useful as a resist underlayer film composition of a multilayer resist process such as a two-layer resist process, a three-layer resist process using a silicon-containing middle layer film, and a four-layer resist process using a silicon-containing inorganic hard mask middle layer film and an organic antireflection film.

The present invention provides a patterning process which is a process for forming a pattern on a substrate to be processed by using such a resist underlayer film composition, which comprises, at least, forming a resist underlayer film on a substrate to be processed by using the organic film composition; forming a resist middle layer film composition on the resist underlayer film by using a resist middle layer film composition containing a silicon atom; forming a resist upper layer film on the resist middle layer film by using a resist upper layer film composition comprising a photoresist composition, to form a multilayer resist film; conducting exposure of a pattern circuit region of the resist upper layer film and then developing it by a developer to form a resist pattern on the resist upper layer film; etching the resist middle layer film by using the pattern-formed resist upper layer film as an etching mask; etching the resist underlayer film by using the pattern-formed resist middle layer film as an etching mask; and etching the substrate to be processed by using the pattern-formed resist underlayer film as an etching mask, to form a pattern on the substrate to be processed.

The silicon-containing resist middle layer of the three-layer resist process shows etching resistance to an oxygen gas or a hydrogen gas, so that it is preferred to carry out the etching of the resist underlayer film using the resist middle layer film as a mask under an etching gas mainly comprising an oxygen gas or a hydrogen gas.

As the silicon-containing resist middle layer film in the three-layer resist process, a polysilsesquioxane-based middle layer film is also preferably used. This makes the resist middle layer film to possess an antireflective effect, thereby enabling to restrict reflection. Particularly, when a composition configured to contain many aromatic groups so as to possess a higher resistance against substrate-etching is used as a resist underlayer film for 193 nm exposure, a k value is rather increased to increase a substrate reflection. Nonetheless, the reflection is restricted by the resist middle layer film, thereby enabling to restrict the substrate reflection down to 0.5% or less. Preferably used as the resist middle layer film having an antireflective effect is a polysilsesquioxane, which has a pendant anthracene for exposure of 248 nm or 157 nm, or a pendant phenyl group or a pendant light-absorbing group having a silicon-silicon bond for 193 nm exposure, and which is cross-linked by an acid or a heat.

In this case, formation of a silicon-containing resist middle layer film by the spin coating method is easy and convenient than that by the CVD method so that it has a merit in a cost.

Further, an inorganic hard mask middle layer film may be formed as a middle layer film. In this case, the process comprises the steps of, at least, forming a resist underlayer film on the substrate to be processed by using the organic film composition; forming an inorganic hard mask middle layer film selected from any one of a silicon oxide film, a silicon nitride film and a silicon oxynitride film on the resist underlayer film; forming a resist upper layer film on the inorganic hard mask middle layer film by using a resist upper layer film composition comprising a photoresist composition, to form a multilayer resist film; conducting exposure of a pattern circuit region of the resist upper layer film and then developing it by a developer to form a resist pattern on the resist upper layer film; etching the inorganic hard mask middle layer film by using the obtained resist pattern as an etching mask; etching the resist underlayer film by using the obtained pattern-formed inorganic hard mask middle layer film as an etching mask; and etching the substrate to be processed by using the obtained resist underlayer film as an etching mask, to form a pattern on the substrate to be processed.

As mentioned above, when the inorganic hard mask middle layer film is formed on the resist underlayer film, a silicon oxide film, a silicon nitride film and a silicon oxynitride film (SiON film) are formed by the CVD method or the ALD method. The method for forming a nitride film is described in, for example, JP 2002-334869A and WO2004/066377. A film thickness of the inorganic hard mask middle layer film is 5 to 200 nm, preferably 10 to 100 nm, and in particular, a SiON film which has high effects as an antireflection film is most preferably used. A temperature of the substrate in forming the SiON film is raised up to 300° C. to 500° C., so that it is necessary to endure the temperature of 300° C. to 500° C. as the underlayer. The organic film composition to be used in the present invention has high heat resistance, and endures the high temperature of 300° C. to 500° C., so that the inorganic hard mask formed by the CVD method or the ALD method, and the resist underlayer film formed by the spin coating method can be used in combination.

Further, the present invention can be suitably used for a four-layer resist process using an organic antireflection film. In this case, the process comprises the steps of, at least, forming a resist underlayer film on the substrate to be processed by using the organic film composition; forming an inorganic hard mask middle layer film selected from any one of a silicon oxide film, a silicon nitride film and a silicon oxynitride film on the resist underlayer film; forming an organic antireflection film on the inorganic hard mask middle layer film; forming a resist upper layer film on the organic antireflection film by using the resist upper layer film composition comprising a photoresist composition, to form a multilayer resist film; conducting exposure of a pattern circuit region of the resist upper layer film and then developing it by a developer to form a resist pattern on the resist upper layer film; etching the organic antireflection film and the inorganic hard mask middle layer film by using the obtained resist pattern as an etching mask; etching the resist underlayer film by using the obtained pattern-formed inorganic hard mask middle layer film as an etching mask; and etching the substrate to be processed by using the obtained pattern-formed resist underlayer film as an etching mask, to form a pattern on the substrate to be processed.

Although it may form a photoresist film on the inorganic hard mask middle layer film as a resist upper layer film as mentioned above, it is also possible to form an organic antireflection film (BARC) on the inorganic hard mask middle layer film by spin coating, and a photoresist film may be formed thereon. In particular, when a SiON film is used as the inorganic hard mask middle layer film, it is possible to restrict reflection by virtue of the two-layer antireflective films of the SiON film and the BARC film, even by a liquid immersion exposure at a higher NA exceeding 1.0. Another merit of the formation of the BARC resides in obtainment of an effect to reduce footing (trailing) of a photoresist pattern compared to a photoresist pattern just above the SiON film.

The resist upper layer film in the three-layer resist film may be a positive type or a negative type, and it is possible to use therefor the same one as a typically used photoresist composition. When the monolayer resist upper layer film is formed by the photoresist composition, spin coating method is preferably used similarly to the case for forming the resist underlayer film. Prebaking is to be conducted after spin coating of the photoresist composition, preferably at 60 to 180° C. for 10 to 300 seconds. Thereafter, exposure is to be conducted according to a usual manner, followed by post-exposure baking (PEB) and development, to thereby obtain a resist pattern. Although a thickness of the resist upper layer film is not particularly limited, it is preferably 30 to 500 nm, particularly preferably 50 to 400 nm.

Further, examples of light for exposure include high energy beams at wavelengths of 300 nm or shorter, specifically excimer lasers at 248 nm, 193 nm, and 157 nm, soft X-rays at 3 to 20 nm, an electron beam, X-rays, and the like.

Next, etching is to be conducted by using the obtained resist pattern as a mask. In a three-layer process, etching of a resist middle layer film or an inorganic hard mask middle layer film is to be conducted by using the resist pattern as a mask and by adopting a fluorocarbon-based gas.

Then, etching processing of the resist underlayer film is to be conducted by using the pattern-formed resist middle layer film or the pattern-formed inorganic hard mask middle layer film as a mask.

The subsequent etching of a substrate to be processed can be also conducted according to a usual manner, for example, the manner that etching mainly based on a fluorocarbon-based gas is conducted when the substrate to be processed is made of $SiO_2$, SiN or silica-based low dielectric constant insulating film, or etching mainly based on a chlorine-based or bromine-based gas is conducted for a substrate made of p-Si, Al or W. When substrate processing is conducted by etching by a fluorocarbon-based gas, the silicon-containing middle layer of the three-layer process is stripped simultaneously with the substrate processing. In the case of etching of a substrate by a chlorine-based gas or a bromine-based gas, stripping of the silicon-containing middle layer is required to be separately conducted by dry etching stripping by a fluorocarbon-based gas after the substrate processing.

The resist underlayer film is characterized in that the film is excellent in etching resistance at the time of etching these substrates to be processed.

It is noted that the substrate to be processed is not particularly limited, and a substrate made of Si, α-Si, p-Si, $SiO_2$, SiN, SiON, W, TiN or Al, or a composition in which a layer to be processed is formed on the substrate may be used. Examples of the layer to be processed to be used include various Low-k films made of Si, $SiO_2$, SiON, SiN, p-Si, α-Si, W, W—Si, Al, Cu or Al—Si, and stopper films therefor, which can each typically form into a thickness of 50 to 10,000 nm, particularly 100 to 5,000 nm. When the layer to be processed is to be formed, the composition of the substrate to be used is different from those of the layers to be processed.

An example of the three-layer resist process will be specifically explained by referring to FIGS. 1A-1F as follows.

In the case of the three-layer resist process, as shown in FIG. 1A, the process is configured to form a resist underlayer film 3 by using the organic film composition on a layer to be processed 2 laminated on a substrate 1, to thereafter form a resist middle layer film 4 thereon, and to form a resist upper layer film 5 thereon.

Figure 1B:
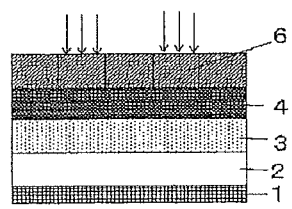
Figure 1C:
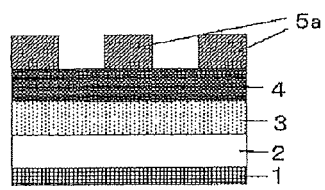
Figure 1D:
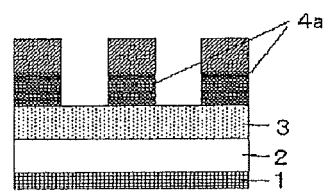
Figure 1E:
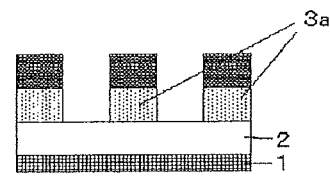
Figure 1F:
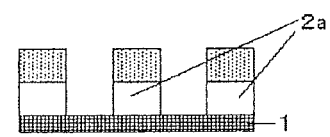

Next, as shown in FIG. 1B, exposure is conducted for required portions 6 of the resist upper layer film, followed by PEB and development, to for a resist pattern 5a (FIG. 1C). The thus obtained resist pattern 5a is then used as a mask, etching of the resist middle layer film 4 is conducted by using a CF-based gas to form a pattern-formed resist middle layer film 4a (FIG. 1D). After removing the resist pattern 5a, the obtained pattern-formed resist middle layer film 4a is used as a mask, etching of the resist underlayer film 3 is conducted by using an oxygen plasma to form a pattern-formed resist underlayer film 3a (FIG. 1E). Further, after removing the pattern-formed resist middle layer film 4a, the pattern-formed resist underlayer film 3a is used as a mask, etching of the layer to be processed 2 is conducted to form a pattern 2a (FIG. 1F).

When an inorganic hard mask middle layer film is used, the resist middle layer film 4 is the inorganic hard mask middle layer film, and when a BARC is to be arranged, a BARC layer is provided between the resist middle layer film 4 and the resist upper layer film 5. Etching of the BARC may be continuously conducted prior to etching of the resist middle layer film 4, or etching of the BARC alone may be conducted and subsequently etching of the resist middle layer film 4 may be conducted by changing an etching apparatus.

EXAMPLES

In the following, the present invention is explained in more detail by referring to Examples and Comparative Examples, but the present invention is not limited by these descriptions.

Incidentally, the measurement method of the molecular weight is carried out specifically by the following mentioned method. A weight average molecular weight (Mw) and a number average molecular weight (Mn) calculated on a polystyrene using gel permeation chromatography (GPC) and tetrahydrofuran as an eluent were obtained and a polydispersity (Mw/Mn) was calculated.

[Synthetic Example 1] Synthesis of Compound (I)

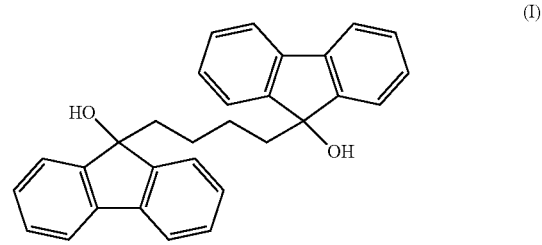 [SMILES: OC1(CCCCC2(O)c3ccccc3-c3ccccc32)c2ccccc2-c2ccccc21]

(I)

Under nitrogen atmosphere, in 1 L four-necked flask equipped with a thermometer and a reflux condenser was prepared 300 ml of 0.67 mol/L 1,4-tetramethylenebis(magnesium chloride)/tetrahydrofuran solution. To the solution was added dropwise 230.8 g of a tetrahydrofuran solution containing 25 wt % of 9-fluorenone at an inner temperature of 40° C., and after heating in an oil bath at 60° C. for 3 hours, the reaction was stopped by adding 500 ml of a saturated aqueous ammonium chloride solution. To the mixture were added 400 ml of pure water, 200 ml of tetrahydrofuran and 500 ml of hexane, and the resulting mixture was stirred. At this time, the solution became yellowish white suspension. The suspension was collected by filtration using a Hirsch funnel, the precipitated crystals were washed with pure water until the filtrate became neutral, and then, washed twice with 300 ml of hexane/tetrahydrofuran=4/1 (volume ratio). The resulting crystal was vacuum dried at 60° C. to obtain 16.7 g of Compound (I) with a yield of 24.9% and a GPC purity of 91.7%.

Compound (I):

IR (ATR method): ν=3288, 3065, 3039, 2933, 2861, 1608, 1586, 1466, 1447, 1376, 1315, 1285, 1248, 1194, 1156, 1106, 1072, 1031, 952, 940, 829, 777, 739, 732 $cm^{-1}$.

$^1$H-NMR (600 MHz in DMSO-d$_6$): δ=0.59 (4H, m), 1.77 (4H, m), 5.38 (2H, —OH), 7.22 (4H, t), 7.29 (4H, t), 7.35 (4H, d), 7.66 (4H, d) ppm.

$^{13}$C-NMR (150 MHz in DMSO-d$_6$): δ=23.83, 39.63, 80.93, 119.69, 123.43, 127.48, 128.09, 139.00, 149.62 ppm.

[Synthetic Example 2] Synthesis of Compound (A1)

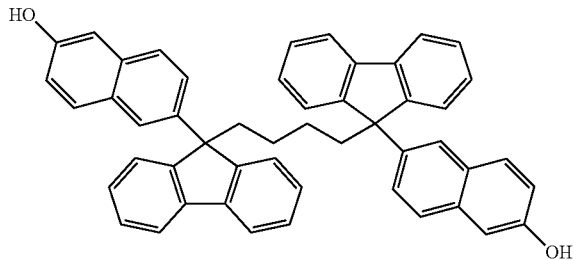

(A1)

Under nitrogen atmosphere, to 300 mL three necked flask equipped with a thermometer and a reflux condenser were added 10.0 g (23.9 mmol) of Compound (I), 6.9 g (47.9 mmol) of 2-naphthol and 60 ml of 1,2-dichloroethane, and the mixture was stirred in an oil bath at 30° C. to prepare a dispersion. To the dispersion was gradually added 3.0 ml of methanesulfonic acid, and the reaction was carried out in an oil bath at 30° C. for 58 hours, and in an oil bath at 50° C. for 24 hours. After cooling to room temperature, 50 g of pure water was added to the mixture, and insoluble composition was separated by filtration using a Hirsch funnel. The filtrate was recovered and washed with 300 ml of ethyl acetate, and transferred to a separating funnel. Separating the liquids and washing with water were carried out until the aqueous layer became neutral, and then, the organic layer was evaporated by an evaporator to obtain yellow crystal. The obtained yellow crystal was recrystallized from 500 ml of hexane:1, 2-dichloroethane=3:2 (volume ratio), collected by filtration using a Hirsch funnel, and further washed twice with 200 ml of hexane:1,2-dichloroethane=2:1 (volume ratio). The crystal was recovered and vacuum dried at 60° C. to obtain 4.4 g of Compound (A1) with a yield of 27.5% and a GPC purity of 89.4%.

Compound (A1):

IR (ATR method): ν=3527, 3056, 2932, 2856, 1704, 1634, 1603, 1506, 1475, 1446, 1376, 1347, 1278, 1215, 1175, 1145, 1032, 952, 895, 861, 807, 769, 754, 738 cm$^{-1}$.

$^1$H-NMR (600 MHz in DMSO-d$_6$): δ=0.49 (4H, m), 2.31 (4H, t), 6.58 (2H, d-d), 6.93 (2H, s-d), 6.98 (2H, d-d), 7.16 (4H, d), 7.22 (4H, t-d), 7.30 (2H, d), 7.34 (4H, t-d), 7.64 (2H, d), 7.73 (s-d), 7.86 (4H, d), 9.60 (2H, —OH) ppm.

$^{13}$C-NMR (150 MHz in DMSO-d$_6$): δ=24.27, 36.62, 58.10, 108.15, 118.39, 120.08, 123.90, 124.17, 125.75, 125.78, 127.19, 127.51, 127.65, 129.32, 133.05, 138.86, 140.25, 151.28, 155.07 ppm.

TG-DTA (−5% weight loss temperature, in Air): 263° C.

TG-DTA (−5% weight loss temperature, in He): 282° C.

DSC (Glass transition temperature): 107° C.

[Synthetic Example 3] Synthesis of Compound (II)

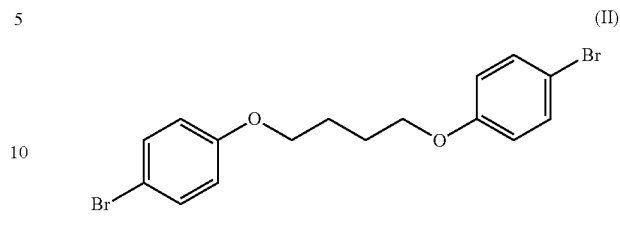

(II)

Under nitrogen atmosphere, in a 3 L four necked flask equipped with a thermometer and a reflux condenser were weighed 300 g (1734.0 mmol) of 4-bromophenol, 19.8 g (86.9 mmol) of benzyltriethylammonium chloride, 333 g of 25% aqueous sodium hydroxide solution and 1000 ml of tetrahydrofuran, and the mixture was heated in an oil bath at 60° C. To the mixture was added dropwise 176.0 g (81.5 mmol) of 1,4-dibromobutane previously diluted with 100 g of tetrahydrofuran from a dropping funnel over 30 minutes, and the mixture was heated under reflux for 39 hours. The reaction mixture was diluted with 1000 ml of toluene, cooled to room temperature by allowing to stand and transferred to a separating funnel. The aqueous layer was disposed, the organic layer was further washed twice with 500 g of 5% aqueous sodium hydroxide solution, and separation of the liquids and washing with water were repeated until the aqueous layer became neutral. The organic layer was recovered and dried over anhydrous sodium sulfate, then, the drier was removed by filtration and the solvent of the filtrate was removed by using an evaporator. The crystal obtained by evaporated to dryness was recovered and vacuum dried at 45° C. to obtain 306.7 g of compound (II) with a yield of 94.0% and a GPC purity of 99.2%.

Compound (II):

IR (ATR method): ν=3091, 2957, 2927, 2874, 1878, 1636, 1588, 1575, 1486, 1466, 1445, 1408, 1387, 1316, 1299, 1287, 1240, 1199, 1170, 1116, 1102, 1071, 1050, 1001, 975, 824, 804, 744 cm$^{-1}$.

$^1$H-NMR (600 MHz in CDCL3): δ=1.96 (4H, quint), 3.99 (4H, quint), 6.77 (4H, d-t), 7.36 (4H, d-t) ppm.

$^{13}$C-NMR (150 MHz in CDCL3): δ=25.86, 67.63, 112.76, 116.24, 132.23, 158.02 ppm.

[Synthetic Example 4] Synthesis of Compound (III)

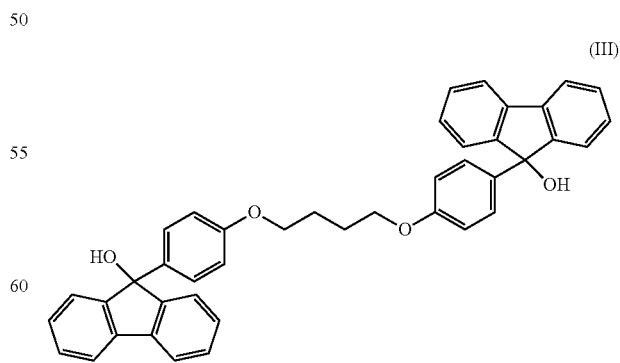

(III)

Under nitrogen atmosphere, in a 2000 ml four necked flask equipped with a thermometer and a reflux condenser was weighed 38.0 g (95.0 mmol) of Compound (II), 300 ml of tetrahydrofuran was added thereto to prepare a uniform solution. The flask was cooled with acetonitrile-dry ice refrigerant, 80.4 ml of 2.6 mol/L n-butyl lithium-hexane solution was added dropwise to the solution from a dropping funnel over 30 minutes and then the mixture was stirred for 3 hours. Then, the refrigerant was changed to an ice-cooling bath and 154.0 g of 20 wt % 9-fluorenone-tetrahydrofuran solution was added dropwise to the mixture from a dropping funnel over 17 minutes. After stirring at room temperature for 4 hours, the reaction was stopped by adding 200 ml of a saturated aqueous ammonium chloride solution to the mixture. The reaction mixture was diluted with 800 ml of ethyl acetate, transferred to a separating funnel and separation of liquids and washing with water were repeated until the aqueous layer became neutral. The organic layer was recovered, and the solvent was removed by distillation until the inner composition in an evaporator became 510 g to obtain a suspension. To the obtained suspension was added dropwise 600 g of hexane under stirring to precipitate crystals. The crystals were collected by filtration using a Hirsch funnel, washed twice with 600 ml of ethyl acetate:hexane=1/2 (volume ratio) and vacuum dried at 60° C. to obtain 34.9 g of Compound (III) with a yield of 67.8% and a GPC purity of 94.4%.

Compound (III):

IR (ATR method): ν=3381, 3174, 3053, 2955, 2861, 160, 1581, 1508, 1472, 1448, 1413, 1381, 1292, 1243, 1166, 1114, 1097, 1011, 985, 947, 920, 824, 774, 752, 736 cm$^{-1}$.

$^1$H-NMR (600 MHz in DMSO-d$_6$): δ=1.78 (4H, m), 3.92 (4H, m), 6.19 (2H, —OH), 6.73 (4H, d-t), 7.11 (4H, d-t), 7.20 to 7.22 (8H, m), 7.33 (4H, m), 7.78 (4H, d) ppm.

$^{13}$C-NMR (150 MHz in DMSO-d$_6$): δ=25.38, 66.99, 82.22, 113.85, 120.00, 124.57, 126.25, 127.95, 128.33, 136.88, 139.01, 151.47, 157.42 ppm.

[Synthetic Example 5] Synthesis of Compound (A2)

Under nitrogen atmosphere, in a 1000 ml four necked flask equipped with a thermometer and a reflux condenser were weighed 50.0 g (83.0 mmol) of Compound (III) and 78.1 g (829.9 mmol) of phenol, 400 ml of 1,2-dichloroethane was added to the mixture to prepare a uniform solution in an oil bath at 50° C. To the mixture was gradually added dropwise 15.0 ml of methanesulfonic acid from a dropping funnel, and the resulting mixture was heated for 1 hour. After cooling the mixture to room temperature by allowing to stand, the reaction mixture was diluted with 600 ml of methyl isobutyl ketone, transferred to a separating funnel, and separation of the liquids and washing with water were repeated until the aqueous layer became neutral. The organic layer was recovered, and after removing the solvent by distillation until the inner composition in an evaporator became 150 g, 510 g of methanol was added dropwise to the mixture under stirring to precipitate crystals. The crystals were collected by filtration using a Hirsch funnel, washed twice with 330 ml of methanol and vacuum dried at 60° C. to obtain 52.2 g of Compound (A2) with a yield of 83.3% and a GPC purity of 92.7%.

Compound (A2):

IR (ATR method): ν=3403, 3033, 2950, 2871, 1609, 1506, 1472, 1446, 1293, 1243, 1175, 1106, 1049, 1013, 971, 915, 821, 747, 729 cm$^{-1}$.

$^1$H-NMR (600 MHz in DMSO-d$_6$): δ=1.76 (4H, m), 3.90 (4H, m), 6.62 (4H, d-t), 6.75 (4H, d-t), 6.89 (4H, d-t), 6.96 (4H, d-t), 7.26 (4H, t-d), 7.34 (8H, m), 7.87 (4H, d), 9.30 (2H, —OH) ppm.

$^{13}$C-NMR (150 MHz in DMSO-d$_6$): δ=25.35, 63.55, 66.94, 114.06, 114.92, 120.33, 125.85, 127.30, 127.66, 128.59, 128.63, 135.67, 137.68, 139.29, 151.44, 156.00, 157.20 ppm.

TG-DTA (−5% weight loss temperature, in Air): 348° C.
TG-DTA (−5% weight loss temperature, in He): 339° C.
DSC (Glass transition temperature): 112° C.

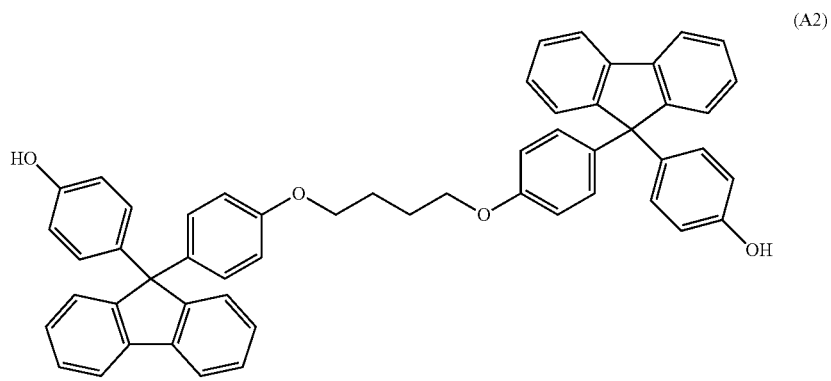 [SMILES: Oc1ccc(C2(c3ccc(OCCCCOc4ccc(C5(c6ccc(O)cc6)c6ccccc6-c6ccccc65)cc4)cc3)c3ccccc3-c3ccccc32)cc1]

(A2)

[Synthetic Example 6] Synthesis of Compound (A3)

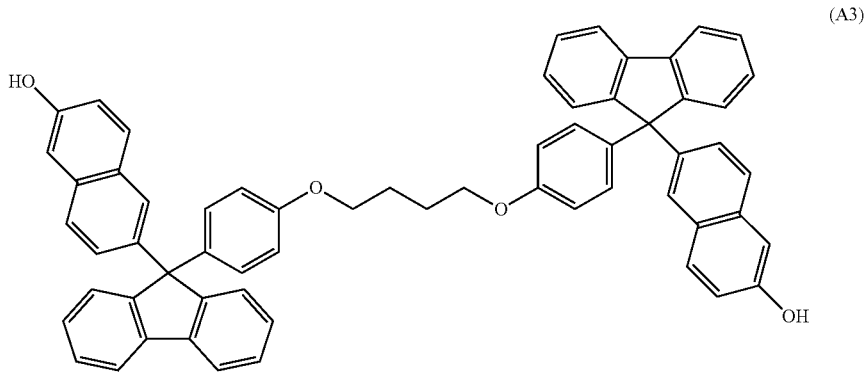 [SMILES: Oc1ccc2cc(C3(c4ccc(OCCCCOc5ccc(C6(c7ccc8cc(O)ccc8c7)c7ccccc7-c7ccccc76)cc5)cc4)c4ccccc4-c4ccccc43)ccc2c1]

(A3)

Under nitrogen atmosphere, in a 1000 ml four necked flask equipped with a thermometer and a reflux condenser were weighed 50.0 g (83.0 mmol) of Compound (III) and 95.7 g (663.7 mmol) of 2-naphthol, and 550 ml of 1,2-dichloroethane was added to the mixture to prepare a uniform solution in an oil bath at 50° C. To the mixture was gradually added dropwise 2.6 ml of methanesulfonic acid from a dropping funnel, and the mixture was heated for 2 hours. After cooling the mixture to room temperature by allowing to stand, the reaction mixture was diluted with 1000 ml of methyl isobutyl ketone, transferred to a separating funnel, and separation of the liquids and washing with water were repeated until the aqueous layer became neutral. The organic layer was recovered, and after removing the solvent by distillation until the inner composition in an evaporator became 160 g, 300 g of methanol was added to the residue. The mixture was heated to 60° C. to prepare a uniform solution, 30 g of pure water was added to the solution under stirring, and stirring at room temperature was continued to precipitate a rice cake-like lump. The supernatant was removed by decantation and the precipitate was recrystallized from 1800 g of isopropyl alcohol:water=7:3 (weight ratio). The crystals were collected by filtration using a Hirsch funnel, washed twice with 380 g of isopropyl alcohol:water 1:3 (weight ratio) and vacuum dried at 60° C. to obtain 46.6 g of Compound (A3) with a yield of 65.7% and a GPC purity of 85.2%.

Compound (A3):

IR (ATR method): ν=3526, 3055, 2964, 1634, 1605, 1578, 1504, 1474, 1446, 1390, 1289, 1277, 1245, 1179, 1120, 1013, 979, 959, 945, 898, 860, 829, 812, 752, 738 cm$^{-1}$.

$^1$H-NMR (600 MHz in DMSO-$d_6$): δ=1.77 (4H, m), 3.92 (4H, m), 6.77 (4H, d-t), 6.99 (2H, d-d), 7.02 (4H, m), 7.04 (2H, s-d), 7.19 (2H, d-d), 7.28 (4H, t), 7.34 to 7.38 (6H, m), 7.44 (2H, d), 7.52 (2H, d), 7.56 (2H, d), 7.90 (4H, d), 9.67 (2H, —OH) ppm.

$^{13}$C-NMR (150 MHz in DMSO-$d_6$): δ=25.45, 61.98, 66.96, 108.30, 114.19, 118.69, 120.45, 125.05, 125.96, 126.19, 126.85, 127.12, 127.49, 127.73, 128.72, 129.28, 133.29, 137.25, 139.44, 139.66, 151.00, 155.30, 157.32 ppm.

TG-DTA (−5% weight loss temperature, in Air): 395° C.
TG-DTA (−5% weight loss temperature, in He): 368° C.
DSC (Glass transition temperature): 138° C.

[Synthetic Example 7] Synthesis of Compound (IV)

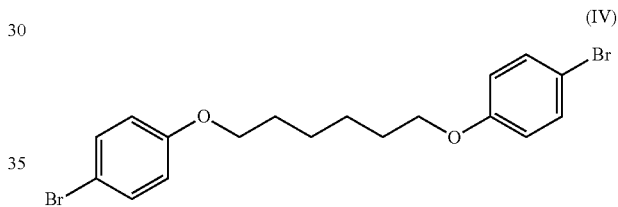

(IV)

Under nitrogen atmosphere, in a 3 L four necked flask equipped with a thermometer and a reflux condenser were charged 50.0 g (289.0 mmol) of 4-bromophenol, 3.3 g (14.5 mmol) of benzyltriethylammonium chloride, 55.5 g of 25% aqueous sodium hydroxide solution and 170 ml of tetrahydrofuran, and the mixture was heated in an oil bath at 60° C. To the mixture was added dropwise 31.7 g (129.9 mmol) of 1,6-dibromohexane previously diluted with 35 g of tetrahydrofuran from a dropping funnel over 20 minutes, and the mixture was stirred under reflux for 50 hours. After diluting the mixture with 200 ml of toluene, the mixture was cooled to room temperature by allowing to stand, and transferred to a separating funnel. The aqueous layer was disposed, the organic layer was further washed twice with 100 g of 5% aqueous sodium hydroxide solution, and separation of the liquids and washing with water were repeated until the aqueous layer became neutral. The organic layer was recovered and dried over anhydrous sodium sulfate, then, the drier was removed by filtration and the solvent of the filtrate was removed by using an evaporator. The obtained crystal is vacuum dried at 45° C. to obtain 54.0 g of Compound (IV) with a yield of 97.1% and a GPC purity of 98.2%.

Compound (IV):

IR (ATR method): ν=3091, 2942, 2910, 2864, 1885, 1637, 1589, 1576, 1490, 1474, 1398, 1290, 1248, 1175, 1119, 1105, 1076, 1025, 1001, 830, 809, 733 cm$^{-1}$.

$^1$H-NMR (600 MHz in CDCL3): δ=1.53 (4H, quint), 1.80 (4H, quint), 3.93 (4H, t), 6.77 (4H, d-t), 7.36 (4H, d-t) ppm.

$^{13}$C-NMR (150 MHz in CDCl$_3$): δ=25.78, 29.07, 68.02, 112.61, 116.25, 132.18, 158.15 ppm.

[Synthetic Example 8] Synthesis of Compound (V)

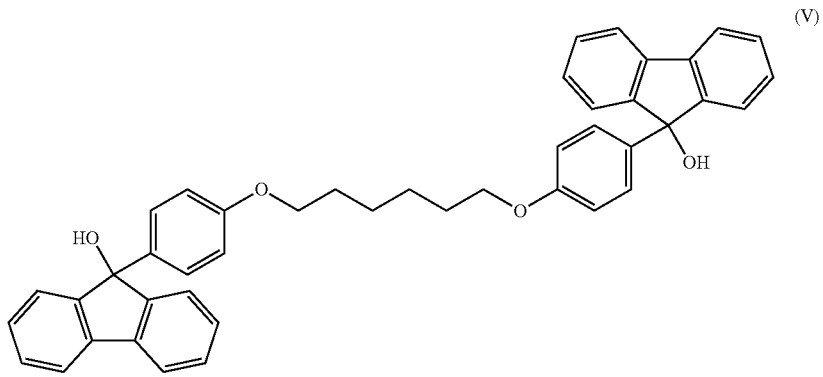 [SMILES: OC1(c2ccc(OCCCCCCOc3ccc(C4(O)c5ccccc5-c5ccccc54)cc3)cc2)c2ccccc2-c2ccccc21]

Under nitrogen atmosphere, in a 2000 ml four necked flask equipped with a thermometer and a reflux condenser was weighed 40.0 g (93.4 mmol) of Compound (IV), 300 ml of tetrahydrofuran was added thereto to prepare a uniform solution. The flask was cooled with acetonitrile-dry ice refrigerant, and to the mixture was added dropwise 79.1 ml of 2.6 mol/L n-butyl lithium-hexane solution from a dropping funnel over 20 minutes, and the mixture was stirred for 1 hour. Then, the refrigerant was changed to an ice-cooling bath and 202.0 g of 15 wt % 9-fluorenone-tetrahydrofuran solution was added dropwise to the mixture from a dropping funnel over 15 minutes. After stirring at room temperature for 19 hours, the reaction was stopped by adding 200 ml of a saturated aqueous ammonium chloride solution to the mixture. The reaction mixture was diluted with 600 ml of ethyl acetate, transferred to a separating funnel and separation of liquids and washing with water were repeated until the aqueous layer became neutral. The organic layer was recovered, and after removing the solvent by distillation until the inner composition in an evaporator became 196 g, and 589 g of hexane was added to the mixture under stirring to precipitate a rice cake-like lump. The supernatant was removed by decantation and 50 g of ethyl acetate was added again to the residue to prepare a uniform solution, and 472 g of hexane was added to the mixture under stirring to precipitate a rice cake-like lump again. The supernatant was removed by decantation and the precipitate was recrystallized from 215 g of ethyl acetate/isopropyl alcohol=1/6 (weight ratio). The crystals were collected by filtration using a Hirsch funnel, and washed twice with 100 g of isopropyl alcohol and vacuum dried at 60° C. to obtain 11.7 g of Compound (V) with a yield of 22.1% and a GPC purity of 97.4%.

Compound (V):

IR (ATR method): ν=3529, 3443, 3038, 2935, 2868, 1608, 1582, 1471, 1448, 1415, 1385, 1295, 1248, 1166, 1115, 1099, 1031, 1010, 995, 946, 919, 827, 770, 750, 734 $cm^{-1}$.

$^1$H-NMR (600 MHz in DMSO-$d_6$): δ=1.39 (4H, m), 1.64 (4H, m), 3.86 (4H, t), 6.18 (2H, —OH), 6.76 (4H, d-t), 7.11 (4H, d-t), 7.21 to 7.25 (8H, m), 7.34 (4H, m), 7.77 (4H, d) ppm.

$^{13}$C-NMR (150 MHz in DMSO-$d_6$): δ=25.23, 28.59, 67.19, 82.22, 113.82, 119.99, 124.57, 126.24, 127.93, 128.32, 136.80, 139.01, 151.48, 157.48 ppm.

[Synthetic Example 9] Synthesis of Compound (A4)

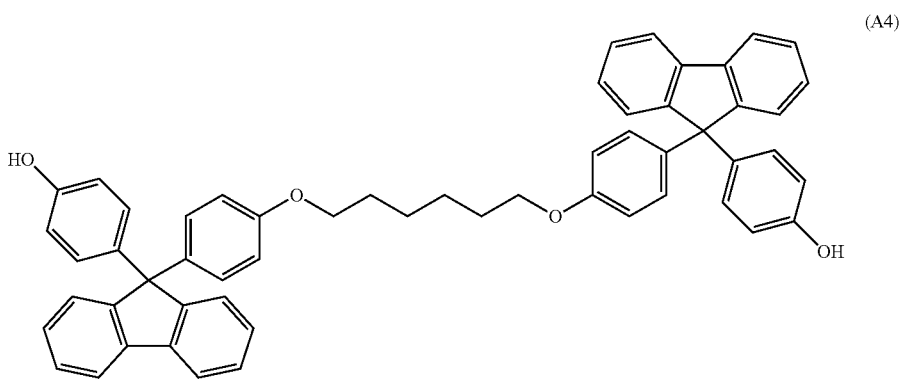 [SMILES: Oc1ccc(C2(c3ccc(OCCCCCCOc4ccc(C5(c6ccc(O)cc6)c6ccccc6-c6ccccc65)cc4)cc3)c3ccccc3-c3ccccc32)cc1]

Under nitrogen atmosphere, in 200 ml of three necked flask equipped with a thermometer and a reflux condenser were weighed 5.0 g (7.9 mmol) of Compound (V) and 6.0 g (63.8 mmol) of phenol, 50 ml of methylene chloride was added to the mixture to prepare a uniform solution in an oil bath at 30° C. To the mixture was gradually added dropwise 2.5 ml of methanesulfonic acid from a dropping funnel, and the mixture was heated for 40 minutes. After cooling the mixture to room temperature by allowing to stand, the mixture was diluted with 150 ml of methyl isobutyl ketone, transferred to a separating funnel, and separation of the liquids and washing with water were repeated until the aqueous layer became neutral. The organic layer was recovered, and after removing the solvent by distillation until the inner composition in an evaporator became 22 g, 88 g of hexane was added dropwise under stirring to precipitate a rice cake-like lump. The supernatant was removed by decantation, 12 g of ethyl acetate and 88 g of methanol were added to the lump to carry out recrystallization. The crystals were collected by filtration using a Hirsch funnel, washed twice with 50 g of methanol and vacuum dried at 60° C. to obtain 2.9 g of Compound (A4) with a yield of 46.7% and a GPC purity of 93.8%.

Compound (A4):
IR (ATR method): ν=3540, 3414, 3062, 2940, 2866, 1609, 1506, 1474, 1447, 1394, 1330, 1292, 1266, 1238, 1181, 1171, 1118, 1105, 1017, 917, 823, 803, 746, 731 cm$^{-1}$.

$^1$H-NMR (600 MHz in DMSO-d$_6$): δ=1.38 (4H, m), 1.64 (4H, m), 3.85 (4H, t), 6.61 (4H, d-t), 6.75 (4H, d-t), 6.89 (4H, d-t), 6.96 (4H, d-t), 7.27 (4H, t-d), 7.32 to 7.36 (8H, m), 7.87 (4H, m), 9.30 (2H, —OH) ppm.

$^{13}$C-NMR (150 MHz in DMSO-d$_6$): δ=25.22, 28.58, 63.56, 67.19, 114.03, 114.93, 120.35, 125.86, 127.32, 127.65, 128.61, 128.64, 135.69, 137.61, 139.30, 151.45, 156.02, 157.27 ppm.

TG-DTA (−5% weight loss temperature, in Air): 350° C.
TG-DTA (−5% weight loss temperature, in He): 356° C.
DSC (Glass transition temperature): 109° C.

[Synthetic Example 10] Synthesis of Compound (A5)

Under nitrogen atmosphere, in 200 ml of three necked flask equipped with a thermometer and a reflux condenser were weighed 5.0 g (7.9 mmol) of Compound (V) and 9.1 g (63.1 mmol) of 2-naphthol, and 100 ml of methylene chloride was added to the mixture to prepare a uniform solution in an oil bath at 30° C. To the mixture was gradually added dropwise 2.5 ml of methanesulfonic acid from a dropping funnel, and the mixture was heated for 2 hours. After cooling the mixture to room temperature by allowing to stand, the mixture was diluted with 220 ml of methyl isobutyl ketone, transferred to a separating funnel, and separation of the liquids and washing with water were repeated until the aqueous layer became neutral. The organic layer was recovered, and after removing the solvent by distillation until the inner composition in an evaporator became 17 g, 25 g of ethyl acetate and 113 g of isopropyl alcohol were added to the residue to carry out recrystallization. The crystals were collected by filtration using a Hirsch funnel, washed twice with 50 g of isopropyl alcohol and vacuum dried at 60° C. to obtain 4.0 g of Compound (A5) with a yield of 57.1% and a GPC purity of 95.0%.

Compound (A5):
IR (ATR method): ν=3545, 3361, 3062, 2941, 2874, 1634, 1605, 1580, 1505, 1475, 1447, 1390, 1348, 1278, 1250, 1223, 1204, 1180, 1147, 1122, 1021, 959, 923, 898, 884, 862, 839, 823, 807, 751, 737 cm$^{-1}$.

$^1$H-NMR (600 MHz in DMSO-d$_6$): δ=1.40 (4H, m), 1.65 (4H, m), 3.87 (4H, t), 6.79 (4H, d), 6.97 (4H, d-d), 7.00 to 7.04 (6H, m), 7.18 (2H, d-d), 7.29 (4H, t), 7.34 to 7.39 (6H, m), 7.44 (4H, d), 7.51 (2H, d), 7.56 (2H, d), 7.91 (4H, d), 9.67 (2H, —OH) ppm.

$^{13}$C-NMR (150 MHz in DMSO-d$_6$): δ=25.22, 28.58, 64.14, 67.20, 108.30, 114.15, 118.70, 120.48, 125.05, 125.98, 126.21, 126.87, 127.12, 127.52, 127.76, 128.73, 129.30, 133.29, 137.19, 139.45, 139.68, 151.01, 155.30, 157.39 ppm.

TG-DTA (−5% weight loss temperature, in Air): 388° C.
TG-DTA (−5% weight loss temperature, in He): 398° C.
DSC (Glass transition temperature): 132° C.

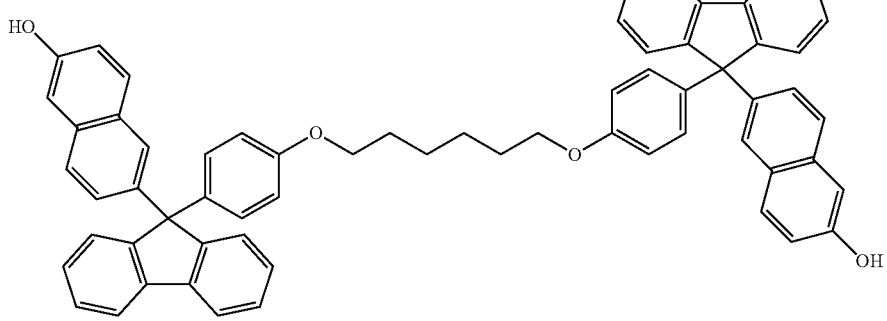

(A5)

[Synthetic Example 11] Synthesis of Compound (A6)

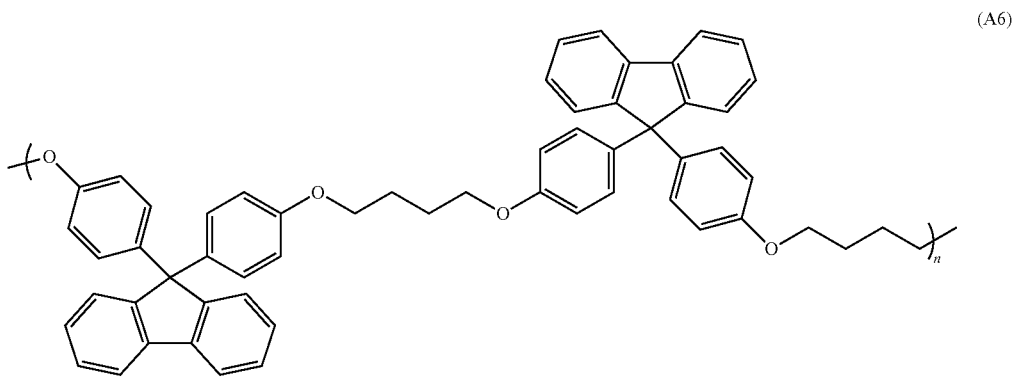

(A6)

Under nitrogen atmosphere, in 200 ml of three necked flask equipped with a thermometer and a reflux condenser were weighed 10.0 g (13.2 mmol) of Compound (A2), 0.30 g (1.3 mmol) of benzyltriethylammonium chloride, 4.7 g of 25% aqueous sodium hydroxide solution and 50 ml of tetrahydrofuran, and the mixture was heated in an oil bath at 60° C. To the mixture was added dropwise 0.95 g (4.4 mmol) of 1,4-dibromobutane previously diluted with 5 g of tetrahydrofuran from a dropping funnel over 5 minutes, and the mixture was heated under reflux for 21 hours. After diluting the mixture with 40 ml of methyl isobutyl ketone, 20% hydrochloric acid was added to the mixture in an ice-bath until the solution became acidic. The mixture was transferred to a separating funnel, and separation of the liquids and washing with water were repeated until the aqueous layer became neutral. The organic layer was recovered and the solvent was removed by evaporation. To the polymer evaporated to dryness was added tetrahydrofuran, and 37 g of a polymer solution thus prepared was added dropwise to 164 g of isopropyl alcohol to precipitate a polymer. The precipitated polymer was collected by filtration, further washed twice with 60 g of isopropyl alcohol and vacuum dried at 60° C. to obtain 5.9 g of Compound (A6) with a yield of 57.6%.

Compound (A6):
GPC (RI): Mw=2070, Mn=1390, Mw/Mn=1.49 n= to 1.8 (calculated from Mn), to 2.0 (calculated from $^1$H-NMR).
IR (ATR method): ν=3546, 3035, 2944, 1607, 1506, 1472, 1447, 1390, 1292, 1243, 1176, 1115, 1013, 915, 823, 745, 729 cm$^{-1}$.
TG-DTA (−5% weight loss temperature, in Air): 361° C.
TG-DTA (−5% weight loss temperature, in He): 366° C.
DSC (Glass transition temperature): 136° C.

[Synthetic Example 12] Synthesis of Compound (A7)

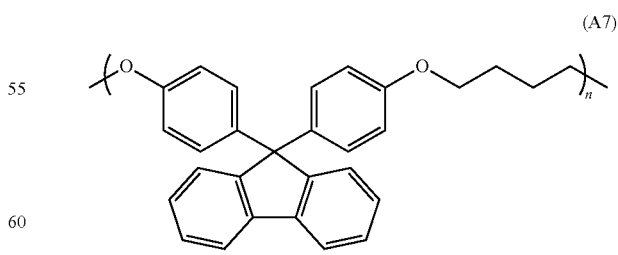

(A7)

Under nitrogen atmosphere, in 200 ml of three necked flask equipped with a thermometer and a reflux condenser were weighed 20.0 g (57.1 mmol) of 9,9-bis(4-hydroxyphenyl)-fluorene, 0.65 g (2.9 mmol) of benzyltriethylammonium chloride, 20.1 g of 25% aqueous sodium hydroxide solution and 50 ml of tetrahydrofuran, and the mixture was heated in an oil bath at 60° C. To the mixture was added dropwise 4.11 g (19.0 mmol) of 1,4-dibromobutane previously diluted with 5 g of tetrahydrofuran from a dropping funnel over 10 minutes, and the mixture was heated under reflux for 28 hours. To the mixture were added 50 ml of methyl isobutyl ketone and 100 ml of tetrahydrofuran, 20% hydrochloric acid was added to the mixture in an ice-bath until the solution became acidic. The mixture was transferred to a separating funnel, and separation of the liquids and washing with water were repeated until the aqueous layer became neutral. The organic layer was recovered and the solvent was removed by distillation. To the polymer evaporated to dryness was added tetrahydrofuran, 70 g of a polymer solution thus prepared was added dropwise to 420 g of methanol to precipitate a polymer. The precipitated polymer was collected by filtration, further washed twice with 100 g of methanol and vacuum dried at 60° C. to obtain 4.9 g of Compound (A7) with a yield of 23.3%.
Compound (A7):
GPC (RI): Mw=2510, Mn=1490, Mw/Mn=1.68 n= to 3.8 (calculated from Mn), to 4.0 (calculated from $^1$H-NMR).
IR (ATR method): v=3526, 3034, 2948, 1606, 1505, 1427, 1446, 1388, 1290, 1242, 1175, 1113, 1013, 915, 822, 744, 729 cm$^{-1}$.
TG-DTA (−5% weight loss temperature, in Air): 363° C.
TG-DTA (−5% weight loss temperature, in He): 368° C.
DSC (Glass transition temperature): 139° C.

[Synthetic Example 13] Synthesis of Compound (A8)

ered and the solvent was removed by distillation using an evaporator. The residue was recovered and vacuum dried at 60° C. to obtain 8.8 g of Compound (A8) with a yield of 87.0%.
Compound (A8):
GPC (RI): Mw=3880, Mn=1570, Mw/Mn=2.47

[Synthetic Example 14] Synthesis of Compound (A9)

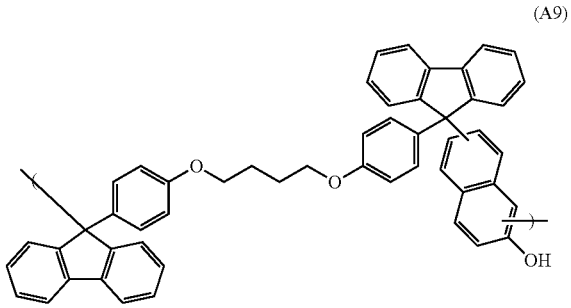

(A9)

Under nitrogen atmosphere, in 100 ml of three necked flask equipped with a thermometer and a reflux condenser were weighed 4.71 g (7.8 mmol) of Compound (III) and 1.69 g (11.7 mmol) of 2-naphthol, and 25 ml of 1,2-dichloroethane was added to the mixture to prepare a uniform solution in an oil bath at 60° C. To the mixture was gradually added dropwise 0.5 ml of methanesulfonic acid from a dropping funnel, and the reaction was carried out in an oil bath at 60° C. for 8 hours. The mixture was cooled at room temperature by allowing to stand, diluted with 100 ml of methyl isobutyl ketone, transferred to a separating funnel, and separation of the liquids and washing with water were repeated until the aqueous layer became neutral. The organic layer was recovered, and after removing the solvent by distillation until the inner composition in an evaporator became 20.6 g, the reside was added dropwise to 122 g of methanol:water=4:1 (weight ratio) to precipitate a polymer. The precipitated polymer was collected by filtration using a Hirsch funnel, washed twice with 36 g of methanol:water=4:1 (weight ratio) and vacuum dried at 60° C. to obtain 5.8 g of Compound (A9) with a yield of 94.7%.
Compound (A9):
GPC (RI): Mw=2320, Mn=1350, Mw/Mn=1.72

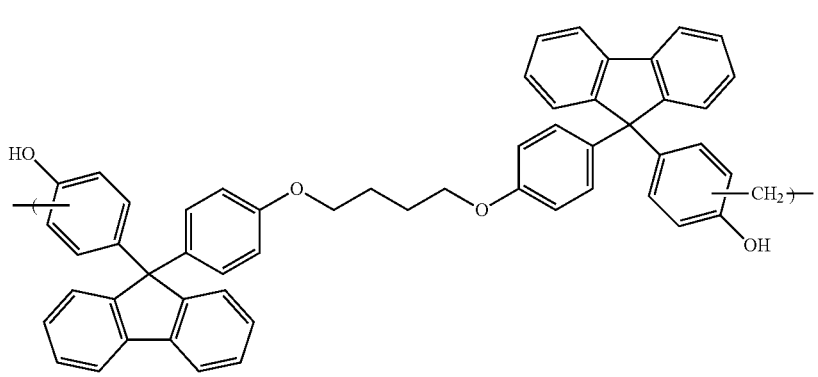

(A8)

Under nitrogen atmosphere, in 200 ml of three necked flask equipped with a thermometer and a reflux condenser were weighed 10.0 g (13.3 mmol) of Compound (A2) and 0.75 g (corresponding to 9.3 mmol of formalin) of 37% aqueous formalin solution, 40 ml of propylene glycol monomethyl ether was added to the mixture to prepare a uniform solution in an oil bath at 90° C. To the mixture was gradually added dropwise 2.5 g of a propylene glycol monomethyl ether solution containing 20 wt % of p-toluenesulfonic acid monohydrate previously prepared from a dropping funnel. After completion of the dropwise addition, the reaction was carried out in an oil bath at 120° C. for 19 hours. The mixture was cooled at room temperature by allowing to stand, diluted with 200 ml of methyl isobutyl ketone, transferred to a separating funnel and separation of liquids and washing with water were repeated until the aqueous layer became neutral. The organic layer was recov-

[Synthetic Example 15] Synthesis of Compound (A10)

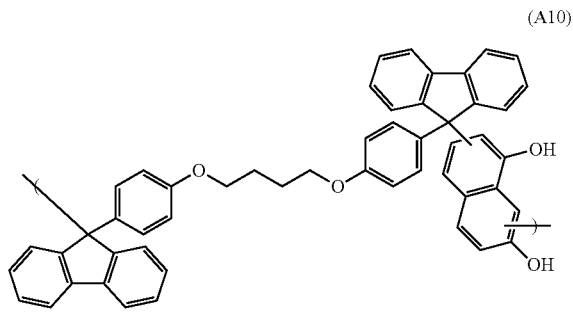

Under nitrogen atmosphere, in 100 ml of three necked flask equipped with a thermometer and a reflux condenser were weighed 7.28 g (12.1 mmol) of Compound (III) and 2.90 g (18.1 mmol) of 1,7-dihydroxynaphthalene, and 50 ml of 1,2-dichloroethane was added to the mixture to prepare a suspended solution in an oil bath at 50° C. To the suspension was gradually added dropwise 0.24 ml of methanesulfonic acid from a dropping funnel, and the reaction was carried out in an oil bath at 60° C. for 1.5 hours. The mixture was cooled at room temperature by allowing to stand, diluted with 100 ml of methyl isobutyl ketone, transferred to a separating funnel, and separation of the liquids and washing with water were carried out until the aqueous layer became neutral. The organic layer was recovered and the solvent was removed by distillation. To the residue was added tetrahydrofuran, and 40 g of the polymer solution thus prepared was added dropwise to 150 g of methanol:water=4:1 (weight ratio) to precipitate a polymer. The precipitated polymer was collected by filtration using a Hirsch funnel, washed twice with 50 g of methanol:water=4:1 (weight ratio) and vacuum dried at 60° C. to obtain 8.2 g of Compound (A10) with a yield of 84.2%.
Compound (A10):
  GPC (RI): Mw=3410, Mn=1880, Mw/Mn=1.81

[Synthetic Example 16] Synthesis of Compound (A11)

Under nitrogen atmosphere, in 100 ml of three necked flask equipped with a thermometer and a reflux condenser were weighed 8.9 g (14.8 mmol) of Compound (III) and 8.9 g (19.8 mmol) of 6,6-(9-fluorenylidene)-di(2-naphthol), and 60 ml of γ-butyrolactone was added to the mixture to prepare a uniform solution in an oil bath at 60° C. To the mixture was gradually added dropwise 4.8 ml of methanesulfonic acid from a dropping funnel, and the reaction was carried out in an oil bath at 60° C. for 1.5 hours. The mixture was cooled at room temperature by allowing to stand, diluted with 120 ml of methyl isobutyl ketone, transferred to a separating funnel, and separation of the liquids and washing with water were repeated until the aqueous layer became neutral. The organic layer was recovered and the solvent was removed by distillation. To the residue was added tetrahydrofuran, and 63 g of a polymer solution thus prepared was added dropwise to 150 g of methanol to precipitate a polymer. The precipitated polymer was collected by filtration using a Hirsch funnel, washed twice with 80 g of methanol and vacuum dried at 60° C. to obtain 9.9 g of Compound (A11) with a yield of 57.2%.
Compound (A10):
  GPC (RI): Mw=4040, Mn=2580, Mw/Mn=1.57

[Synthetic Example 17] Synthesis of Compound (VI)

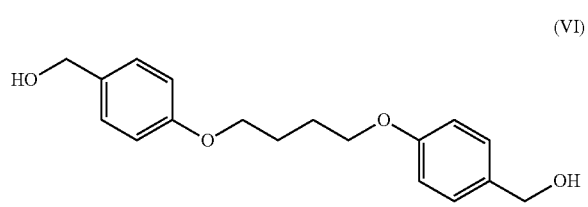 [SMILES: OCc1ccc(OCCCCOc2ccc(CO)cc2)cc1]

Under nitrogen atmosphere, in 300 ml of three necked flask equipped with a thermometer and a reflux condenser were weighed 25.0 g (201.4 mmol) of 4-hydroxybenzyl alcohol, 18.5 g (85.6 mmol) of 1,4-dibromobutane and 30.6 g (221.5 mmol) of potassium carbonate, 50 g of dimethylformamide was added to the mixture and the reaction was carried out in an oil bath at 40° C. for 24 hours. The mixture was cooled at room temperature by allowing to stand, diluted with 130 ml of water, 300 ml of tetrahydrofuran and 60 ml of toluene, and transferred to a separating funnel. The aqueous layer was removed and washed with 60 g of 5 wt % aqueous sodium hydroxide solution, and separation of the liquids and washing with water were repeated until the aqueous layer became neutral. The solvent was removed by

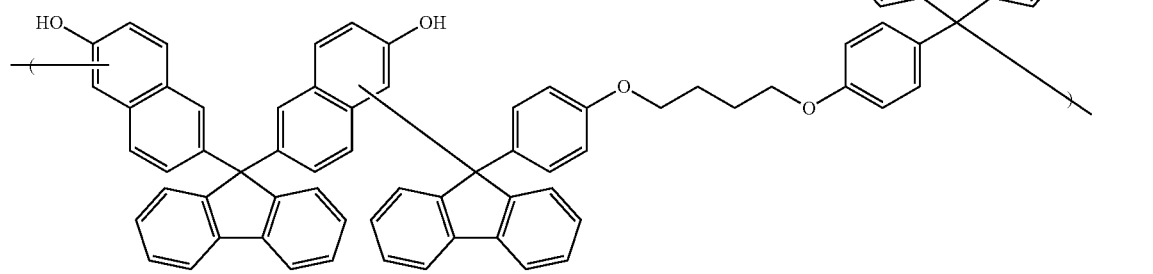

distillation until the inner composition in an evaporator became 130 g, and 156 g of diisopropyl ether was added dropwise to the residue under stirring to precipitate crystals. The crystals were collected by filtration using a Hirsch funnel, washed twice with 50 g of diisopropyl ether and vacuum dried at 50° C. to obtain 19.4 g of Compound (VI) with a yield of 74.9% and a GPC purity of 94.9%.

Compound (VI):

IR (ATR method): ν=3332, 2955, 2929, 2908, 2870, 1612, 1586, 1512, 1474, 1448, 1386, 1303, 1249, 1212, 1198, 1174, 1167, 1110, 1052, 1039, 1009, 997, 977, 929, 827, 808, 790 cm$^{-1}$.

$^1$H-NMR (600 MHz in DMSO-d$_6$): δ=1.84 (4H, m), 3.99 (4H, t), 4.39 (4H, d), 5.02 (—OH, t), 6.87 (4H, d-t), 7.20 (4H, d-t) ppm.

$^{13}$C-NMR (150 MHz in DMSO-d$_6$): δ=26.00, 63.12, 67.63, 114.57, 128.45, 135.01, 158.04 ppm.

[Synthetic Example 18] Synthesis of Compound (A12)

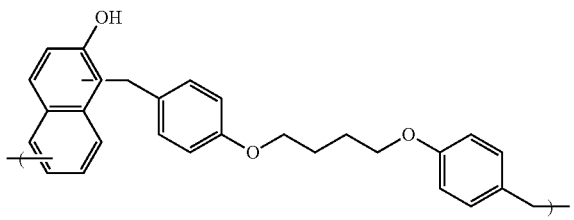

(A12)

Under nitrogen atmosphere, in 100 ml of three necked flask equipped with a thermometer and a reflux condenser were weighed 3.15 g (10.4 mmol) of Compound (VI) and 2.0 g (13.9 mmol) of 2-naphthol, and 20 ml of γ-butyrolactone was added to the mixture to prepare a uniform solution in an oil bath at 80° C. To the mixture was gradually added dropwise 1.0 g of a γ-butyrolactone solution containing 20 wt % of p-toluenesulfonic acid monohydrate previously prepared from a dropping funnel. After completion of the dropwise addition, the reaction was carried out in an oil bath at 80° C. for 3 hours. The mixture was cooled at room temperature by allowing to stand, diluted with 100 ml of methyl isobutyl ketone, transferred to a separating funnel, and separation of liquids and washing with water were repeated until the aqueous layer became neutral. The organic layer was recovered, and the solvent was removed by distillation by an evaporator. The residue was recovered and vacuum dried at 60° C. to obtain 4.6 g of Compound (A12) with a yield of 96.4%.

Compound (A12):
GPC (RI): Mw=1720, Mn=880, Mw/Mn=1.95

[Synthetic Example 19] Synthesis of Compound (A13)

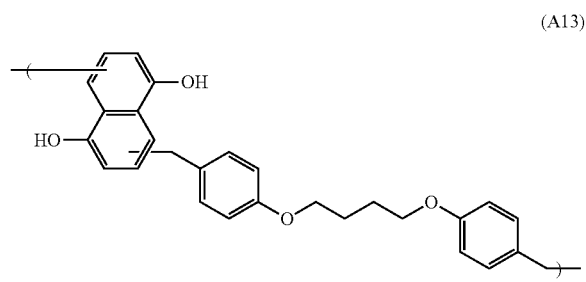

(A13)

Under nitrogen atmosphere, in 100 ml of three necked flask equipped with a thermometer and a reflux condenser were weighed 4.25 g (14.0 mmol) of Compound (VI) and 3.0 g (18.7 mmol) of 1,5-dihydroxynaphthalene, and 30 ml of γ-butyrolactone was added to the mixture to prepare a uniform solution in an oil bath at 80° C. To the mixture was gradually added dropwise 1.0 g of a γ-butyrolactone solution containing 20 wt % of p-toluenesulfonic acid monohydrate previously prepared from a dropping funnel. After completion of the dropwise addition, the reaction was carried out in an oil bath at 80° C. for 3 hours. After cooling the mixture to room temperature by allowing to stand, the mixture was diluted with 100 ml of methyl isobutyl ketone, transferred to a separating funnel, and separation of liquids and washing with water were repeated until the aqueous layer became neutral. The organic layer was recovered, and the solvent was removed by distillation by an evaporator. The residue was recovered and vacuum dried at 60° C. to obtain 5.9 g of Compound (A13) with a yield of 87.5%.

Compound (A13):
GPC (RI): Mw=6960, Mn=1250, Mw/Mn=5.57

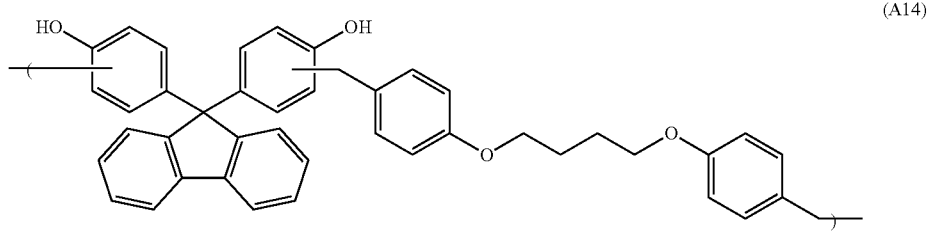

(A14)

[Synthetic Example 20] Synthesis of Compound (A14)

Under nitrogen atmosphere, in 200 ml of three necked flask equipped with a thermometer and a reflux condenser were weighed 5.61 g (18.6 mmol) of Compound (VI) and 10.0 g (28.5 mmol) of 9,9-bis(4-hydroxyphenyl)fluorene, and 40 ml of propylene glycol monomethyl ether was added to the mixture to prepare a uniform solution in an oil bath at 90° C. To the mixture was gradually added dropwise 2.5 g of a propylene glycol monomethyl ether solution containing 20 wt % of p-toluenesulfonic acid monohydrate previously prepared from a dropping funnel. After completion of the dropwise addition, the reaction was carried out in an oil bath at 120° C. for 5 hours. After cooling the mixture to room temperature by allowing to stand, the mixture was diluted with 200 ml of methyl isobutyl ketone, transferred to a separating funnel, and separation of liquids and washing with water were repeated until the aqueous layer became neutral. The organic layer was recovered, and the solvent was removed by distillation by an evaporator. The residue was recovered and vacuum dried at 60° C. to obtain 13.5 g of Compound (A14) with a yield of 90.4%.

Compound (A14):
  GPC (RI): Mw=20530, Mn=1160, Mw/Mn=17.70

[Synthetic Example 21] Synthesis of Compound (A15)

Under nitrogen atmosphere, in 200 ml of three necked flask equipped with a thermometer and a reflux condenser were weighed 2.80 g (9.27 mmol) of Compound (VI) and 10.0 g (13.3 mmol) of Compound (A2), and 40 ml of γ-butyrolactone was added to the mixture to prepare a uniform solution in an oil bath at 90° C. To the mixture was gradually added dropwise 2.5 g of a γ-butyrolactone solution containing 20 wt % of p-toluenesulfonic acid monohydrate previously prepared from a dropping funnel. After completion of the dropwise addition, the reaction was carried out in an oil bath at 120° C. for 3 hours. After cooling the mixture to room temperature by allowing to stand, the mixture was diluted with 200 ml of methyl isobutyl ketone, transferred to a separating funnel, and separation of liquids and washing with water were repeated until the aqueous layer became neutral. The organic layer was recovered, and the solvent was removed by distillation by an evaporator. The residue was recovered and vacuum dried at 60° C. to obtain 11.4 g of Compound (A15) with a yield of 91.4%.

Compound (A15):
  GPC (RI): Mw=18110, Mn=1840, Mw/Mn=9.84

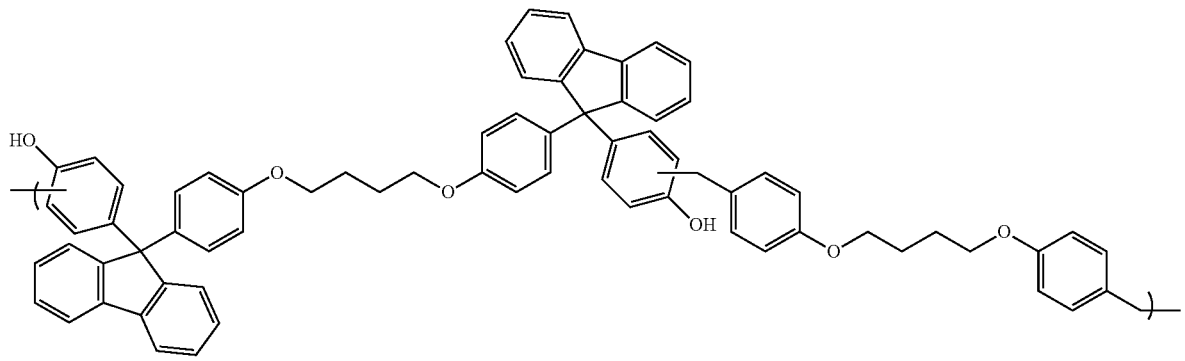

(A15)

[Synthetic Example 22] Synthesis of Compound (A16)

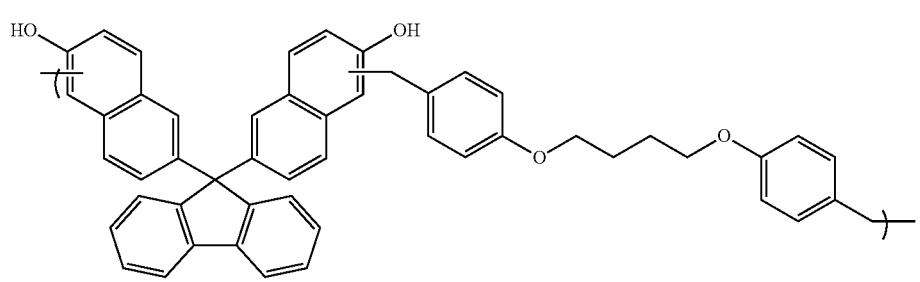

(A16)

Under nitrogen atmosphere, in 200 ml of three necked flask equipped with a thermometer and a reflux condenser were weighed 4.36 g (14.4 mmol) of Compound (VI) and- 10.0 g (22.2 mmol) of 6,6-(9-fluorenylidene)-di(2-naphthol), and 40 ml of propylene glycol monomethyl ether was added to the mixture to prepare a uniform solution in an oil bath at 90° C. To the mixture was gradually added dropwise 2.5 g of a propylene glycol monomethyl ether solution containing 20 wt % of p-toluenesulfonic acid monohydrate previously prepared from a dropping funnel. After completion of the dropwise addition, the reaction was carried out in an oil bath at 120° C. for 5 hours. After cooling the mixture to room temperature by allowing to stand, the mixture was diluted with 200 ml of methyl isobutyl ketone, transferred to a separating funnel, and separation of liquids and washing with water were repeated until the aqueous layer became neutral. The organic layer was recovered, and the solvent was removed by distillation by an evaporator. The residue was recovered and vacuum dried at 60° C. to obtain 12.4 g of Compound (A16) with a yield of 89.6%.

Compound (A16):
GPC (RI): Mw=3580, Mn=1350, Mw/Mn=2.64

[Synthetic Example 23] Synthesis of Compound (VII)

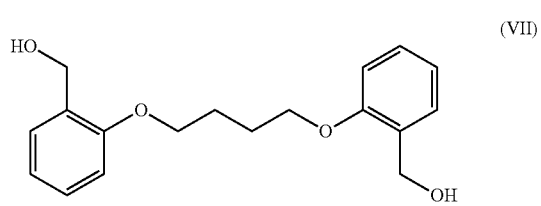 [SMILES: OCc1ccccc1OCCCCOc1ccccc1CO]

(VII)

Reaction and purification were carried out in the same manner as in Synthetic example 17 except for using 25.0 g of 2-hydroxybenzyl alcohol in place of 25.0 g of 4-hydroxybenzyl alcohol. As a result, 23.5 g of the objective compound, Compound (VII) was obtained with a yield of 80.6% and a GPC purity of 79.0%.

Compound (VII):
IR (ATR method): ν=3206, 2959, 2914, 2873, 1601, 1590, 1493, 1472, 1455, 1396, 1375, 1305, 1282, 1156, 1111, 1060, 1039, 1016, 945, 926, 850, 838, 749 cm$^{-1}$.

$^1$H-NMR (600 MHz in DMSO-$d_6$): δ=1.88 (4H, m), 4.02 (4H, t), 4.52 (4H, d), 4.95 (—OH, t), 6.90 to 6.95 (4H, m), 7.18 (2H, t-d), 7.38 (2H, d) ppm.

$^{13}$C-NMR (150 MHz in DMSO-$d_6$): δ=25.75, 57.98, 67.29, 111.11, 120.18, 127.02, 127.66, 130.68, 155.44 ppm.

[Synthetic Example 24] Synthesis of Compound (A17)

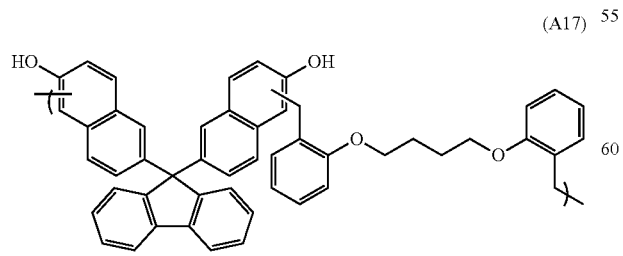

(A17)

Under nitrogen atmosphere, in 200 ml of three necked flask equipped with a thermometer and a reflux condenser were weighed 4.36 g (14.4 mmol) of Compound (VII) and 10.0 g (22.2 mmol) of 6,6-(9-fluorenylidene)-di(2-naphthol), and 40 ml of γ-butyrolactone was added to the mixture to prepare a uniform solution in an oil bath at 90° C. To the mixture was gradually added dropwise 2.5 g of a γ-butyrolactone solution containing 20 wt % of p-toluenesulfonic acid monohydrate previously prepared from a dropping funnel. After completion of the dropwise addition, the reaction was carried out in an oil bath at 120° C. for 3 hours. After cooling the mixture to room temperature by allowing to stand, the mixture was diluted with 200 ml of methyl isobutyl ketone, transferred to a separating funnel, and separation of liquids and washing with water were repeated until the aqueous layer became neutral. The organic layer was recovered and the solvent was removed by distillation. To the reside was added tetrahydrofuran, and 40 g of a polymer solution thus prepared was added dropwise to 200 g of methanol to precipitate a polymer. The precipitated polymer was collected by filtration using a Hirsch funnel, washed twice with 80 g of methanol and vacuum dried at 60° C. to obtain 6.7 g of Compound (A17) with a yield of 48.4%.

Compound (A17):
GPC (RI): Mw=3800, Mn=2190, Mw/Mn=1.74

[Synthetic Example 25] Synthesis of Compound (VIII)

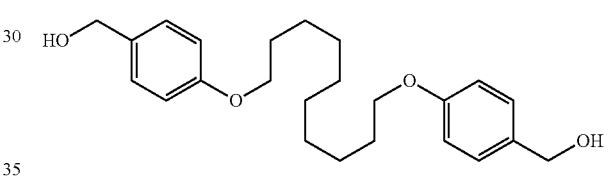

(VIII)

Reaction and purification were carried out in the same manner as in Synthetic example 17 except for using 25.68 g of 1,10-dibromodecane in place of 18.5 g of 1,4-dibromobutane. As a result, 23.3 g of the objective compound, Compound (VIII) was obtained with a yield of 70.4% and a GPC purity of 94.5%.

Compound (VIII):
IR (ATR method): ν=3327, 2936, 2921, 2852, 1611, 1582, 1512, 1475, 1464, 1395, 1300, 1171, 1113, 1049, 1016, 836, 820, 800 cm$^{-1}$.

$^1$H-NMR (600 MHz in DMSO-$d_6$): δ=1.24 to 1.36 (8H, m), 1.38 (4H, quint), 1.67 (4H, quint), 3.90 (4H, t), 4.39 (4H, d), 5.01 (—OH, t), 6.84 (4H, d-t), 7.18 (4H, d) ppm.

[Synthetic Example 26] Synthesis of Compound (A18)

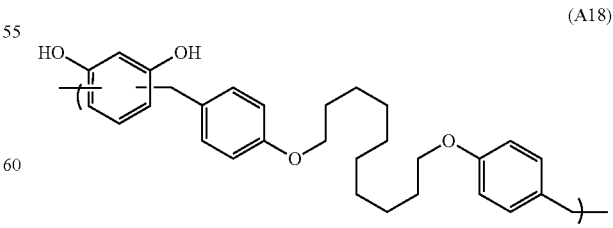

(A18)

Under nitrogen atmosphere, in 100 ml of three necked flask equipped with a thermometer and a reflux condenser were weighed 5.27 g (13.6 mmol) of Compound (VIII) and 2.0 g (18.2 mmol) of resorcinol, and 30 ml of propylene glycol monomethyl ether was added to the mixture to prepare a uniform solution in an oil bath at 90° C. To the mixture was gradually added dropwise 1.0 g of a propylene glycol monomethyl ether solution containing 20 wt % of p-toluenesulfonic acid monohydrate previously prepared from a dropping funnel. After completion of the dropwise addition, the reaction was carried out in an oil bath at 120° C. for 4 hours. After cooling the mixture to room temperature by allowing to stand, the mixture was diluted with 200 ml of methyl isobutyl ketone, transferred to a separating funnel, and separation of liquids and washing with water were repeated until the aqueous layer became neutral. The organic layer was recovered, the solvent was removed by distillation by an evaporator, and the residue was recovered and vacuum dried at 60° C. to obtain 5.8 g of Compound (A18) with a yield of 85.6%.

Compound (A18):
  GPC (RI): Mw=6020, Mn=1230, Mw/Mn=4.89

[Synthetic Example 27] Synthesis of Compound (A19)

solution containing 20 wt % of p-toluenesulfonic acid monohydrate previously prepared from a dropping funnel. After completion of the dropwise addition, the reaction was carried out in an oil bath at 150° C. for 8 hours. After cooling the mixture to room temperature by allowing to stand, and the mixture was diluted with 200 ml of methyl isobutyl ketone, transferred to a separating funnel, and separation of liquids and washing with water were repeated until the aqueous layer became neutral. The organic layer was recovered, and the solvent was removed by distillation by an evaporator. The residue was recovered and vacuum dried at 60° C. to obtain 17.5 g of Compound (A19) with a yield of 95.4%.

Compound (A19):
  GPC (RI): Mw=13250, Mn=2410, Mw/Mn=5.50

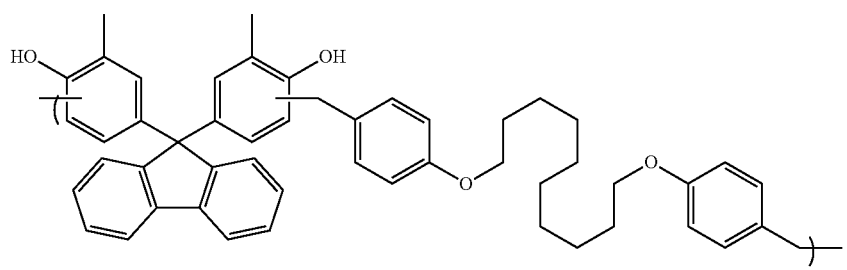

(A19)

Under nitrogen atmosphere, in 200 ml of three necked flask equipped with a thermometer and a reflux condenser were weighed 9.19 g (23.8 mmol) of Compound (VIII) and 10.0 g (26.4 mmol) of 9,9-bis(4-hydroxy-3-methylphenyl)fluorine, and 50 ml of propylene glycol monopropyl ether was added to the mixture in an oil bath at 90° C. to prepare a uniform solution. To the mixture was gradually added dropwise 2.5 g of a propylene glycol monopropyl ether

[Synthetic Example 28] Synthesis of Compound (A20)

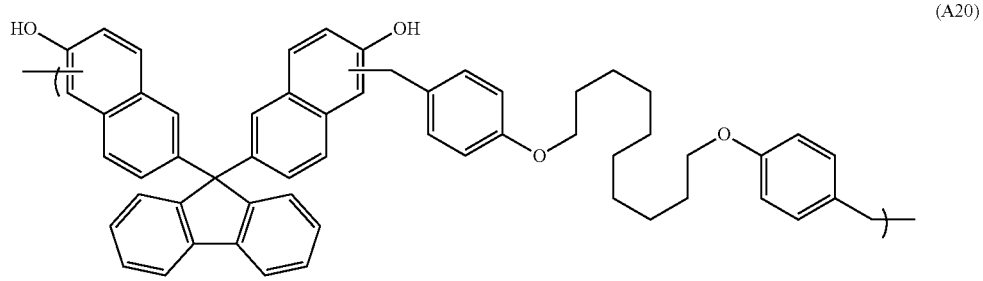

(A20)

Under nitrogen atmosphere, in 200 ml of three necked flask equipped with a thermometer and a reflux condenser were weighed 6.86 g (17.8 mmol) of Compound (VIII) and 10.0 g (22.2 mmol) of 6,6-(9-fluorenylidene)-di(2-naphthol), and 50 ml of propylene glycol monomethyl ether was added to the mixture to prepare a uniform solution in an oil bath at 90° C. To the mixture was gradually added dropwise 2.5 g of a propylene glycol monomethyl ether solution containing 20 wt % of p-toluenesulfonic acid monohydrate previously prepared from a dropping funnel. After completion of the dropwise addition, the reaction was carried out in an oil bath at 120° C. for 4 hours. After cooling the mixture to room temperature by allowing to stand, the mixture was diluted with 200 ml of methyl isobutyl ketone, transferred to a separating funnel, and separation of liquids and washing with water were repeated until the aqueous layer became neutral. The organic layer was recovered, and the solvent was removed by distillation by an evaporator. The residue was recovered and vacuum dried at 60° C. to obtain 14.9 g of Compound (A20) with a yield of 91.8%.

Compound (A20):
GPC (RI): Mw=8760, Mn=2460, Mw/Mn=3.56
(Comparison Polymer) Liquid State Additive (B1)

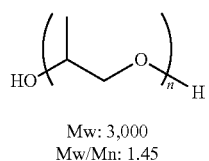

(B1)

Mw: 3,000
Mw/Mn: 1.45

Preparation of Resist Underlayer Film Compositions (UDL-1 to 23, Comparative UDL-1 to 5)

The Compounds (A1) to (A20), a liquid state additive (B1), base resins containing an aromatic ring represented by (R1) to (R3), cross-linking agents represented by CR1 and CR2, an acid generator represented by AG1 and a solvent were dissolved in a medium containing 0.1% by mass of FC-4430 (product of Sumitomo 3M Limited) with ratios shown in Table 1, and filtered through a 0.1 μm filter made of a fluorine resin to prepare resist underlayer film compositions (ULD-1 to 23, Comparative UDL-1 to 5), respectively.

TABLE 1

| Composition | Compound (parts by mass) | Base resin (parts by mass) | Cross-linking agent (parts by mass) | Acid generator (parts by mass) | Solvent (parts by mass) |
|---|---|---|---|---|---|
| UDL-1 | A2 (10) | None | CR1 (2) | AG1 (1) | PGMEA (90) |
| UDL-2 | A6 (10) | None | | | PGMEA (63)/cyclohexanone (27) |
| UDL-3 | A7 (10) | None | | | PGMEA (63)/cyclohexanone (27) |
| UDL-4 | A1 (5) | R1 (5) | | | PGMEA (63)/cyclohexanone (27) |
| UDL-5 | A2 (5) | R1 (5) | | | PGMEA (63)/cyclohexanone (27) |
| UDL-6 | A3 (5) | R1 (5) | | | PGMEA (63)/cyclohexanone (27) |
| UDL-7 | A4 (5) | R1 (5) | | | PGMEA (63)/cyclohexanone (27) |
| UDL-8 | A5 (5) | R1 (5) | | | PGMEA (63)/cyclohexanone (27) |
| UDL-9 | A2 (5) | R2 (5) | | | PGMEA (90) |
| UDL-10 | A2 (5) | R3 (5) | CR2 (2) | AG1 (1) | PGMEA (90) |
| UDL-11 | A8 (10) | None | | | PGMEA (90) |
| UDL-12 | A9 (10) | None | | | PGMEA (90) |
| UDL-13 | A10 (10) | None | | | PGMEA (90) |
| UDL-14 | A11 (10) | None | | | PGMEA (90) |
| UDL-15 | A12 (10) | None | | | PGMEA (90) |
| UDL-16 | A13 (10) | None | | | PGMEA (90) |
| UDL-17 | A14 (10) | None | | | PGMEA (90) |
| UDL-18 | A15 (10) | None | | | PGMEA (90) |
| UDL-19 | A16 (10) | None | | | PGMEA (90) |
| UDL-20 | A17 (10) | None | | | PGMEA (90) |
| UDL-21 | A18 (10) | None | | | PGMEA (90) |
| UDL-22 | A19 (10) | None | | | PGMEA (90) |
| UDL-23 | A20 (10) | None | | | PGMEA (90) |
| Comparative UDL-1 | None | R1 (10) | | | PGMEA (63)/cyclohexanone (27) |
| Comparative UDL-2 | None | R2 (10) | | | PGMEA (90) |
| Comparative UDL-3 | None | R3 (10) | CR2 (2) | AG1 (1) | PGMEA (90) |
| Comparative UDL-4 | B1 (5) | R1 (5) | | | PGMEA (63)/cyclohexanone (27) |
| Comparative UDL-5 | B1 (2) | R1 (10) | | | PGMEA (63)/cyclohexanone (27) |

PGMEA: Propylene glycol monomethyl ether acetate (R1) to (R3) used as the base resins containing an aromatic ring, CR1 and CR2 used as the cross-linking agents, and AG1 used as an acid generator are shown below.

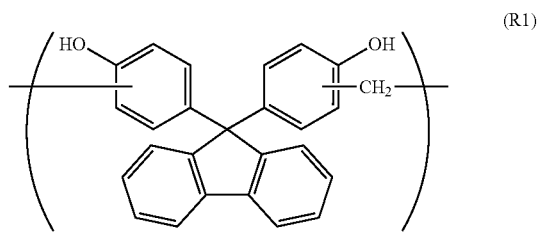

(R1)

Mw: 22,000
Mw/Mn: 4.20

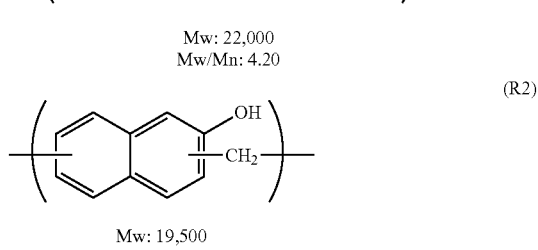

(R2)

Mw: 19,500
Mw/Mn: 3.80

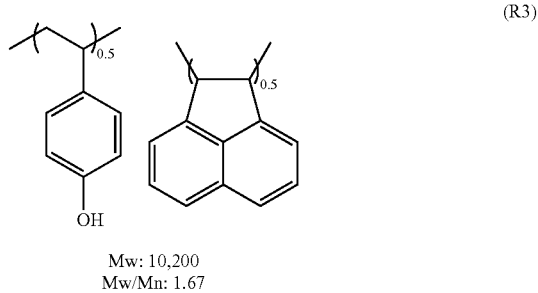

(R3)

Mw: 10,200
Mw/Mn: 1.67

-continued

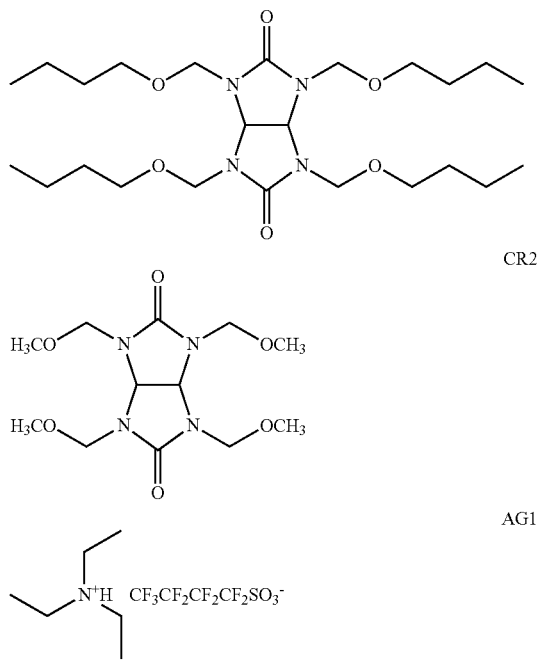

Measurement of Solvent Resistance (Examples 1-1 to 1-23, Comparative Examples 1-1 to 1-5)

The prepared resist underlayer film compositions (UDL-1 to 23, Comparative UDL-1 to 5) were coated on a silicon substrate, baked under the conditions shown in Table 2, and then, the film thickness was measured, respectively. The film thickness was measured, and a PGMEA solvent was dispensed thereon, allowed to stand for 30 seconds and spin dried, and baked at 100° C. for 60 seconds to evaporate the PGMEA. Then, the film thickness was measured again to obtain a difference in the film thickness before and after the PGMEA treatment.

TABLE 2

| | Composition | Film thickness after film formation: a (Å) | Film thickness after PGMEA treatment: b (Å) | b/a × 100 (%) | Baking temperature (° C.) |
|---|---|---|---|---|---|
| Example 1-1 | UDL-1 | 2845 | 2843 | 100 | 350° C. × 60 sec |
| Example 1-2 | UDL-2 | 2830 | 2829 | 100 | 350° C. × 60 sec |
| Example 1-3 | UDL-3 | 2821 | 2820 | 100 | 350° C. × 60 sec |
| Example 1-4 | UDL-4 | 2876 | 2875 | 100 | 350° C. × 60 sec |
| Example 1-5 | UDL-5 | 2769 | 2769 | 100 | 350° C. × 60 sec |
| Example 1-6 | UDL-6 | 2812 | 2810 | 100 | 350° C. × 60 sec |
| Example 1-7 | UDL-7 | 2809 | 2809 | 100 | 350° C. × 60 sec |
| Example 1-8 | UDL-8 | 2853 | 2852 | 100 | 350° C. × 60 sec |
| Example 1-9 | UDL-9 | 2795 | 2794 | 100 | 350° C. × 60 sec |
| Example 1-10 | UDL-10 | 2820 | 2818 | 100 | 250° C. × 60 sec |
| Example 1-11 | UDL-11 | 2968 | 2967 | 100 | 350° C. × 60 sec |
| Example 1-12 | UDL-12 | 2860 | 2858 | 100 | 350° C. × 60 sec |
| Example 1-13 | UDL-13 | 2912 | 2911 | 100 | 350° C. × 60 sec |
| Example 1-14 | UDL-14 | 2926 | 2925 | 100 | 350° C. × 60 sec |
| Example 1-15 | UDL-15 | 2893 | 2892 | 100 | 350° C. × 60 sec |
| Example 1-16 | UDL-16 | 2956 | 2955 | 100 | 350° C. × 60 sec |
| Example 1-17 | UDL-17 | 2914 | 2913 | 100 | 350° C. × 60 sec |
| Example 1-18 | UDL-18 | 2918 | 2916 | 100 | 350° C. × 60 sec |
| Example 1-19 | UDL-19 | 2956 | 2955 | 100 | 350° C. × 60 sec |
| Example 1-20 | UDL-20 | 2934 | 2933 | 100 | 350° C. × 60 sec |
| Example 1-21 | UDL-21 | 2949 | 2948 | 100 | 350° C. × 60 sec |
| Example 1-22 | UDL-22 | 2975 | 2973 | 100 | 350° C. × 60 sec |
| Example 1-23 | UDL-23 | 2919 | 2919 | 100 | 350° C. × 60 sec |
| Comparative Example 1-1 | Comparative UDL-1 | 2928 | 2927 | 100 | 350° C. × 60 sec |
| Comparative Example 1-2 | Comparative UDL-2 | 2956 | 2955 | 100 | 350° C. × 60 sec |
| Comparative Example 1-3 | Comparative UDL-3 | 2928 | 2928 | 100 | 250° C. × 60 sec |
| Comparative Example 1-4 | Comparative UDL-4 | Poor film-formation | | | 350° C. × 60 sec |
| Comparative Example 1-5 | Comparative UDL-5 | 2928 | 2925 | 100 | 350° C. × 60 sec |

As shown in Table 2, in either of the resist underlayer films using any of the organic film compositions (UDL-1 to 23), it could be understood that they were all good film-forming property (mirror surface state), and, there were substantially no decrease in the film thickness by the solvent treatment whereby films with solvent resistance could be obtained. On the other hand, in Comparative UDL-4 in which the liquid state additive (B1) had been formulated with a significant amount, film-formation was poor (like a frosted glass), so that it was necessary to reduce the loading amount thereof.

Etching Test in $CF_4/CHF_3$-Based Gas (Examples 2-1 to 2-23, Comparative Examples 2-1 to 2-4)

The resist underlayer films were formed in the same manner as mentioned above, and an etching test with a $CF_4/CHF_3$-based gas was carried out under the following conditions.

Etching Conditions

| Chamber pressure | 40.0 Pa |
|---|---|
| RF power | 1,300 W |
| $CHF_3$ gas flow rate | 30 ml/min |
| $CF_4$ gas flow rate | 30 ml/min |
| Ar gas flow rate | 100 ml/min |
| Time | 60 sec |

By using an etching apparatus TE-8500 product of Tokyo Electron Limited, the remained films before and after etching were measured. The results are shown in Table 3.

TABLE 3

| | Composition | Film thickness before etching: a (Å) | Film thickness after etching: b (Å) | b/a × 100 (%) |
|---|---|---|---|---|
| Example 2-1 | UDL-1 | 2987 | 1851 | 62 |
| Example 2-2 | UDL-2 | 2857 | 1776 | 62.2 |

TABLE 3-continued

| | Composition | Film thickness before etching: a (Å) | Film thickness after etching: b (Å) | b/a × 100 (%) |
|---|---|---|---|---|
| Example 2-3 | UDL-3 | 2867 | 1788 | 62.4 |
| Example 2-4 | UDL-4 | 2834 | 1842 | 65 |
| Example 2-5 | UDL-5 | 2872 | 1809 | 63 |
| Example 2-6 | UDL-6 | 2854 | 1866 | 65.4 |
| Example 2-7 | UDL-7 | 2776 | 1730 | 62.3 |
| Example 2-8 | UDL-8 | 2810 | 1821 | 64.8 |
| Example 2-9 | UDL-9 | 2892 | 1798 | 62.2 |
| Example 2-10 | UDL-10 | 2948 | 1859 | 63.1 |
| Example 2-11 | UDL-11 | 2837 | 1756 | 61.9 |
| Example 2-12 | UDL-12 | 2898 | 1910 | 65.9 |
| Example 2-13 | UDL-13 | 2930 | 1890 | 64.5 |
| Example 2-14 | UDL-14 | 2747 | 1802 | 65.6 |
| Example 2-15 | UDL-15 | 2857 | 1768 | 61.9 |
| Example 2-16 | UDL-16 | 2874 | 1768 | 61.5 |
| Example 2-17 | UDL-17 | 2857 | 1780 | 62.3 |
| Example 2-18 | UDL-18 | 2911 | 1808 | 62.1 |
| Example 2-19 | UDL-19 | 2820 | 1856 | 65.8 |
| Example 2-20 | UDL-20 | 2859 | 1873 | 65.5 |
| Example 2-21 | UDL-21 | 2798 | 1710 | 61.1 |
| Example 2-22 | UDL-22 | 2852 | 1771 | 62.1 |
| Example 2-23 | UDL-23 | 2884 | 1883 | 65.3 |
| Comparative Example 2-1 | Comparative UDL-1 | 2781 | 1785 | 64.2 |
| Comparative Example 2-2 | Comparative UDL-2 | 2956 | 1853 | 62.7 |
| Comparative Example 2-3 | Comparative UDL-3 | 2762 | 1815 | 65.7 |
| Comparative Example 2-4 | Comparative UDL-5 | 2928 | 1723 | 58.8 |

As shown in Table 3, it could be confirmed that the resist underlayer film compositions (UDL-1 to 23) using the organic film compositions had the same or superior etching resistance to those of the comparative underlayer compositions (Comparative UDL-1 to 3, 5). Among the resist underlayer film compositions, UDL-4 to 8 correspond to Comparative UDL-1, UDL-9 to Comparative UDL-2, and UDL-10 to Comparative UDL-3, respectively.

On the other hand, as stated hereinbelow, whereas the liquid state additive (B1) is effective for improvement of filling property and planarizing characteristics, in Comparative UDL-5, a film remaining rate by etching became small as compared with that of UDL-1 to which no (B1) had been formulated, so that it could be understood that it deteriorates etching resistance.

Evaluation of Filling Property (Examples 3-1 to 3-23, Comparative Examples 3-1 to 3-4)

Figure 2G:
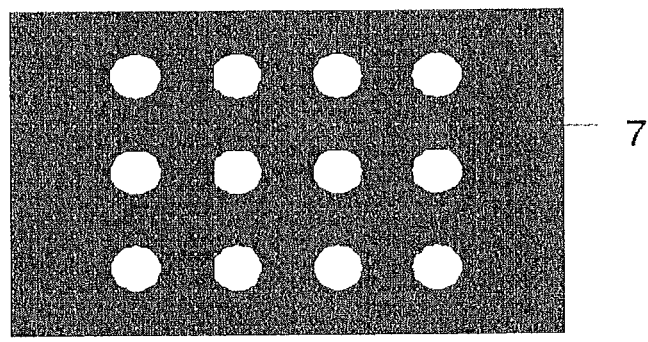
FIGS. 2G-2I are explanatory views of an evaluation method of filling property.
Figure 2H:
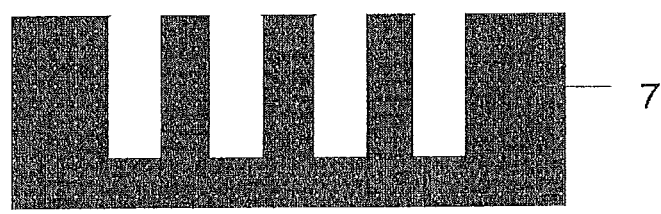
Figure 2I:
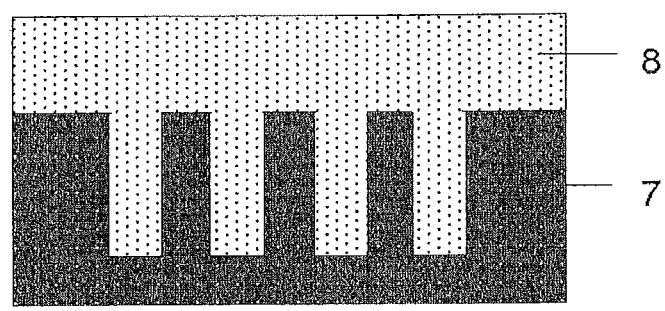

As shown in FIGS. 2G-2I, the resist underlayer film compositions were each coated on a SiO₂ wafer substrate having a dense hole pattern (hole diameter: 0.16 μm, hole depth: 0.50 μm, distance between the centers of the adjacent two holes: 0.32 μm), and heated by using a hot plate at 180° C. for 60 seconds, to form a resist underlayer film 8. The substrate used is a basis substrate 7 (SiO₂ wafer substrate) having a dense hole pattern as shown in FIG. 2G (downward view) and FIG. 2H (sectional view). Cross-sectional shapes of the obtained respective wafer substrates were observed by using a scanning electron microscope (SEM), and whether inside of the hole was filled by the resist underlayer film without voids or not was confirmed. The results are shown in Table 4. When a resist underlayer film composition inferior in filling property is used, voids occur at the inside of the hole in this evaluation. When the resist underlayer film compositions having good filling property are employed, in this evaluation, the resist underlayer film is filled without any voids at the inside of the hole as shown in FIG. 2I.

TABLE 4

| | Composition | Presence or absence of voids |
|---|---|---|
| Example 3-1 | UDL-1 | None |
| Example 3-2 | UDL-2 | None |
| Example 3-3 | UDL-3 | None |
| Example 3-4 | UDL-4 | None |
| Example 3-5 | UDL-5 | None |
| Example 3-6 | UDL-6 | None |
| Example 3-7 | UDL-7 | None |
| Example 3-8 | UDL-8 | None |
| Example 3-9 | UDL-9 | None |
| Example 3-10 | UDL-10 | None |
| Example 3-11 | UDL-11 | None |
| Example 3-12 | UDL-12 | None |
| Example 3-13 | UDL-13 | None |
| Example 3-14 | UDL-14 | None |
| Example 3-15 | UDL-15 | None |
| Example 3-16 | UDL-16 | None |
| Example 3-17 | UDL-17 | None |
| Example 3-18 | UDL-18 | None |
| Example 3-19 | UDL-19 | None |
| Example 3-20 | UDL-20 | None |
| Example 3-21 | UDL-21 | None |
| Example 3-22 | UDL-22 | None |
| Example 3-23 | UDL-23 | None |
| Comparative Example 3-1 | Comparative UDL-1 | Present |
| Comparative Example 3-2 | Comparative UDL-2 | Present |
| Comparative Example 3-3 | Comparative UDL-3 | Present |
| Comparative Example 3-4 | Comparative UDL-5 | None |

As shown in Table 4, it can be confirmed that the resist underlayer film compositions (UDL-1 to 23) can fill the hole pattern without any voids, and have excellent filling property as compared with those of the comparative underlayer compositions (Comparative UDL-1 to 3). In Comparative UDL-5, voids appeared in Comparative UDL-1 were eliminated, and it can be understood that the liquid state additive (B1) is effective for the improvement of the filling property. However, as stated above, addition of (B1) is accompanied by deterioration of etching resistance so that it is not preferred as an underlayer composition.

Evaluation of Planarizing Characteristics (Examples 4-1 to 4-23, Comparative Examples 4-1 to 4-4)

Figure 3J:
FIGS. 3J-3K are explanatory views of an evaluation method of planarizing characteristics.
Figure 3K:
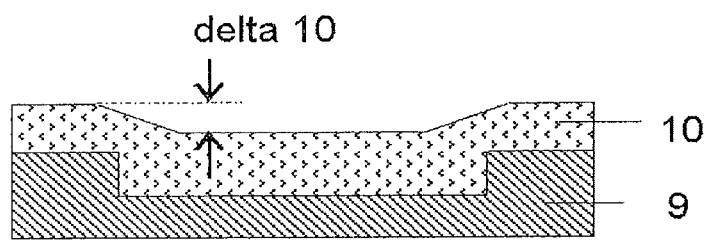

The resist underlayer film compositions were each coated on a basis substrate 9 (SiO₂ wafer substrate) having a giant isolated trench pattern (FIG. 3J, trench width: 10 μm, trench depth: 0.50 μm), and after baking these compositions under the conditions shown in Table 5, a difference in film thicknesses at the trench portion and the non-trench portion of the resist underlayer film 10 (delta 10 in FIG. 3K) was observed by using a scanning electron microscope (SEM). The results are shown in Table 5. In this evaluation, as the difference between the film thicknesses is small, planarizing characteristics can be said to be good. Incidentally, in this evaluation, the trench pattern having a depth of 0.50 μm is planarized by using a resist underlayer film composition having a usual film thickness of about 0.3 μm, so that this is a specific severe evaluation condition to evaluate superiority or inferiority of the planarizing.

TABLE 5

| | Composition | Baking temperature | Difference in film thicknesses (nm) |
|---|---|---|---|
| Example 4-1 | UDL-1 | 180° C. × 60 sec + 350° C. × 60 sec | 140 |
| Example 4-2 | UDL-2 | 180° C. × 60 sec + 350° C. × 60 sec | 140 |
| Example 4-3 | UDL-3 | 180° C. × 60 sec + 350° C. × 60 sec | 140 |
| Example 4-4 | UDL-4 | 180° C. × 60 sec + 350° C. × 60 sec | 160 |
| Example 4-5 | UDL-5 | 180° C. × 60 sec + 350° C. × 60 sec | 160 |
| Example 4-6 | UDL-6 | 180° C. × 60 sec + 350° C. × 60 sec | 170 |
| Example 4-7 | UDL-7 | 180° C. × 60 sec + 350° C. × 60 sec | 150 |
| Example 4-8 | UDL-8 | 180° C. × 60 sec + 350° C. × 60 sec | 160 |
| Example 4-9 | UDL-9 | 180° C. × 60 sec + 350° C. × 60 sec | 160 |
| Example 4-10 | UDL-10 | 180° C. × 60 sec + 250° C. × 60 sec | 150 |
| Example 4-11 | UDL-11 | 180° C. × 60 sec + 350° C. × 60 sec | 170 |
| Example 4-12 | UDL-12 | 180° C. × 60 sec + 350° C. × 60 sec | 150 |
| Example 4-13 | UDL-13 | 180° C. × 60 sec + 350° C. × 60 sec | 150 |
| Example 4-14 | UDL-14 | 180° C. × 60 sec + 350° C. × 60 sec | 160 |
| Example 4-15 | UDL-15 | 180° C. × 60 sec + 300° C. × 60 sec | 140 |
| Example 4-16 | UDL-16 | 180° C. × 60 sec + 350° C. × 60 sec | 160 |
| Example 4-17 | UDL-17 | 180° C. × 60 sec + 350° C. × 60 sec | 150 |
| Example 4-18 | UDL-18 | 180° C. × 60 sec + 350° C. × 60 sec | 140 |
| Example 4-19 | UDL-19 | 180° C. × 60 sec + 350° C. × 60 sec | 150 |
| Example 4-20 | UDL-20 | 180° C. × 60 sec + 350° C. × 60 sec | 150 |
| Example 4-21 | UDL-21 | 180° C. × 60 sec + 300° C. × 60 sec | 130 |
| Example 4-22 | UDL-22 | 180° C. × 60 sec + 350° C. × 60 sec | 140 |
| Example 4-23 | UDL-23 | 180° C. × 60 sec + 350° C. × 60 sec | 140 |
| Comparative Example 4-1 | Comparative UDL-1 | 180° C. × 60 sec + 350° C. × 60 sec | 290 |
| Comparative Example 4-2 | Comparative UDL-2 | 180° C. × 60 sec + 350° C. × 60 sec | 320 |
| Comparative Example 4-3 | Comparative UDL-3 | 180° C. × 60 sec + 250° C. × 60 sec | 280 |
| Comparative Example 4-4 | Comparative UDL-5 | 180° C. × 60 sec + 350° C. × 60 sec | 230 |

As shown in Table 5, the resist underlayer film compositions (UDL-1 to 23) were all small in the difference between film thicknesses of the resist underlayer film at the trench portion and the non-trench portion, as compared with those of the comparative underlayer compositions (Comparative UDL-1 to 3, 5), whereby it could be confirmed that they were excellent in planarizing characteristics.

Pattern Formation Test (Examples 5-1 to 5-23)

The respective resist underlayer film compositions (UDL-1 to 23) were each coated on a $SiO_2$ wafer substrate having a trench pattern (trench width: 10 μm, trench depth: 0.10 μm), and baked by the conditions described in Table 8 to prepare resist underlayer films. The resist middle layer film composition SOG1 was each coated thereon and baked at 200° C. for 60 seconds to form a resist middle layer film having a film thickness of 35 nm, and an SL resist for ArF of a resist upper layer film composition was coated thereon and baked at 105° C. for 60 seconds to form a photoresist film having a film thickness of 100 nm. The liquid immersion protective film composition (TC-1) was coated on the photoresist film, and baked at 90° C. for 60 seconds to form a protective film having a film thickness of 50 nm.

As the resist middle layer film composition (SOG-1), 2% propylene glycol ethyl ether solution of the following polymer was prepared.

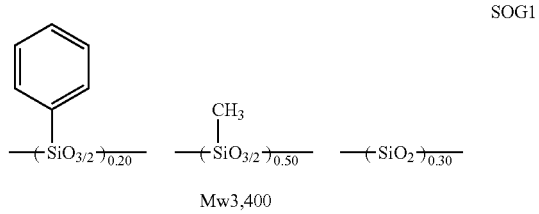

SOG1

Mw3,400

In a solvent containing 0.1% by mass of FC-430 (product of Sumitomo 3M Limited) were dissolved a resin shown by RP1, an acid generator PAG1 and a base compound Amine 1 as resist upper layer film compositions (single layer resist for ArF) with a ratio shown in Table 6, and the mixture was filtered through a 0.1 μm filter made of a fluorine resin to prepare a composition.

TABLE 6

| No. | Polymer (parts by mass) | Acid generator (part by mass) | Base compound (parts by mass) | Solvent (parts by mass) |
|---|---|---|---|---|
| Single layer resist for ArF | RP1 (100) | PAG1 (6.6) | Amine 1 (0.8) | PGMEA (2,500) |

The used RP1, PAG1 and Amine 1 are shown below.

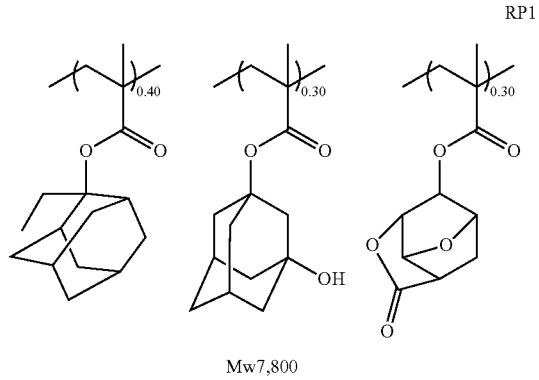

RP1

Mw7,800

-continued

PAG1

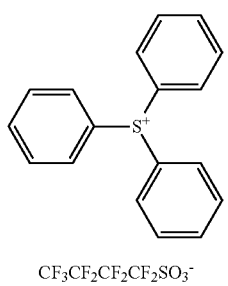

CF₃CF₂CF₂CF₂SO₃⁻

Amine1

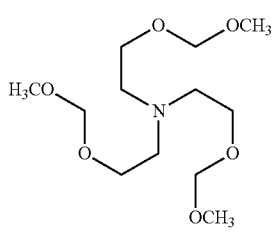

As a liquid immersion protective film composition (TC-1), the polymer PP1 was dissolved in an organic solvent with a ratio shown in Table 7, and the solution was filtered by a 0.1 μm filter made of a fluorine resin to prepare the composition.

TABLE 7

| No. | Polymer (parts by mass) | Solvent (parts by mass) |
|---|---|---|
| TC-1 | PP1 (100) | Diisoamyl ether (2,700) 2-methyl-1-butanol (270) |

The used polymer PP1 is shown below.

PP1

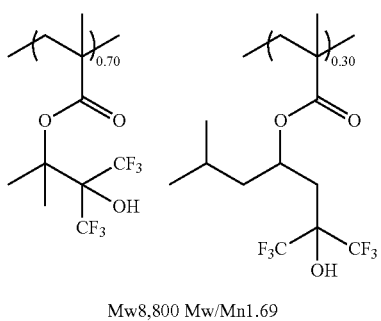

Mw8,800 Mw/Mn1.69

Then, the composition was exposed by using ArF liquid immersion exposure apparatus (NSR-S610C product of Nikon Corporation, NA1.30, σ 0.98/0.65, 35° dipole s polarizing illumination, 6% half-tone phase shift mask), baked at 100° C. for 60 seconds (PEB), and developed by 2.38% by mass aqueous tetramethylammonium hydroxide (TMAH) solution for 30 seconds, to obtain 55 nm 1:1 positive-type line-and-space pattern.

Subsequently, the resist middle layer film was subjected to etching processing by using the resist pattern as a mask due to dry etching using an etching apparatus Telius product of Tokyo Electron Limited, the resist underlayer film was subjected to etching by using the obtained pattern-formed resist middle layer film as a mask, and the SiO₂ film was subjected to etching processing by using the obtained pattern-formed resist underlayer film as a mask. The etching conditions are as shown below.

Transcription conditions of the resist pattern to the resist middle layer film.

| Chamber pressure | 10.0 Pa |
|---|---|
| RF power | 1,500 W |
| CF₄ gas flow rate | 75 sccm |
| O₂ gas flow rate | 15 sccm |
| Time | 15 sec |

Transcription conditions of the pattern-formed resist middle layer film to the resist underlayer film.

| Chamber pressure | 2.0 Pa |
|---|---|
| RF power | 500 W |
| Ar gas flow rate | 75 sccm |
| O₂ gas flow rate | 45 sccm |
| Time | 120 sec |

Transcription conditions of the pattern-formed resist underlayer layer film to the SiO₂ film.

| Chamber pressure | 2.0 Pa |
|---|---|
| RF power | 2,200 W |
| C₅F₁₂ gas flow rate | 20 sccm |
| C₂F₆ gas flow rate | 10 sccm |
| Ar gas flow rate | 300 sccm |
| O₂ | 60 sccm |
| Time | 90 sec |

The pattern cross-section was observed by an electron microscope (S-4700) product of Hitachi, Ltd., and the results are shown in Table 8.

TABLE 8

| | Composition | Baking temperature | Shape after substrate transcription and etching |
|---|---|---|---|
| Example 5-1 | UDL-1 | 180° C. × 60 sec + 350° C. × 60 sec | Perpendicular shape |
| Example 5-2 | UDL-2 | 180° C. × 60 sec + 350° C. × 60 sec | Perpendicular shape |
| Example 5-3 | UDL-3 | 180° C. × 60 sec + 350° C. × 60 sec | Perpendicular shape |
| Example 5-4 | UDL-4 | 180° C. × 60 sec + 350° C. × 60 sec | Perpendicular shape |
| Example 5-5 | UDL-5 | 180° C. × 60 sec + 350° C. × 60 sec | Perpendicular shape |
| Example 5-6 | UDL-6 | 180° C. × 60 sec + 350° C. × 60 sec | Perpendicular shape |
| Example 5-7 | UDL-7 | 180° C. × 60 sec + 350° C. × 60 sec | Perpendicular shape |
| Example 5-8 | UDL-8 | 180° C. × 60 sec + 350° C. × 60 sec | Perpendicular shape |
| Example 5-9 | UDL-9 | 180° C. × 60 sec + 350° C. × 60 sec | Perpendicular shape |
| Example 5-10 | UDL-10 | 180° C. × 60 sec + 250° C. × 60 sec | Perpendicular shape |
| Example 5-11 | UDL-11 | 180° C. × 60 sec + 350° C. × 60 sec | Perpendicular shape |
| Example 5-12 | UDL-12 | 180° C. × 60 sec + 350° C. × 60 sec | Perpendicular shape |
| Example 5-13 | UDL-13 | 180° C. × 60 sec + 350° C. × 60 sec | Perpendicular shape |
| Example 5-14 | UDL-14 | 180° C. × 60 sec + 350° C. × 60 sec | Perpendicular shape |

TABLE 8-continued

| | Composition | Baking temperature | Shape after substrate transcription and etching |
|---|---|---|---|
| Example 5-15 | UDL-15 | 180° C. × 60 sec + 300° C. × 60 sec | Perpendicular shape |
| Example 5-16 | UDL-16 | 180° C. × 60 sec + 350° C. × 60 sec | Perpendicular shape |
| Example 5-17 | UDL-17 | 180° C. × 60 sec + 350° C. × 60 sec | Perpendicular shape |
| Example 5-18 | UDL-18 | 180° C. × 60 sec + 350° C. × 60 sec | Perpendicular shape |
| Example 5-19 | UDL-19 | 180° C. × 60 sec + 350° C. × 60 sec | Perpendicular shape |
| Example 5-20 | UDL-20 | 180° C. × 60 sec + 350° C. × 60 sec | Perpendicular shape |
| Example 5-21 | UDL-21 | 180° C. × 60 sec + 300° C. × 60 sec | Perpendicular shape |
| Example 5-22 | UDL-22 | 180° C. × 60 sec + 350° C. × 60 sec | Perpendicular shape |
| Example 5-23 | UDL-23 | 180° C. × 60 sec + 350° C. × 60 sec | Perpendicular shape |

As a result of this test, in either of the cases, the upper layer resist pattern was finally transferred to the substrate well, and it can be confirmed that the resist underlayer film composition can be suitably used for fine processing by the multilayer resist process, even on a substrate having a step(s).

It must be stated here that the present invention is not restricted to the embodiments shown by the embodiments. The embodiments are merely examples so that any embodiments composed of substantially the same technical concept as disclosed in the claims and expressing a similar effect are included in the technical scope.

What is claimed is:

1. A compound for forming an organic film, the compound comprising a partial structure represented by the following formula (ii),

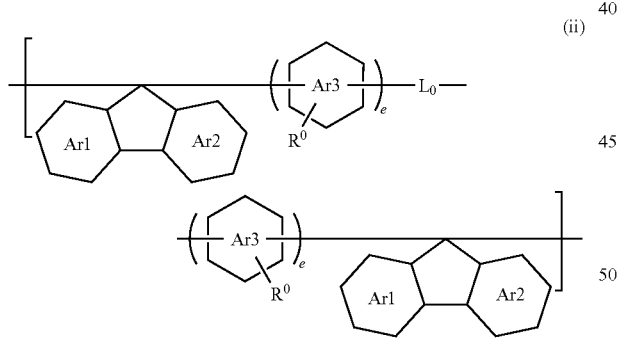

(ii)

wherein the ring structures Ar1, Ar2 and Ar3 each represent a substituted or unsubstituted benzene ring or naphthalene ring; e is 0 or 1; $R^0$ represents a hydrogen atom or a linear, branched or cyclic monovalent organic group having 1 to 30 carbon atoms; $L_0$ represents a divalent organic group selected from the following:

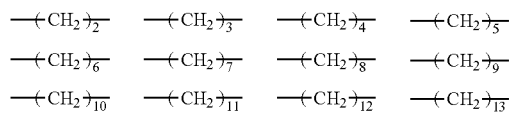

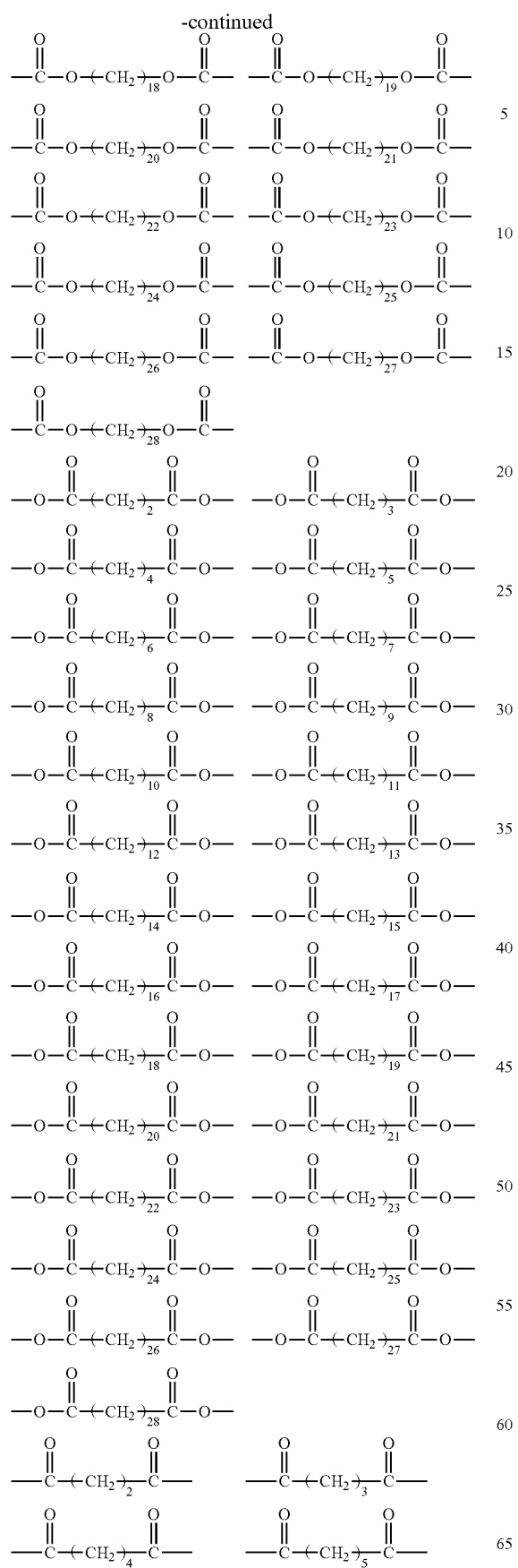
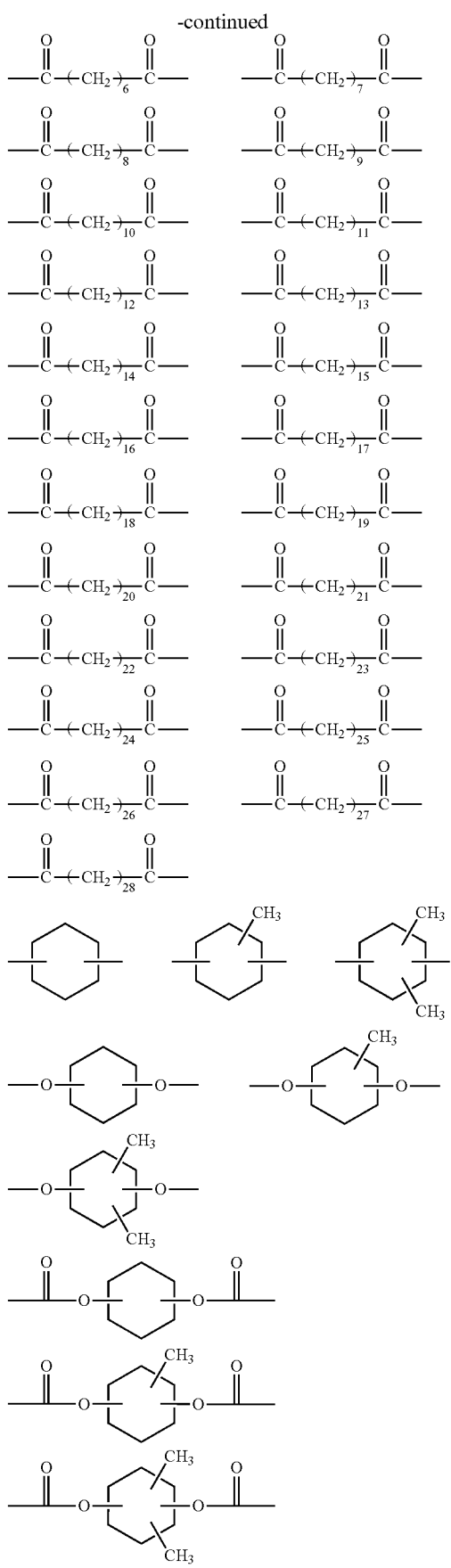

-continued

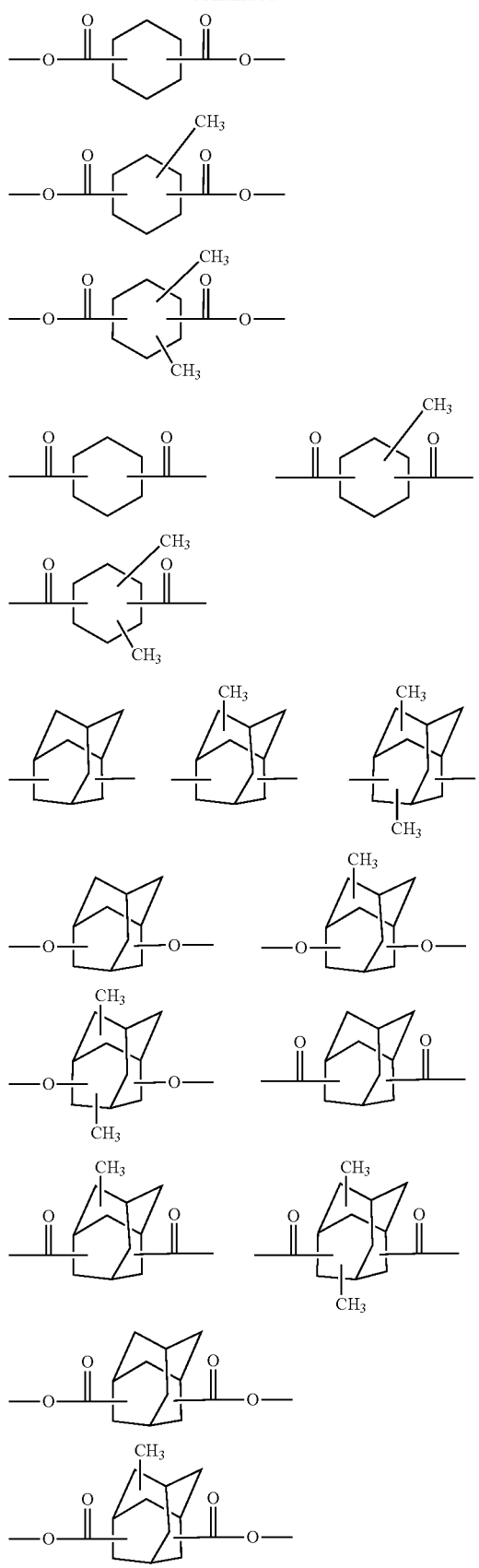

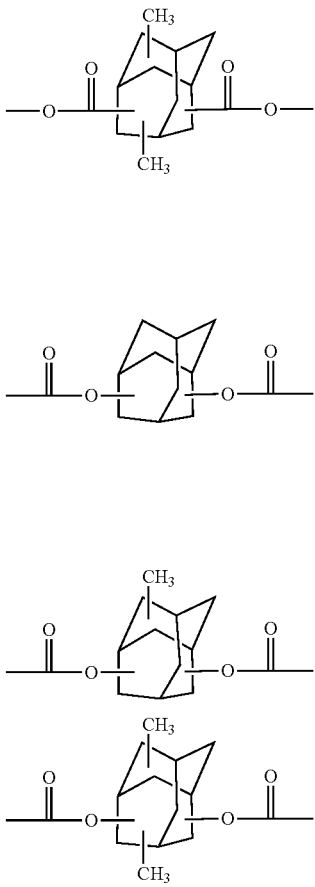

2. The compound for forming an organic film according to claim 1, wherein the compound contains a compound represented by the following formula (iii),

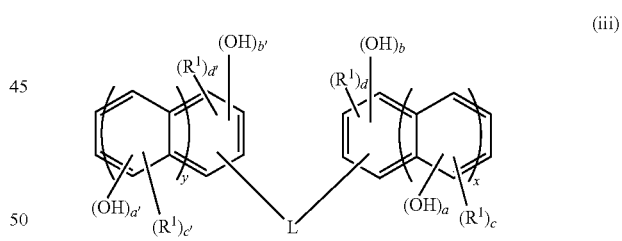

wherein $R^1$ represents a linear, branched or cyclic monovalent hydrocarbon group having 1 to 20 carbon atoms, and a methylene group constituting $R^1$ may be substituted by an oxygen atom; a+b and a'+b' are each independently 1, 2 or 3; c, d, c' and d' are each independently 0, 1 or 2; x and y each independently represent 0 or 1, when x=0, then a=c=0, and when y=0, then a'=c'=0; and L represents a partial structure represented by the formula (ii).

3. The compound for forming an organic film according to claim 2, wherein the compound represented by the formula (iii) is a compound containing an aliphatic hydrocarbon group represented by the following formula (1),

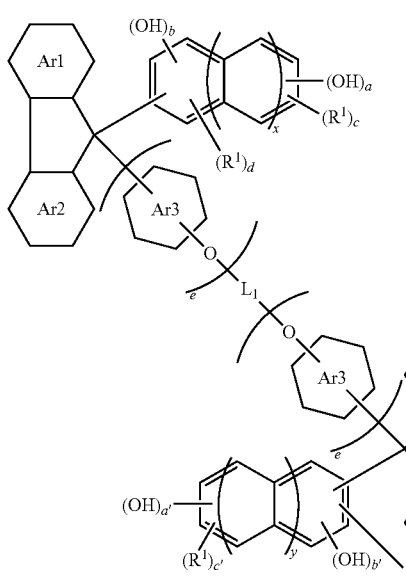

(1)

wherein when e=0, $L_1$ has the same meaning as $L_0$; and when e=1, $L_1$ is a group in which oxygen atoms on both the terminals are removed from $L_0$ that has oxygen atoms on both the terminals.

4. The compound for forming an organic film according to claim 1, wherein the compound contains a partial structure represented by the following formula (iv),

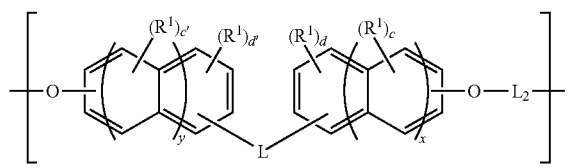

(iv)

wherein $R^1$ represents a linear, branched or cyclic monovalent hydrocarbon group having 1 to 20 carbon atoms, and a methylene group constituting $R^1$ may be substituted by an oxygen atom; c, d, c' and d' are each independently 0, 1 or 2; x and y each independently represent 0 or 1, when x=0, then c=0, and when y=0, then c'=0; L represents a partial structure represented by the formula (ii); $L_2$ represents a linear, branched or cyclic divalent organic group having 2 to 30 carbon atoms; and a methylene group constituting $L_2$ may be substituted by an oxygen atom or a carbonyl group, and the hydrogen atom constituting the structure may be substituted by a hydroxyl group.

5. The compound for forming an organic film according to claim 4, wherein the partial structure represented by the formula (iv) is a partial structure represented by the following formula (2),

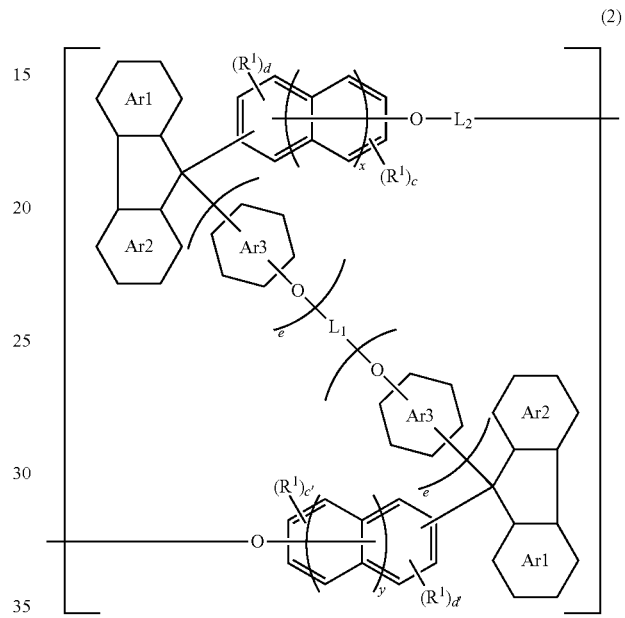

(2)

wherein when e=0, $L_1$ has the same meaning as $L_0$; and when e=1, $L_1$ is a group in which oxygen atoms on both the terminals are removed from $L_0$ that has oxygen atoms on both the terminals.

6. The compound for forming an organic film according to claim 1, wherein the compound contains a polymer compound having a partial structure represented by the following formula (v),

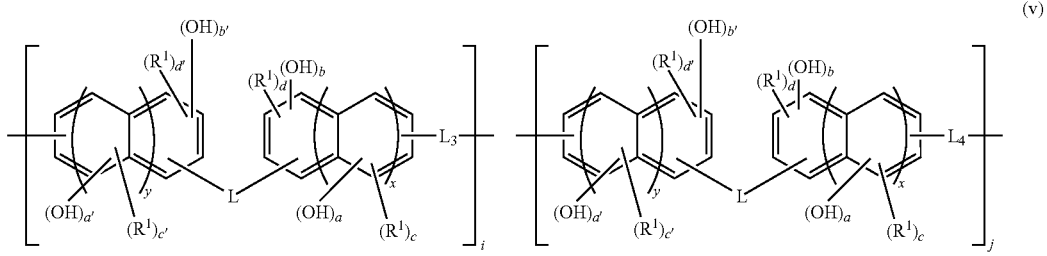

(v)

wherein $R^1$ represents a linear, branched or cyclic monovalent hydrocarbon group having 1 to 20 carbon atoms, and a methylene group constituting $R^1$ may be substituted by an oxygen atom; a+b and a'+b' are each independently 1, 2 or 3; c, d, c' and d' are each independently 0, 1 or 2; x and y each independently represent 0 or 1, when x=0, then a=c=0, and when y=0, then a'=c'=0; and L represents a partial structure represented by the formula (ii); L$_3$ represents a linear, branched or cyclic divalent organic group having 1 to 20 carbon atoms, L$_4$ represents L$_3$, the partial structure represented by the following formula (i), or the partial structure represented by the formula (ii), 0≤i≤1, 0≤j≤1 and i+j=1

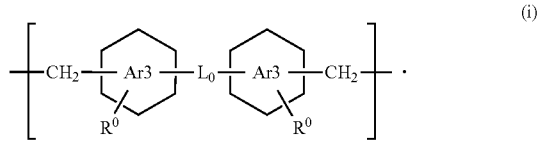

7. The compound for forming an organic film according to claim 1, wherein the compound contains a polymer having a partial structure represented by the following formula (vi),

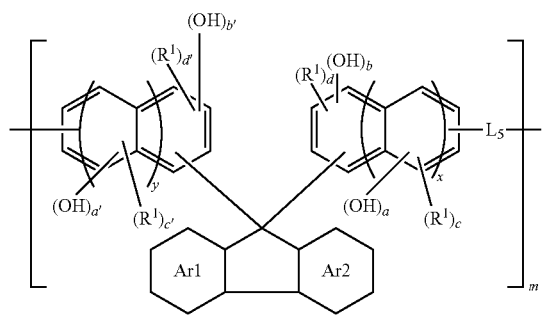

wherein R$^1$ represents a linear, branched or cyclic monovalent hydrocarbon group having 1 to 20 carbon atoms, and a methylene group constituting R$^1$ may be substituted by an oxygen atom; a+b and a'+b' are each independently 1, 2 or 3; c, d, c' and d' are each independently 0, 1 or 2; x and y each independently represent 0 or 1, when x=0, then a=c=0, and when y=0, then a'=c'=0; L$_5$ represents a linear, branched or cyclic divalent organic group having 1 to 20 carbon atoms, L$_6$ represents the partial structure represented by the formula (ii), 0≤m<1, 0<n≤1 and m+n=1.

8. The compound for forming an organic film according to claim 1, wherein the compound contains a polymer having a partial structure represented by the following formula (vii),

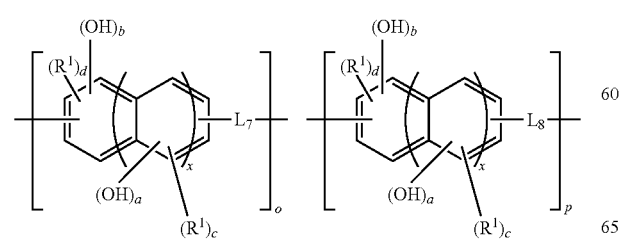

wherein R$^1$ represents a linear, branched or cyclic monovalent hydrocarbon group having 1 to 20 carbon atoms, and a methylene group constituting R$^1$ may be substituted by an oxygen atom; a+b is 1, 2 or 3; c and d are each independently 0, 1 or 2; x represents 0 or 1, when x=0, then a=c=0; L$_7$ represents a linear, branched or cyclic divalent organic group having 1 to 20 carbon atoms, L$_8$ represents the partial structure represented by the formula (ii), 0≤o<1, 0<p≤1 and o+p=1.

9. An organic film composition comprising the compound for forming an organic film according to claim 1, the organic film composition further comprising at least one selected from (A) a compound represented by the following formula (iii), (B) a compound having a partial structure represented by the following formula (iv), (C-1) a polymer compound having a partial structure represented by the following formula (iv) as a part of the repeating unit, (C-2) a polymer compound having a partial structure represented by the following formula (v), (C-3) a polymer compound having a partial structure represented by the following formula (vi), and (C-4) a polymer compound having a partial structure represented by the following formula (vii),

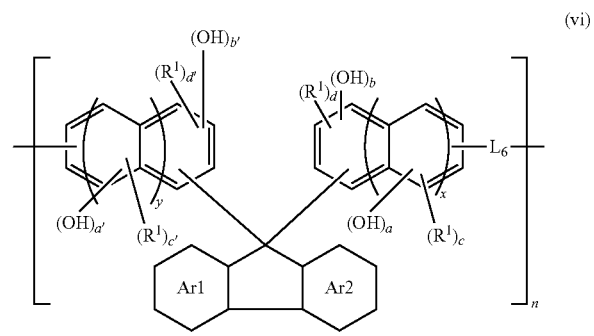

wherein the formula (iii) is represented by

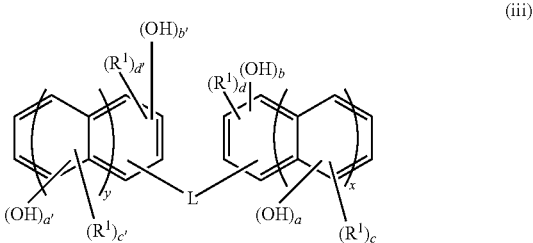

wherein R$^1$ represents a linear, branched or cyclic monovalent hydrocarbon group having 1 to 20 carbon atoms, and a methylene group constituting R$^1$ may be substituted by an oxygen atom; a+b and a'+b' are each independently 1, 2 or 3; c, d, c' and d' are each independently 0, 1 or 2; x and y each independently represent 0 or 1, when x=0, then a=c=0, and when y=0, then a'=c'=0; and L represents a partial structure represented by the formula (ii), the formula (iv) is represented by

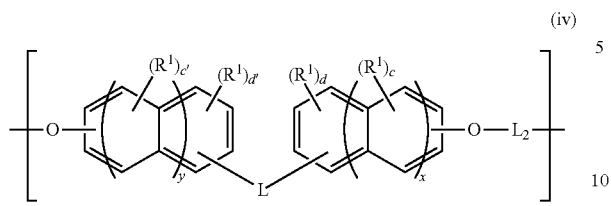

(iv)

wherein $R^1$ represents a linear, branched or cyclic monovalent hydrocarbon group having 1 to 20 carbon atoms, and a methylene group constituting $R^1$ may be substituted by an oxygen atom; c, d, c' and d' are each independently 0, 1 or 2; x and y each independently represent 0 or 1, when x=0, then c=0, and when y=0, then c'=0; L represents a partial structure represented by the formula (ii); $L_2$ represents a linear, branched or cyclic divalent organic group having 2 to 30 carbon atoms; and a methylene group constituting $L_2$ may be substituted by an oxygen atom or a carbonyl group, and the hydrogen atom constituting the structure may be substituted by a hydroxyl group, the formula (v) is represented by

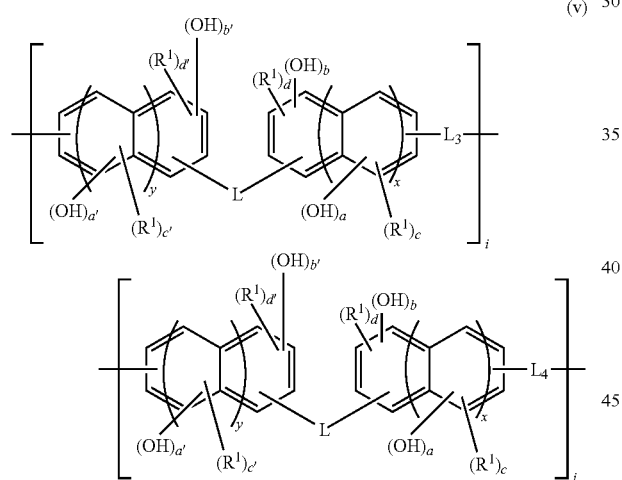

(v)

wherein $R^1$ represents a linear, branched or cyclic monovalent hydrocarbon group having 1 to 20 carbon atoms, and a methylene group constituting $R^1$ may be substituted by an oxygen atom; a+b and a'+b' are each independently 1, 2 or 3; c, d, c' and d' are each independently 0, 1 or 2; x and y each independently represent 0 or 1, when x=0, then a=c=0, and when y=0, then a'=c'=0; and L represents a partial structure represented by the formula (ii); $L_3$ represents a linear, branched or cyclic divalent organic group having 1 to 20 carbon atoms, $L_4$ represents $L_3$, the partial structure represented by the following formula (i), or the partial structure represented by the formula (ii), $0 \leq i \leq 1$, $0 \leq j \leq 1$ and i+j=1,

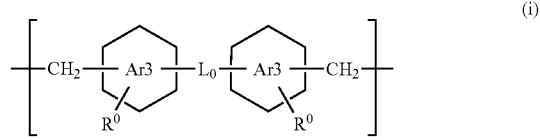

(i)

the formula (vi) is represented by

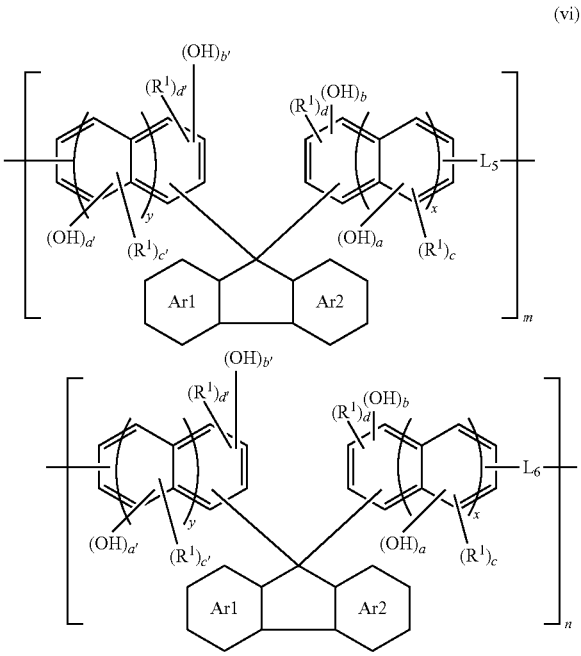

(vi)

wherein $R^1$ represents a linear, branched or cyclic monovalent hydrocarbon group having 1 to 20 carbon atoms, and a methylene group constituting $R^1$ may be substituted by an oxygen atom; a+b and a'+b' are each independently 1, 2 or 3; c, d, c' and d' are each independently 0, 1 or 2; x and y each independently represent 0 or 1, when x=0, then a=c=0, and when y=0, then a'=c'=0; $L_5$ represents a linear, branched or cyclic divalent organic group having 1 to 20 carbon atoms, $L_6$ represents the partial structure represented by the formula (ii), $0 \leq m < 1$, $0 < n \leq 1$ and m+n=1, and the formula (vii) is represented by

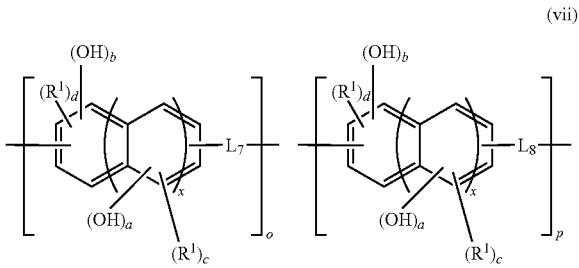

(vii)

wherein $R^1$ represents a linear, branched or cyclic monovalent hydrocarbon group having 1 to 20 carbon atoms, and a methylene group constituting $R^1$ may be substituted by an oxygen atom; a+b is 1, 2 or 3; c and d are each independently 0, 1 or 2; x represents 0 or 1, when x=0, then a=c=0; $L_7$ represents a linear, branched or cyclic divalent organic group having 1 to 20 carbon atoms, $L_8$ represents the partial structure represented by the formula (ii), 0≤o<1, 0<p≤1 and o+p=1.

10. The organic film composition according to claim 9, wherein the composition contains (D) a resin containing an aromatic ring which is different from the polymers (C-1) to (C-4).

11. The organic film composition according to claim 10, wherein (D) the resin containing an aromatic ring contains a naphthalene ring.

12. The organic film composition according to claim 10, wherein (D) the resin containing an aromatic ring contains a resin (D-1) obtained by polycondensating one or more kinds of compounds represented by the following formulae (3a) and (3b), and a compound represented by the following formula (4),

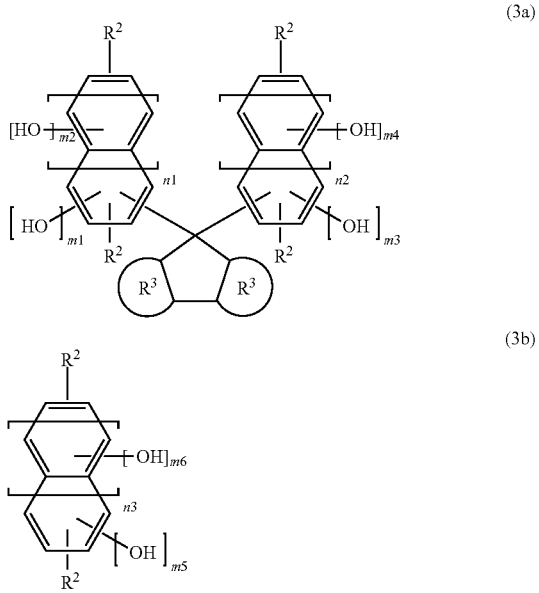

(3a)

(3b)

wherein each $R^2$ independently represent a hydrogen atom or a saturated or unsaturated hydrocarbon group having 1 to 20 carbon atoms; each $R^3$ independently represent a benzene ring or a naphthalene ring; m1+m2, m3+m4 and m5+m6 are each 1 or 2; n1, n2 and n3 are each 0 or 1,

A-CHO (4)

wherein A represents a hydrogen atom, a hydrocarbon group having 1 to 10 carbon atoms, or a substituted or unsubstituted aromatic hydrocarbon group having 6 to 20 carbon atoms.

13. The organic film composition according to claim 10, wherein (D) the resin containing an aromatic ring contains a resin (D-2) having one or more of a repeating unit(s) represented by the following formula (5),

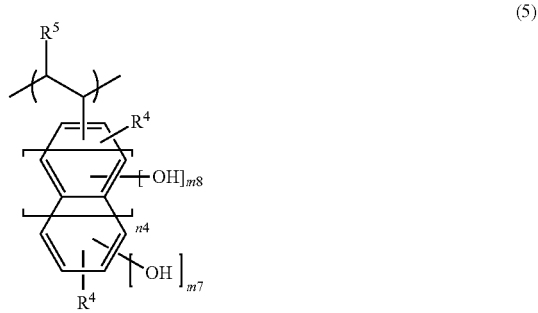

(5)

wherein each $R^4$ independently represent a hydrogen atom or a saturated or unsaturated hydrocarbon group having 1 to 20 carbon atoms; $R^5$ represents a hydrogen atom or may form a ring by bonding to one of $R^4$; when $R^4$ and $R^5$ are bonded to form a ring, —$R^4$—$R^5$— represents a single bond or an alkylene group having 1 to 3 carbon atoms; m7+m8 is 0, 1 or 2; and n4 is 0 or 1.

14. The organic film composition according to claim 9, wherein the composition further comprises at least one of (E) a compound containing a phenolic hydroxyl group, (F) an acid generator, (G) a cross-linking agent, (H) a surfactant and (I) an organic solvent.

15. A process for forming an organic film which acts as a resist underlayer film or a planarizing film for manufacturing a semiconductor apparatus of a multilayer resist film used in lithography, which comprises coating the organic film composition according to claim 9 on a substrate to be processed, and subjecting the composition to heat treatment at a temperature of 100° C. or higher and 600° C. or lower for 10 seconds to 600 seconds to form a cured film.

16. The method for forming an organic film according to claim 15, wherein the substrate to be processed is a substrate to be processed having a structural composition or step(s) each with a height of 30 nm or more.

17. A process for forming an organic film which acts as a resist underlayer film or a planarizing film for manufacturing a semiconductor apparatus of a multilayer resist film used in lithography, which comprises coating the organic film composition according to claim 9 on a substrate to be processed, and baking the composition in an atmosphere with an oxygen concentration of 0.1% or more and 21% or less to form a cured film.

18. The method for forming an organic film according to claim 17, wherein the substrate to be processed is a substrate to be processed having a structural composition or step(s) each with a height of 30 nm or more.

19. A patterning process which is a process for forming a pattern on a substrate to be processed, which comprises the steps of, at least, forming a resist underlayer film by using the organic film composition according to claim 9 on the substrate to be processed; forming a resist middle layer film composition on the resist underlayer film using a resist middle layer film composition containing a silicon atom; forming a resist upper layer film on the resist middle layer film by using a resist upper layer film composition comprising a photoresist composition, to form a multilayer resist film; conducting exposure of a pattern circuit region of the resist upper layer film and then developing it with a developer to form a resist pattern on the resist upper layer film; etching the resist middle layer film by using the pattern-formed resist upper layer film as an etching mask; etching the resist underlayer film by using the pattern-formed resist middle layer film as an etching mask; and further etching the substrate to be processed by using the obtained pattern-formed resist underlayer film as an etching mask, to form a pattern on the substrate to be processed.

20. The patterning process according to claim 19, wherein etching of the resist underlayer film by using the resist middle layer film as an etching mask is performed by using an etching gas mainly comprising an oxygen gas or a hydrogen gas.

21. A patterning process which is a process for forming a pattern on a substrate to be processed, which comprises the steps of, at least, forming a resist underlayer film by using the organic film composition according to claim 9 on the substrate to be processed; forming an inorganic hard mask middle layer film selected from any one of a silicon oxide film, a silicon nitride film and a silicon oxynitride film on the resist underlayer film; forming a resist upper layer film on the inorganic hard mask middle layer film by using a resist upper layer film composition comprising a photoresist composition, to prepare a multilayer resist film; conducting exposure of a pattern circuit region of the resist upper layer film and then developing it with a developer to form a resist pattern on the resist upper layer film; etching the inorganic hard mask middle layer film by using the obtained resist pattern as an etching mask; etching the resist underlayer film by using the obtained pattern-formed inorganic hard mask middle layer film as an etching mask; and further etching the substrate to be processed by using the obtained pattern-formed resist underlayer film as an etching mask, to form a pattern on the substrate to be processed.

22. The patterning process according to claim 21, wherein the inorganic hard mask middle layer film is formed by a CVD method or an ALD method.

23. The patterning process according to claim 21, wherein the substrate to be processed is a substrate to be processed having a structural composition or step(s) each with a height of 30 nm or more.

24. A patterning process which is a process for forming a pattern on a substrate to be processed, which comprises the steps of, at least, forming a resist underlayer film by using the organic film composition according to claim 9 on the substrate to be processed; forming an inorganic hard mask middle layer film selected from any one of a silicon oxide film, a silicon nitride film and a silicon oxynitride film on the resist underlayer film; forming an organic antireflection film on the inorganic hard mask middle layer film; forming a resist upper layer film on the organic antireflection film by using a resist upper layer film composition comprising a photoresist composition, to prepare a multilayer resist film; conducting exposure of a pattern circuit region of the resist upper layer film and then developing it with a developer to form a resist pattern on the resist upper layer film; etching the organic antireflection film and the inorganic hard mask middle layer film by using the obtained resist pattern as an etching mask; etching the resist underlayer film by using the obtained pattern-formed inorganic hard mask middle layer film as an etching mask; and further etching the substrate to be processed by using the obtained pattern-formed resist underlayer film as an etching mask, to form a pattern on the substrate to be processed.

25. The patterning process according to claim 24, wherein the inorganic hard mask middle layer film is formed by a CVD method or an ALD method.

26. The patterning process according to claim 24, wherein the substrate to be processed is a substrate to be processed having a structural composition or step(s) each with a height of 30 nm or more.

27. A resist underlayer film composition comprising the organic film composition according to claim 9.

28. A planarizing composition for manufacturing a semiconductor apparatus comprising the organic film composition according to claim 9.

* * * * *